US012629278B2

(12) United States Patent
Khalsa et al.

(10) Patent No.: US 12,629,278 B2
(45) Date of Patent: May 19, 2026

(54) TRANSVENOUS CRYONEUROLYSIS SYSTEM, DEVICES AND METHODS

(71) Applicant: Nervana Inc., Santa Monica, CA (US)

(72) Inventors: Bhavraj Khalsa, Manhattan Beach, CA (US); Ali Golshan, Santa Monica, CA (US); Richard S. Williams, Redwood City, CA (US)

(73) Assignee: Nervana Inc., Santa Monica, CA (US)

( * ) Notice: Subject to any disclaimer, the term of this patent is extended or adjusted under 35 U.S.C. 154(b) by 0 days.

(21) Appl. No.: 19/192,223

(22) Filed: Apr. 28, 2025

(65) Prior Publication Data

US 2025/0332026 A1      Oct. 30, 2025

Related U.S. Application Data

(60) Provisional application No. 63/639,516, filed on Apr. 26, 2024.

(51) Int. Cl.
A61F 7/12 (2006.01)
A61F 7/00 (2006.01)

(52) U.S. Cl.
CPC ...... A61F 7/123 (2013.01); A61F 2007/0044 (2013.01); A61F 2007/0045 (2013.01); A61F 2007/0056 (2013.01); A61F 2007/126 (2013.01)

(58) Field of Classification Search
CPC .. A61B 2018/00434; A61B 2018/0293; A61B 18/02; A61B 2018/00791;
(Continued)

(56) References Cited

U.S. PATENT DOCUMENTS

| 3,901,241 A | 8/1975 | Allen, Jr. et al. |
| 5,423,807 A | 6/1995 | Milder |
| (Continued) | | |

FOREIGN PATENT DOCUMENTS

| WO | WO98/016161 A1 | 4/1998 |
| WO | WO01/095820 A1 | 12/2001 |
| (Continued) | | |

OTHER PUBLICATIONS

Shah et al. Does cryoneurolysis result in persistent motor deficits? A controlled study using a rat peroneal nerve injury model. Reg Anesth Pain Med. Apr. 2020;45(4):287-292. (Year: 2020).*
(Continued)

*Primary Examiner* — Joseph A Stoklosa
*Assistant Examiner* — Adam J Avigan
(74) *Attorney, Agent, or Firm* — Shay Glenn LLP

(57) ABSTRACT

There is provided a transvenous approach for accessing and targeting neural treatment sites to relieve a variety of clinical indications, including peripheral neuropathy. A neurosome approach is described that includes one or more target nerves to receive selective cryoneurolysis via a target vein. A range of different freeze and thaw cycles are performed via the target vein to induce a desired thermal treatment temperature range for selective sensory loss without adverse impact or minimal impact to associated motor nerves. The target nerves and veins are selected to combine the treatment of the identified neurosome for pain relief in addition to the regenerative properties of cryoneurolysis.

25 Claims, 33 Drawing Sheets

(58) Field of Classification Search
CPC ....... A61B 2018/0212; A61F 2007/126; A61F 7/12; A61M 2205/3606

See application file for complete search history.

(56) References Cited

U.S. PATENT DOCUMENTS

| | | | |
|---|---|---|---|
| 6,283,959 B1 * | 9/2001 | Lalonde | A61B 18/02 |
| | | | 606/23 |
| 6,451,011 B2 | 9/2002 | Tu | |
| 6,564,096 B2 | 5/2003 | Mest | |
| 6,786,901 B2 | 9/2004 | Joye et al. | |
| 6,905,493 B2 | 6/2005 | Lentz | |
| 6,960,206 B2 | 11/2005 | Keane | |
| 7,008,418 B2 | 3/2006 | Hall et al. | |
| 7,101,368 B2 | 9/2006 | Lafontaine | |
| 7,172,586 B1 | 2/2007 | Dae et al. | |
| 7,172,589 B2 | 2/2007 | Lafontaine | |
| 7,195,628 B2 | 3/2007 | Falkenberg | |
| 7,241,295 B2 | 7/2007 | Maguire | |
| 7,252,663 B2 | 8/2007 | Reu et al. | |
| 7,303,560 B2 | 12/2007 | Chin et al. | |
| 7,594,915 B2 | 9/2009 | Kochamba et al. | |
| 7,655,005 B2 | 2/2010 | Bhola | |
| 7,850,723 B1 | 12/2010 | Magers | |
| 7,972,327 B2 | 7/2011 | Eberl et al. | |
| 8,080,006 B2 | 12/2011 | Lafontaine et al. | |
| 8,123,741 B2 | 2/2012 | Marrouche et al. | |
| 8,123,742 B2 | 2/2012 | Berger | |
| 8,343,202 B2 | 1/2013 | Magners | |
| 8,353,900 B2 | 1/2013 | Jung et al. | |
| 8,365,741 B2 | 2/2013 | Hennings et al. | |
| 8,480,664 B2 | 7/2013 | Watson et al. | |
| 8,672,930 B2 | 3/2014 | Wittenberger | |
| 8,672,988 B2 | 3/2014 | Hennemann et al. | |
| 8,679,104 B2 | 3/2014 | Abboud et al. | |
| 8,679,105 B2 | 3/2014 | Wittenberger | |
| 8,715,274 B2 | 5/2014 | Watson | |
| 8,790,300 B2 | 7/2014 | Tun et al. | |
| 8,821,484 B2 | 9/2014 | Ingel et al. | |
| 8,852,181 B2 | 10/2014 | Malecki et al. | |
| 8,870,859 B2 | 10/2014 | Swanson | |
| 8,880,185 B2 | 11/2014 | Hastings et al. | |
| 8,906,079 B2 | 12/2014 | D'Ambola et al. | |
| 8,974,451 B2 | 3/2015 | Smith | |
| 9,055,959 B2 | 6/2015 | Vaska et al. | |
| 9,060,761 B2 | 6/2015 | Hastings et al. | |
| 9,095,321 B2 | 8/2015 | Phelan et al. | |
| 9,095,350 B2 | 8/2015 | Condie et al. | |
| 9,149,320 B2 | 10/2015 | Kuck et al. | |
| 9,192,790 B2 | 11/2015 | Hastings et al. | |
| 9,220,555 B2 | 12/2015 | Asconeguy et al. | |
| 9,259,235 B2 | 2/2016 | Chierchia et al. | |
| 9,283,033 B2 | 3/2016 | Gelfand et al. | |
| 9,345,540 B2 | 5/2016 | Mallin et al. | |
| 9,439,706 B2 | 9/2016 | Abboud et al. | |
| 9,622,806 B2 | 4/2017 | Mihalik | |
| 9,629,675 B2 | 4/2017 | Kleshinski et al. | |
| 9,655,667 B2 | 5/2017 | Hon | |
| 9,724,018 B2 | 8/2017 | Cho et al. | |
| 9,743,973 B2 | 8/2017 | Pageard | |
| 9,833,623 B2 | 12/2017 | Gnanashanmugam et al. | |
| 9,844,644 B2 | 12/2017 | Osypka | |
| 9,848,946 B2 | 12/2017 | Edmunds et al. | |
| 9,861,437 B2 | 1/2018 | Melsky et al. | |
| 9,877,780 B2 | 1/2018 | Longoria | |
| 9,993,666 B2 | 6/2018 | Tsoref et al. | |
| 10,004,557 B2 | 6/2018 | Gross | |
| 10,159,521 B2 | 12/2018 | Jannicke et al. | |
| 10,194,979 B1 | 2/2019 | Brar et al. | |
| 10,231,778 B2 | 3/2019 | Highsmith et al. | |
| 10,398,501 B2 | 9/2019 | Willard | |
| 10,478,249 B2 | 11/2019 | Gross et al. | |
| 10,499,984 B2 | 12/2019 | Lim | |
| 10,646,713 B2 | 5/2020 | Hettrick et al. | |
| 10,743,933 B2 | 8/2020 | Smith et al. | |
| 10,849,676 B2 | 12/2020 | Van Langenhove | |
| 10,864,031 B2 | 12/2020 | Mazor et al. | |
| 10,874,455 B2 | 12/2020 | Sobotka | |
| 11,172,974 B2 | 11/2021 | Lalonde | |
| 11,206,984 B1 | 12/2021 | Boveia et al. | |
| 11,213,674 B2 | 1/2022 | Barman et al. | |
| 11,246,653 B2 | 2/2022 | Avitall | |
| 11,369,384 B2 | 6/2022 | Raabe et al. | |
| 11,389,230 B2 | 7/2022 | Panescu et al. | |
| 11,446,359 B2 | 9/2022 | Bright | |
| 11,471,207 B2 | 10/2022 | Columbe et al. | |
| 11,547,601 B2 | 1/2023 | Collins et al. | |
| 11,553,960 B2 | 1/2023 | Bohm et al. | |
| 11,553,963 B2 | 1/2023 | Franceschi et al. | |
| 11,596,794 B2 | 3/2023 | Yeh et al. | |
| 11,666,369 B2 | 6/2023 | Pageard | |
| 11,666,370 B2 | 6/2023 | Yang et al. | |
| 11,701,171 B2 | 7/2023 | Schultheis et al. | |
| 11,712,296 B2 | 8/2023 | Panescu et al. | |
| 11,759,141 B2 | 9/2023 | Franceschi et al. | |
| 11,801,092 B2 | 10/2023 | Levin et al. | |
| 11,806,073 B2 | 11/2023 | Bapana et al. | |
| 11,806,126 B2 | 11/2023 | Ben-Hami et al. | |
| 11,806,159 B2 | 11/2023 | Goedeke | |
| 11,826,569 B2 | 11/2023 | Mishara et al. | |
| 11,844,558 B2 | 12/2023 | Lazarus et al. | |
| 11,844,569 B1 | 12/2023 | Panescu et al. | |
| 11,864,826 B2 | 1/2024 | Levin et al. | |
| 11,890,044 B2 | 2/2024 | Tegg et al. | |
| 11,890,047 B2 | 2/2024 | Lazarus et al. | |
| 11,957,396 B2 | 4/2024 | Lalonde et al. | |
| 11,957,903 B2 | 4/2024 | Olson | |
| 11,963,712 B2 | 4/2024 | De Marchena | |
| 11,986,231 B2 | 5/2024 | Sara et al. | |
| 2001/0007940 A1 | 7/2001 | Tu et al. | |
| 2005/0027289 A1 | 2/2005 | Castellano et al. | |
| 2005/0038421 A1 | 2/2005 | Joye et al. | |
| 2005/0159798 A1 | 7/2005 | Graumann et al. | |
| 2005/0171527 A1 | 8/2005 | Bhola | |
| 2005/0261672 A1 | 11/2005 | Deem et al. | |
| 2006/0136023 A1 | 6/2006 | Dobak | |
| 2006/0224153 A1 | 10/2006 | Fischell et al. | |
| 2006/0247607 A1 | 11/2006 | Cornelius et al. | |
| 2008/0039746 A1 | 2/2008 | Hissong et al. | |
| 2008/0097297 A1 | 4/2008 | Kelly et al. | |
| 2008/0161803 A1 | 7/2008 | Oral et al. | |
| 2008/0312644 A1 | 12/2008 | Fourkas et al. | |
| 2009/0192505 A1 | 7/2009 | Askew et al. | |
| 2009/0312693 A1 | 12/2009 | Thapliyal et al. | |
| 2010/0049099 A1 | 2/2010 | Thapliyal et al. | |
| 2010/0152582 A1 | 6/2010 | Thapliyal et al. | |
| 2010/0241113 A1 | 9/2010 | Ingel | |
| 2010/0262132 A1 | 10/2010 | Rothstein et al. | |
| 2011/0144637 A1 | 6/2011 | Pageard et al. | |
| 2011/0257562 A1 | 10/2011 | Schaer | |
| 2011/0257641 A1 | 10/2011 | Hastings et al. | |
| 2011/0306904 A1 | 12/2011 | Jacobson et al. | |
| 2012/0016355 A1 | 1/2012 | George et al. | |
| 2012/0029496 A1 | 2/2012 | Smith | |
| 2012/0029512 A1 | 2/2012 | Willard et al. | |
| 2012/0059286 A1 | 3/2012 | Hastings et al. | |
| 2012/0065506 A1 | 3/2012 | Smith | |
| 2012/0065554 A1 | 3/2012 | Pikus | |
| 2012/0123261 A1 | 5/2012 | Jenson et al. | |
| 2012/0136349 A1 | 5/2012 | Hastings | |
| 2012/0136418 A1 * | 5/2012 | Buckley | A61B 18/02 |
| | | | 607/105 |
| 2012/0172680 A1 | 7/2012 | Gelfand et al. | |
| 2012/0197244 A1 | 8/2012 | Siegel et al. | |
| 2013/0035681 A1 | 2/2013 | Subramaniam et al. | |
| 2013/0053732 A1 | 2/2013 | Heuser | |
| 2013/0178910 A1 * | 7/2013 | Azamian | A61B 18/1492 |
| | | | 607/33 |
| 2013/0197555 A1 | 8/2013 | Schaer | |
| 2013/0218029 A1 | 8/2013 | Cholette et al. | |
| 2013/0274712 A1 | 10/2013 | Schecter | |
| 2013/0289678 A1 | 10/2013 | Clark et al. | |
| 2014/0031804 A1 | 1/2014 | Lalonde | |
| 2014/0058294 A1 | 2/2014 | Gross et al. | |

(56) References Cited

U.S. PATENT DOCUMENTS

| | | |
|---|---|---|
| 2014/0058372 A1 | 2/2014 | Belson |
| 2014/0107636 A1 | 4/2014 | Bencini |
| 2014/0114215 A1 | 4/2014 | Melder et al. |
| 2014/0163652 A1 | 6/2014 | Witzel et al. |
| 2014/0200567 A1 | 7/2014 | Cox et al. |
| 2014/0243807 A1 | 8/2014 | Margolis |
| 2014/0316398 A1 | 10/2014 | Kelly et al. |
| 2015/0018904 A1 | 1/2015 | Lafontaine |
| 2015/0051595 A1 | 2/2015 | Margolis |
| 2015/0112145 A1 | 4/2015 | Fleischman et al. |
| 2015/0133918 A1 | 5/2015 | Schar |
| 2015/0173830 A1 | 6/2015 | Johnson et al. |
| 2015/0182275 A1 | 7/2015 | Tsoref et al. |
| 2015/0223877 A1 | 8/2015 | Behar et al. |
| 2015/0272654 A1* | 10/2015 | Esch .................. A61B 18/1492 606/34 |
| 2015/0297281 A1 | 10/2015 | Sutermeister et al. |
| 2015/0297398 A1 | 10/2015 | Farrugia et al. |
| 2016/0000502 A1 | 1/2016 | Thapliyal et al. |
| 2016/0038769 A1* | 2/2016 | Sullivan .................. G16H 20/30 607/113 |
| 2016/0066975 A1 | 3/2016 | Fourkas et al. |
| 2016/0113711 A1 | 4/2016 | Osypka et al. |
| 2016/0184011 A1 | 6/2016 | Krishnan |
| 2016/0199131 A1 | 7/2016 | Allison et al. |
| 2016/0206372 A1 | 7/2016 | Rivlin |
| 2016/0249970 A1 | 9/2016 | Yu et al. |
| 2016/0324567 A1 | 11/2016 | Panescu et al. |
| 2017/0027640 A1 | 2/2017 | Kunis et al. |
| 2017/0042601 A1 | 2/2017 | Kim et al. |
| 2017/0049499 A1 | 2/2017 | Whiteley |
| 2017/0100604 A1 | 4/2017 | Schwab et al. |
| 2017/0120079 A1 | 5/2017 | Scheuermann et al. |
| 2017/0273741 A1 | 9/2017 | Sogard et al. |
| 2017/0354475 A1 | 12/2017 | Allison et al. |
| 2018/0028264 A1 | 2/2018 | Onik et al. |
| 2018/0092682 A1 | 4/2018 | Lawinger et al. |
| 2018/0132931 A1 | 5/2018 | Brennan |
| 2018/0177549 A1 | 6/2018 | Harrington et al. |
| 2018/0264260 A1 | 9/2018 | Zarins |
| 2018/0325576 A1 | 11/2018 | Harrington |
| 2019/0001139 A1* | 1/2019 | Mishra .................. A61N 1/0556 |
| 2019/0053847 A1 | 2/2019 | Tandri et al. |
| 2019/0083750 A1 | 3/2019 | Rezac |
| 2019/0183556 A1 | 6/2019 | Buckley et al. |
| 2019/0183569 A1* | 6/2019 | Panescu ............. A61B 18/1492 |
| 2019/0314616 A1 | 10/2019 | Moll et al. |
| 2019/0314617 A1 | 10/2019 | Harmouche |
| 2019/0336194 A1 | 11/2019 | Yu et al. |
| 2019/0350634 A1 | 11/2019 | Jung et al. |
| 2019/0380762 A1 | 12/2019 | Dahlen et al. |
| 2020/0008869 A1 | 1/2020 | Byrd |
| 2020/0038087 A1 | 2/2020 | Harmouche |
| 2020/0038638 A1 | 2/2020 | Gliner |
| 2020/0093531 A1 | 3/2020 | Harmouche |
| 2020/0129218 A1 | 4/2020 | Sliwa et al. |
| 2020/0129220 A1 | 4/2020 | Jung |
| 2020/0179045 A1* | 6/2020 | Levin ..................... A61B 5/024 |
| 2020/0188006 A1 | 6/2020 | Harmouche |
| 2020/0197067 A1 | 6/2020 | Jung |
| 2020/0197086 A1 | 6/2020 | Azamain et al. |
| 2020/0197088 A1 | 6/2020 | Vrba et al. |
| 2020/0206024 A1 | 7/2020 | Karnik et al. |
| 2020/0206498 A1 | 7/2020 | Arora et al. |
| 2020/0214756 A1 | 7/2020 | Kim et al. |
| 2020/0281646 A1* | 9/2020 | Pellegrino .......... A61B 17/3472 |
| 2020/0337765 A1 | 10/2020 | Smith |
| 2020/0367964 A1 | 11/2020 | Byrd et al. |
| 2020/0383723 A1 | 12/2020 | Hu et al. |
| 2021/0038101 A1 | 2/2021 | Wu et al. |
| 2021/0046016 A1 | 2/2021 | Toth et al. |
| 2021/0077173 A1 | 3/2021 | Diao et al. |
| 2021/0077180 A1 | 3/2021 | Govari |
| 2021/0113266 A1 | 4/2021 | Toth et al. |
| 2021/0121229 A1 | 4/2021 | Van Langenhove |
| 2021/0145534 A1 | 5/2021 | Kulstad et al. |
| 2021/0153935 A1 | 5/2021 | De La Rama et al. |
| 2021/0177482 A1 | 6/2021 | Tegg et al. |
| 2021/0177483 A1 | 6/2021 | Tegg et al. |
| 2021/0205501 A1 | 7/2021 | Bright |
| 2021/0220623 A1* | 7/2021 | Humbert ................ A61B 17/11 |
| 2021/0244467 A1 | 8/2021 | Aeby |
| 2021/0259762 A1 | 8/2021 | Barman et al. |
| 2021/0267542 A1 | 9/2021 | Toth et al. |
| 2021/0290285 A1 | 9/2021 | Avitall et al. |
| 2021/0315627 A1 | 10/2021 | Babkin et al. |
| 2021/0315638 A1 | 10/2021 | Townley et al. |
| 2021/0330380 A1 | 10/2021 | Grunewald et al. |
| 2021/0330981 A1 | 10/2021 | Mishra et al. |
| 2021/0386469 A1 | 12/2021 | Melder |
| 2022/0008111 A1 | 1/2022 | Zhao et al. |
| 2022/0023627 A1 | 1/2022 | Sullivan et al. |
| 2022/0031377 A1 | 2/2022 | Ransbury et al. |
| 2022/0031378 A1 | 2/2022 | Toth et al. |
| 2022/0071682 A1 | 3/2022 | Wittenberger et al. |
| 2022/0079666 A1 | 3/2022 | Ku et al. |
| 2022/0095979 A1 | 3/2022 | Shimada et al. |
| 2022/0096153 A1 | 3/2022 | Rothman et al. |
| 2022/0104762 A1 | 4/2022 | Toth et al. |
| 2022/0118251 A1 | 4/2022 | Buddah et al. |
| 2022/0125436 A1 | 4/2022 | Sunkara |
| 2022/0160424 A1 | 5/2022 | Rothman et al. |
| 2022/0175388 A1 | 6/2022 | Sunkara et al. |
| 2022/0176108 A1 | 6/2022 | Linden et al. |
| 2022/0176133 A1 | 6/2022 | Buddah et al. |
| 2022/0202472 A1 | 6/2022 | Morejohn et al. |
| 2022/0226034 A1 | 7/2022 | Smail |
| 2022/0240807 A1 | 8/2022 | Hettrick et al. |
| 2022/0249851 A1 | 8/2022 | Toth et al. |
| 2022/0280230 A1 | 9/2022 | Pilcher et al. |
| 2022/0296296 A1 | 9/2022 | Toth et al. |
| 2022/0314008 A1 | 10/2022 | Yeh et al. |
| 2022/0323142 A1 | 10/2022 | Gelfand et al. |
| 2022/0323146 A1 | 10/2022 | Panescu et al. |
| 2022/0346870 A1 | 11/2022 | Holmes, Jr. et al. |
| 2022/0354566 A1 | 11/2022 | Schwartz et al. |
| 2022/0361937 A1 | 11/2022 | Schwartz |
| 2023/0000562 A1 | 1/2023 | Ibragimov et al. |
| 2023/0029600 A1 | 2/2023 | Pivonka et al. |
| 2023/0039891 A1 | 2/2023 | Jimenez et al. |
| 2023/0040877 A1 | 2/2023 | Reo et al. |
| 2023/0057437 A1 | 2/2023 | Sullivan et al. |
| 2023/0066858 A1 | 3/2023 | Toth et al. |
| 2023/0095567 A1 | 3/2023 | Avitali |
| 2023/0129373 A1 | 4/2023 | Sit et al. |
| 2023/0165618 A1 | 6/2023 | Hartman et al. |
| 2023/0165634 A1 | 6/2023 | Iranitalab et al. |
| 2023/0172549 A1 | 6/2023 | Toth et al. |
| 2023/0218231 A1 | 7/2023 | Chou et al. |
| 2023/0218340 A1 | 7/2023 | Werneth et al. |
| 2023/0248427 A1 | 8/2023 | Koblish et al. |
| 2023/0248976 A1 | 8/2023 | Christian et al. |
| 2023/0255673 A1 | 8/2023 | Babkin et al. |
| 2023/0256252 A1 | 8/2023 | Brandner et al. |
| 2023/0293000 A1 | 9/2023 | Amirana et al. |
| 2023/0293229 A1 | 9/2023 | Barman et al. |
| 2023/0302301 A1 | 9/2023 | Sobotka et al. |
| 2023/0310053 A1 | 10/2023 | Wu et al. |
| 2023/0310055 A1 | 10/2023 | Anderson et al. |
| 2023/0329783 A1 | 10/2023 | Coates |
| 2023/0338091 A1 | 10/2023 | Papini et al. |
| 2023/0380881 A1 | 11/2023 | Chen |
| 2023/0389852 A1 | 12/2023 | Zhai |
| 2023/0390405 A1 | 12/2023 | Tsuriel et al. |
| 2023/0390551 A1 | 12/2023 | Waldhauser et al. |
| 2023/0404662 A1 | 12/2023 | Wu et al. |
| 2023/0414278 A1 | 12/2023 | Schuler et al. |
| 2024/0041518 A1 | 2/2024 | Melton et al. |
| 2024/0050711 A1 | 2/2024 | Xi et al. |
| 2024/0050747 A1 | 2/2024 | Mishra et al. |
| 2024/0057939 A1 | 2/2024 | Wang |
| 2024/0057945 A1 | 2/2024 | Brockway et al. |
| 2024/0058047 A1 | 2/2024 | Babkin et al. |
| 2024/0058057 A1 | 2/2024 | Asirvatham et al. |

(56) References Cited

U.S. PATENT DOCUMENTS

| | | |
|---|---|---|
| 2024/0081899 A1 | 3/2024 | Nguyen et al. |
| 2024/0108404 A1 | 4/2024 | Weiss et al. |
| 2024/0115305 A1 | 4/2024 | Levanony et al. |
| 2024/0130671 A1 | 4/2024 | Goedeke et al. |
| 2024/0130772 A1 | 4/2024 | Azamian et al. |
| 2024/0130773 A1 | 4/2024 | Azamian et al. |
| 2024/0130774 A1 | 4/2024 | Azamian et al. |
| 2024/0138896 A1 | 5/2024 | Azamian et al. |
| 2024/0139517 A1 | 5/2024 | Mishra |
| 2024/0156521 A1 | 5/2024 | Panescu et al. |

FOREIGN PATENT DOCUMENTS

| | | |
|---|---|---|
| WO | WO03/026477 A2 | 4/2003 |
| WO | WO2005/113068 A1 | 12/2005 |
| WO | WO2006/009580 A3 | 1/2006 |
| WO | WO2006/083674 A3 | 8/2006 |
| WO | WO2007/109171 A3 | 9/2007 |
| WO | WO2008/074026 A3 | 6/2008 |
| WO | WO2008/156353 A1 | 12/2008 |
| WO | WO2009/010963 A3 | 1/2009 |
| WO | WO2009/112262 A3 | 9/2009 |
| WO | WO2010/018569 A1 | 2/2010 |
| WO | WO2010/088301 A1 | 8/2010 |
| WO | WO2011/140331 A1 | 11/2011 |
| WO | WO2012/071058 A1 | 5/2012 |
| WO | WO2014/205442 A1 | 12/2014 |
| WO | WO2015/073970 A1 | 5/2015 |
| WO | WO2016/059027 A1 | 4/2016 |
| WO | WO2016/086160 A1 | 6/2016 |
| WO | WO2017/009165 A1 | 1/2017 |
| WO | WO2017/047545 A1 | 3/2017 |
| WO | WO2018/148561 A1 | 8/2018 |
| WO | WO2018/161627 A1 | 9/2018 |
| WO | WO2018/204586 A1 | 11/2018 |
| WO | WO2018/217516 A1 | 11/2018 |
| WO | WO2019/005501 A1 | 1/2019 |
| WO | WO2019/023185 A1 | 1/2019 |
| WO | WO2019/094090 A1 | 5/2019 |
| WO | WO2019/099472 A1 | 5/2019 |
| WO | WO2019/111180 A1 | 6/2019 |
| WO | WO2019/139924 A1 | 7/2019 |
| WO | WO2019/143956 A1 | 7/2019 |
| WO | WO2019/161055 A1 | 8/2019 |
| WO | WO2019/189702 A1 | 10/2019 |
| WO | WO2019/196943 A1 | 10/2019 |
| WO | WO2020/046839 A1 | 3/2020 |
| WO | WO2020/104462 A1 | 5/2020 |
| WO | WO2020/198165 A8 | 10/2020 |
| WO | WO2021/044310 A8 | 3/2021 |
| WO | WO2021/089569 A1 | 5/2021 |
| WO | WO2021/091566 A1 | 5/2021 |
| WO | WO2021/108600 A1 | 6/2021 |
| WO | WO2021/142352 A1 | 7/2021 |
| WO | WO2022/002714 A1 | 1/2022 |
| WO | WO2022/063098 A1 | 3/2022 |
| WO | WO2022/099013 A1 | 5/2022 |
| WO | WO2022/170275 A9 | 8/2022 |
| WO | WO2022/192522 A1 | 9/2022 |
| WO | WO2022/197748 A1 | 9/2022 |
| WO | WO2022/199159 A1 | 9/2022 |
| WO | WO2022/219604 A1 | 10/2022 |
| WO | WO2022/223417 A1 | 10/2022 |
| WO | WO2022/251163 A1 | 12/2022 |
| WO | WO2022/261022 A1 | 12/2022 |
| WO | WO2022/266327 A1 | 12/2022 |
| WO | WO2022/269545 A3 | 12/2022 |
| WO | WO2023/003934 A1 | 1/2023 |
| WO | WO2023/009548 A1 | 2/2023 |
| WO | WO2023/009586 A1 | 2/2023 |
| WO | WO2023/018937 A1 | 2/2023 |
| WO | WO2023/049954 A1 | 4/2023 |
| WO | WO2023/096859 A1 | 6/2023 |
| WO | WO2023/114991 A1 | 6/2023 |
| WO | WO2023/117484 A1 | 6/2023 |
| WO | WO2023/118183 A1 | 6/2023 |
| WO | WO2023/118194 A1 | 6/2023 |
| WO | WO2023/150489 A2 | 8/2023 |
| WO | WO2023/161287 A1 | 8/2023 |
| WO | WO2023/187469 A2 | 10/2023 |
| WO | WO2023/187510 A1 | 10/2023 |
| WO | WO2023/205577 A1 | 10/2023 |
| WO | WO2023/212185 A1 | 11/2023 |
| WO | WO2024/006466 A1 | 1/2024 |
| WO | WO2024/011128 A1 | 1/2024 |
| WO | WO2024/015555 A1 | 1/2024 |
| WO | WO2024/046968 A1 | 3/2024 |
| WO | WO2024/068920 A1 | 4/2024 |
| WO | WO2024/073615 A1 | 4/2024 |
| WO | WO2024/086033 A1 | 4/2024 |
| WO | WO2024/088741 A1 | 5/2024 |
| WO | WO2025/227164 A1 | 10/2025 |

OTHER PUBLICATIONS

Ziegler D. Painful diabetic neuropathy: advantage of novel drugs over old drugs? Diabetes Care. Nov. 2009;32 Suppl 2(Suppl 2): S414-9. (Year: 2009).*

Ahmed et al.; Principles of and advances in percutaneous ablation. Radiology; 258(2); pp. 351-369; Feb. 2011.

Biel et al.; The applications of cryoneurolysis for acute and chronic pain management; Pain Practice; 23(2); pp. 204-215; Feb. 2023.

Castelli et al.; Peripheral neuropathy: evaluation and differential diagnosis; American family physician; 102(12); pp. 732-739; Dec. 15, 2020.

Center of Disease Conrol: Overdoes Prevention; Understanding the opioid overdose epidemic; 4 pages; retrieved from the internet (https://www.cdc.gov/overdose-prevention/about/understanding-the-opioid-overdose-epidemic.html?CDC_AAref_Val=https://www.cdc.gov/opioids/basics/epidemic.html#print); Mar. 7, 2023.

Fan et al.; Trends in pain medication initiation among patients with newly diagnosed diabetic peripheral neuropathy, 2014-2018; JAMA network open; 4(1); e2035632-; Jan. 4, 2021.

Finnerup et al.; Pharmacotherapy for neuropathic pain in adults: a systematic review and meta-analysis; The Lancet Neurology; 14(2); pp. 162-173; Feb. 1, 2015.

Franzen-Korzendorfer et al.; The effect of monochromatic infrared energy on transcutaneous oxygen measurements and protective sensation: results of a controlled, double-blind, randomized clinical study; Ostomy/wound management; 54(6); pp. 16-31; Jun. 1, 2008.

Green-Filgham et al.; Oxycodone, fentanyl, and morphine amplify established neuropathic pain in male rats; Pain; 160(11); 2634-2640; Nov. 1, 2019.

Geuna et al.; Histology of the peripheral nerve and changes occurring during nerve regeneration; International review of neurobiology; vol. 87; pp. 27-46; Jan. 1, 2009.

Hicks et al.; Epidemiology of peripheral neuropathy and lower extremity disease in diabetes; Current diabetes reports; 19(86); pp. 1-8; Oct. 2019.

Hicks et al.; Prevalence of peripheral neuropathy defined by monofilament insensitivity in middle-aged and older adults in two US cohorts; Scientific Reports; 11(1); 19159; Sep. 27, 2021.

Jones et al.; Drug-induced peripheral neuropathy: a narrative review; Current clinical pharmacology; 15(1); pp. 38-48; Apil 1, 2020.

Lancet; Opioid crisis: addiction, overprescription, and insufficient primary prevention; The Lancet Regional Health-Americas; Editorial; vol. 23; 100557; doi: 10.1016/j.lana.2023.100557; Jul. 12, 2023.

Lavery et al.; Does anodyne light therapy improve peripheral neuropathy in diabetes? A double-blind, sham-controlled, randomized trial to evaluate monochromatic infrared photoenergy. Diabetes Care 31, 316-321, doi:10.2337/dc07-1794 (2008).

Mattson; Trends and geographic patterns in drug and synthetic opioid overdose deaths—United States, 2013R2019; MMWR. Morbidity and mortality weekly report; vol. 70; pp. 202-207; Feb. 12, 2021.

(56)                    References Cited

OTHER PUBLICATIONS

Pesa et al.; Opioid utilization patterns among medicare patients with diabetic peripheral neuropathy; American health & drug benefits; 6(4); pp. 188-196; May 2013.

Prologo et al.; Percutaneous image-guided cryoablation for the treatment of phantom limb pain in amputees: a pilot study; Journal of Vascular and Interventional Radiology; 28(1); pp. 24-34; Jan. 1, 2017.

Rickard et al.; Chronic pain among adults—United States, 2019R2021; MMWR; Morbidity and Mortality Weekly Report; 72(15); 2023.

Sag et al.; Thermal protection strategies and neuromonitoring during ablation; InSeminars in Interventional Radiology; Thieme Medical Publishers, Inc.; 39(2); pp. 157-161; Apr. 2022.

Shah et al.; Does cryoneurolysis result in persistent motor deficits? A controlled study using a rat peroneal nerve injury model; Regional Anesthesia & Pain Medicine; 45(4); pp. 287-292; Apr. 1, 2020.

Vilholm et al.; Drug?induced peripheral neuropathy; Basic & clinical pharmacology & toxicology; 115(2); pp. 185-192; Aug. 2014.

\* cited by examiner

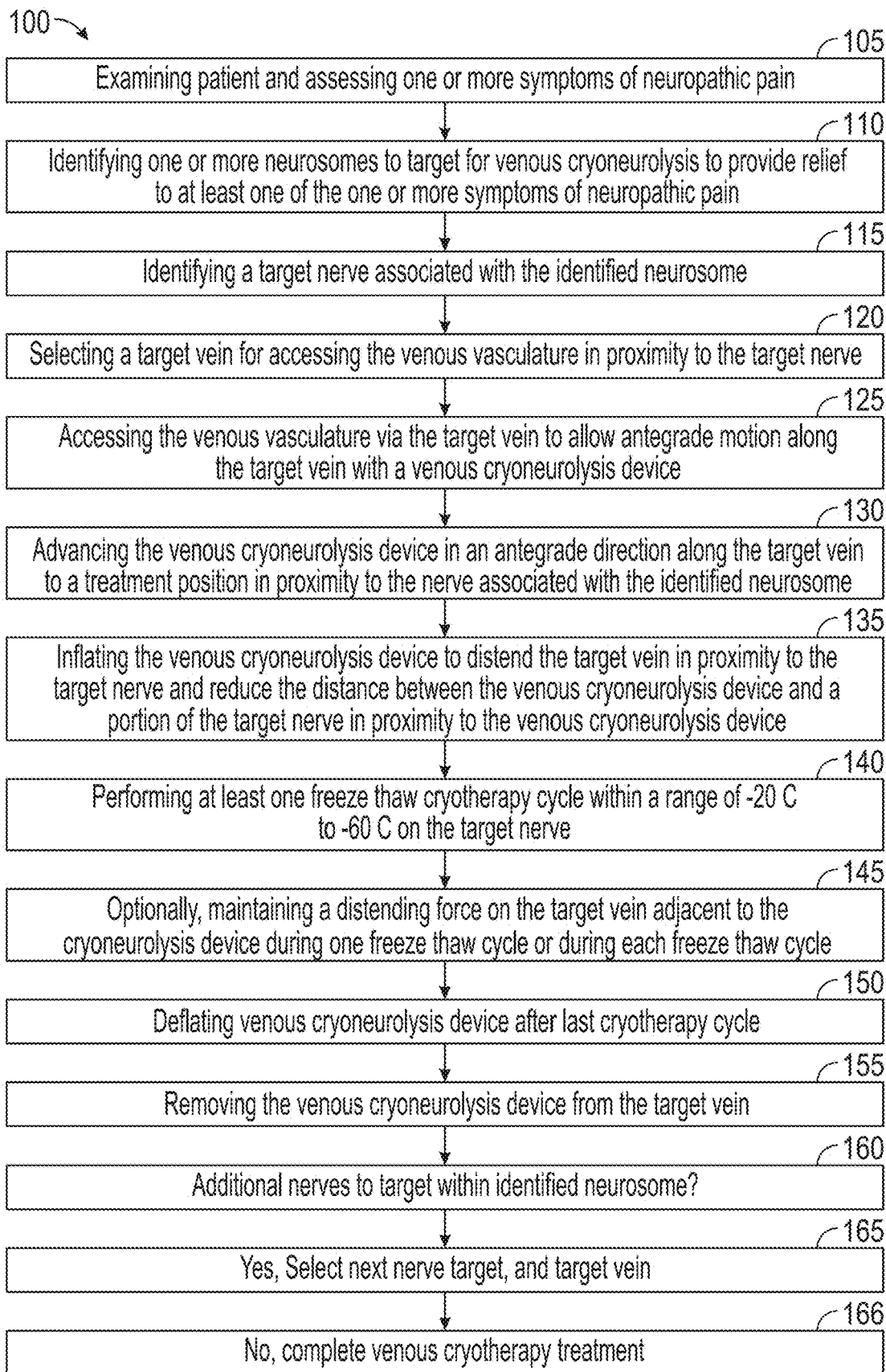

100

105
Examining patient and assessing one or more symptoms of neuropathic pain

110
Identifying one or more neurosomes to target for venous cryoneurolysis to provide relief to at least one of the one or more symptoms of neuropathic pain 115
Identifying a target nerve associated with the identified neurosome 120
Selecting a target vein for accessing the venous vasculature in proximity to the target nerve 125
Accessing the venous vasculature via the target vein to allow antegrade motion along the target vein with a venous cryoneurolysis device 130
Advancing the venous cryoneurolysis device in an antegrade direction along the target vein to a treatment position in proximity to the nerve associated with the identified neurosome 135
Inflating the venous cryoneurolysis device to distend the target vein in proximity to the target nerve and reduce the distance between the venous cryoneurolysis device and a portion of the target nerve in proximity to the venous cryoneurolysis device 140
Performing at least one freeze thaw cryotherapy cycle within a range of -20 C to -60 C on the target nerve 145
Optionally, maintaining a distending force on the target vein adjacent to the cryoneurolysis device during one freeze thaw cycle or during each freeze thaw cycle 150
Deflating venous cryoneurolysis device after last cryotherapy cycle 155
Removing the venous cryoneurolysis device from the target vein 160
Additional nerves to target within identified neurosome?

165
Yes, Select next nerve target, and target vein

166
No, complete venous cryotherapy treatment

FIG. 1

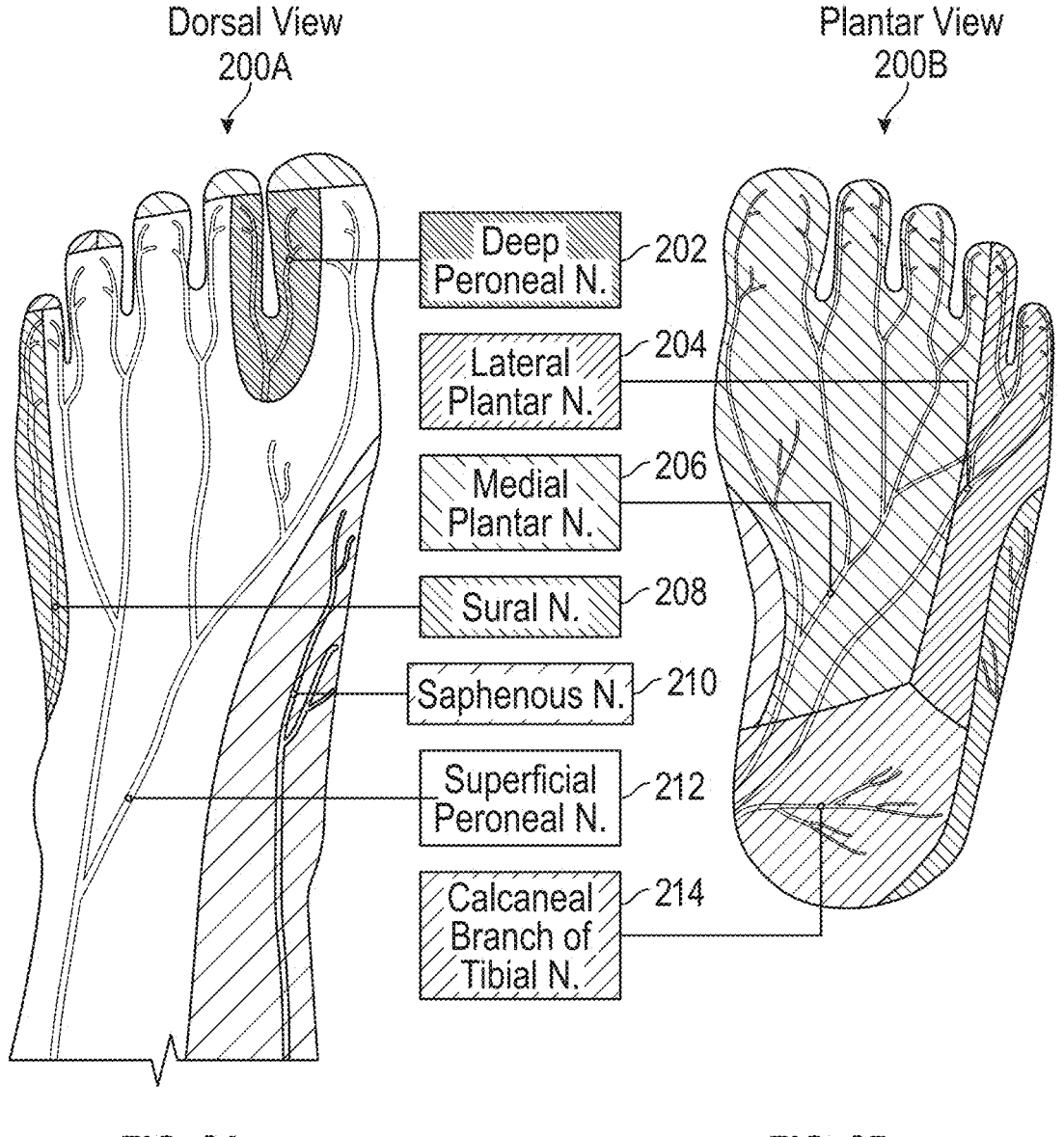
Dorsal View
200A
Plantar View
200B
Deep Peroneal N. — 202
Lateral Plantar N. — 204
Medial Plantar N. — 206
Sural N. — 208
Saphenous N. — 210
Superficial Peroneal N. — 212
Calcaneal Branch of Tibial N. — 214
FIG. 2A                    FIG. 2B Dorsal View
300A Plantar View
300B Dorsal View
400A 408
Deep Fibular Nerve 402
Superficial
Fibular Nerve 412
Antegrade direction,
ankle access, moving up
the leg 404
Branch of Deep
Fibular to
Extensor
Digitorum Brevis 406
Extensor
Digitorum
Brevis 410
Branches to First
and Second Dorsal
Interosseus Plantar View
400B Superficial
Branch
414

Deep Branch
422

Medial Plantar
Nerve
420

Lateral Plantar
Nerve
416

Medial Plantar
Vein
424

Lateral Plantar Vein
426

Tibial Nerve
418

600

Tendon of Flexor
Digitorum Longs
612

Posterior
Tibial Artery       Posterior
608              Tibial Vein
                    610

Tendon of
Tibialis Posterior
614

Posterior Tibial
Vein 606

618
Antegrade direction, ankle access,
moving up the leg

Tibial Nerve
604

Tendon of Flexor
Hallucis Longus
602

Pulse of Post-tibial Artery
Mid-way Between Heel
and Medial Malleolus
616

Ankle – Cross-section (Axial Cross Section)

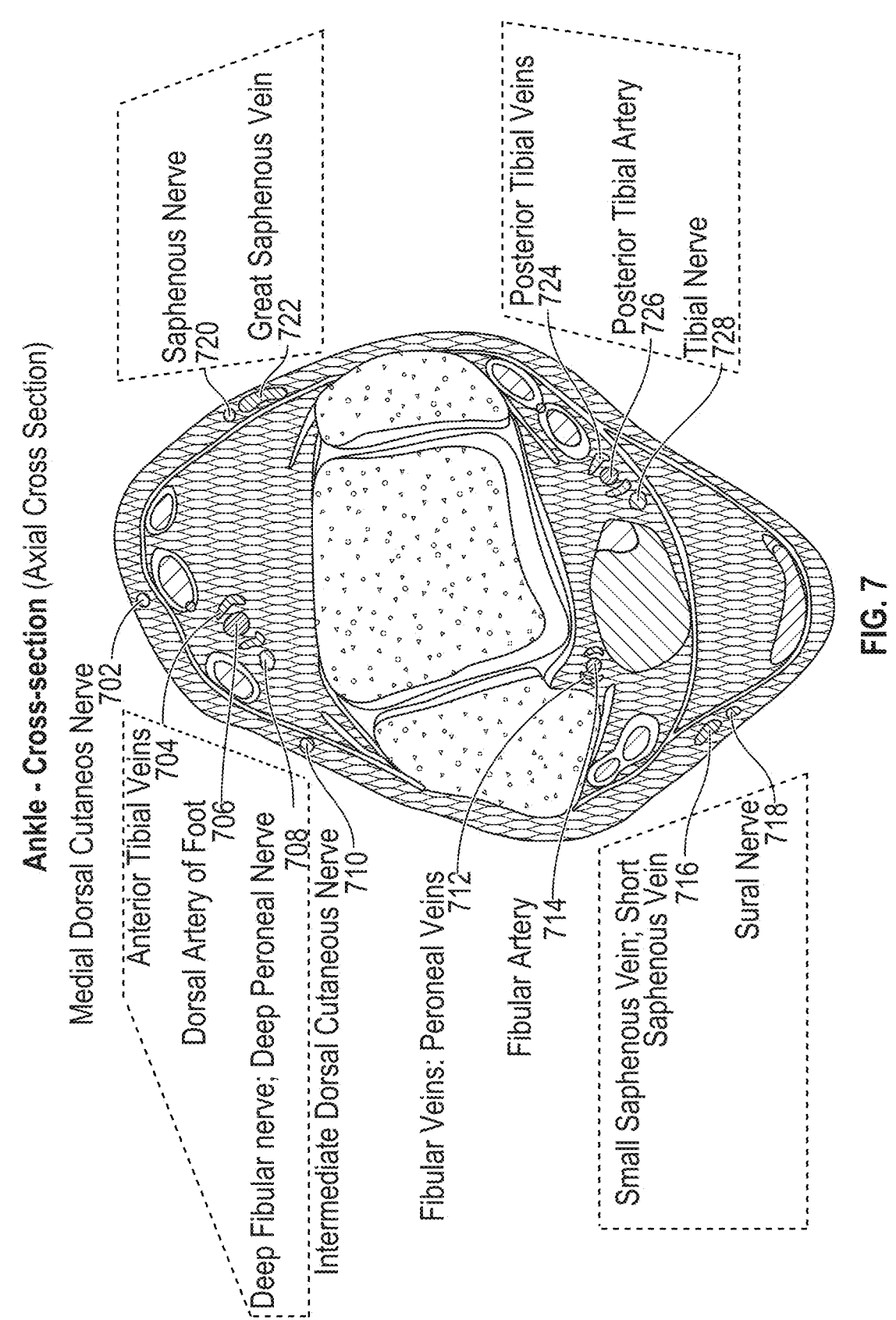

Saphenous Nerve 720

Great Saphenous Vein 722

Posterior Tibial Veins 724

Posterior Tibial Artery 726

Tibial Nerve 728

Medial Dorsal Cutaneos Nerve 702

Anterior Tibial Veins 704

Dorsal Artery of Foot 706

Deep Fibular nerve; Deep Peroneal Nerve 708

Intermediate Dorsal Cutaneous Nerve 710

Fibular Veins: Peroneal Veins 712

Fibular Artery 714

Small Saphenous Vein; Short Saphenous Vein 716

Sural Nerve 718

FIG. 7

Leg- Cross-section (Axial Cross Section)

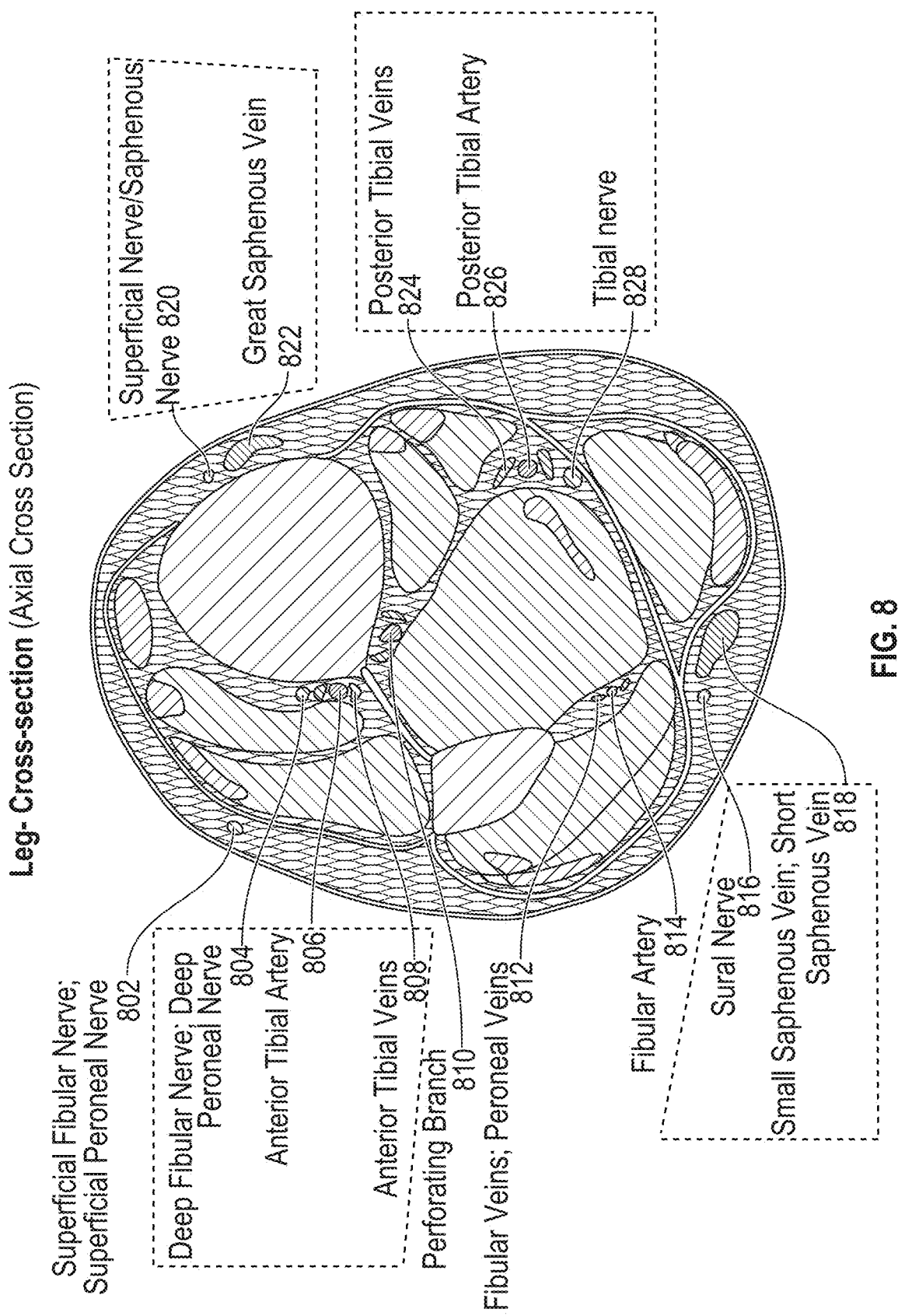

Superficial Fibular Nerve;
Superficial Peroneal Nerve
802

Superficial Nerve/Saphenous
Nerve 820

Great Saphenous Vein
822

Posterior Tibial Veins
824

Posterior Tibial Artery
826

Tibial nerve
828

Deep Fibular Nerve; Deep
Peroneal Nerve
804

Anterior Tibial Artery
806

Anterior Tibial Veins
808

Perforating Branch
810

Fibular Veins; Peroneal Veins
812

Fibular Artery
814

Sural Nerve
816

Small Saphenous Vein; Short
Saphenous Vein
818

FIG. 8

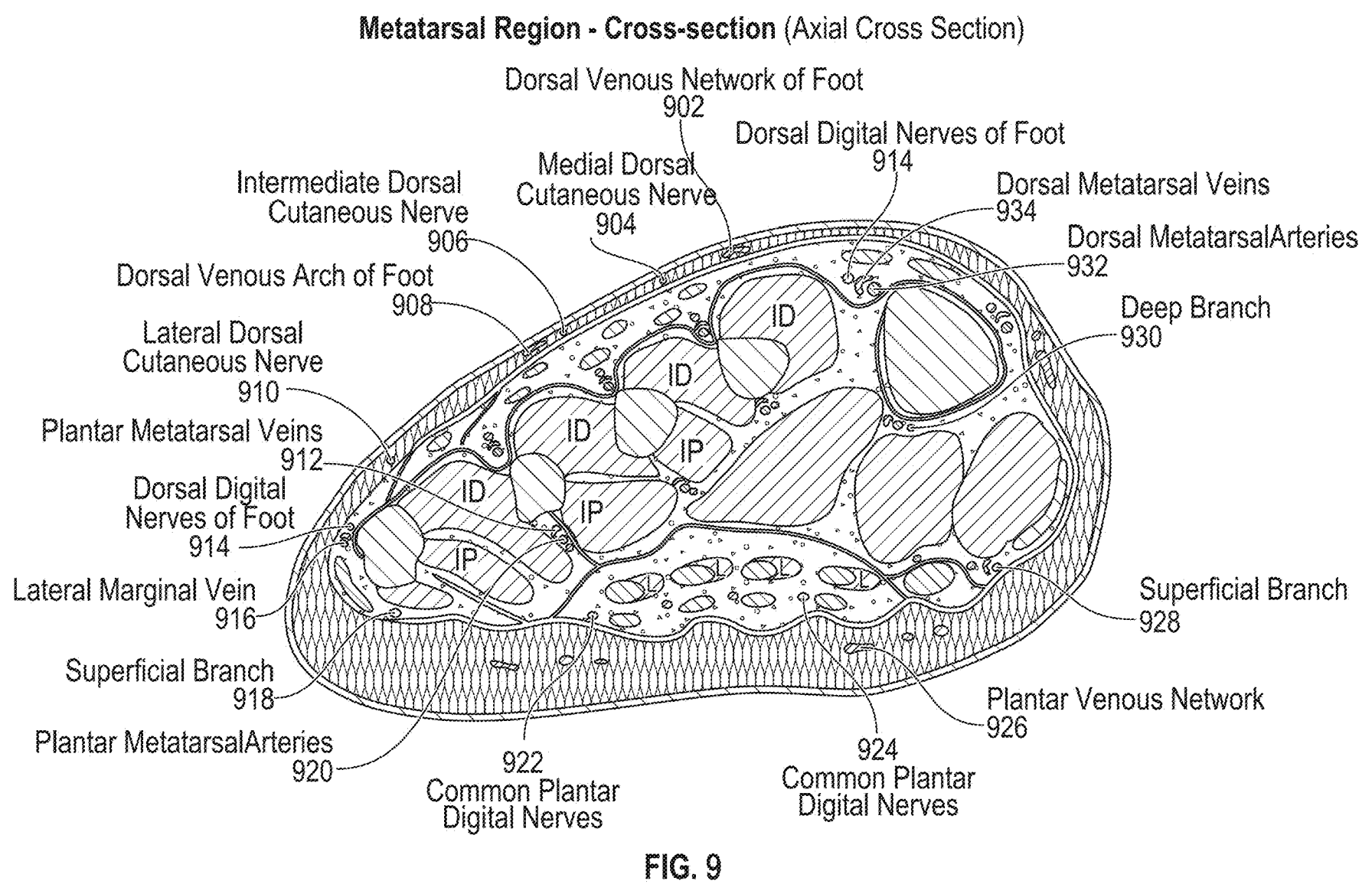

Metatarsal Region - Cross-section (Axial Cross Section)

Dorsal Venous Network of Foot 902

Medial Dorsal Cutaneous Nerve 904

Intermediate Dorsal Cutaneous Nerve 906

Dorsal Venous Arch of Foot 908

Lateral Dorsal Cutaneous Nerve 910

Plantar Metatarsal Veins 912

Dorsal Digital Nerves of Foot 914

Lateral Marginal Vein 916

Superficial Branch 918

Plantar Metatarsal Arteries 920

Dorsal Digital Nerves of Foot 914

Dorsal Metatarsal Veins 934

Dorsal Metatarsal Arteries 932

Deep Branch 930

Superficial Branch 928

Plantar Venous Network 926

Common Plantar Digital Nerves 924

Common Plantar Digital Nerves 922

FIG. 9

Cryodevice in Vein.
Temp Probe at 1 cm

Pre Ablation Venogram.
Marker at Center of
Ballon

Venogram During Ablation,
Ice Ball Occlusive at 30s

Post Ablation Venogram
with Patency of Vein

Cryoneurolysis Studies, Animal Lab Acute Pathology Findings

| Feature | Nov 19, 2024 Study | Mar 4, 2025 Study |
| --- | --- | --- |
| Balloon Cooling Performance | Achieved -17°C at 10 mm | Achieved -108°C at 5 mm and -46°C at 10 mm from balloon |
| Nerve Effect | Acute axonal swelling observed | More pronounced acute axonal swelling + irregular sheath |
| Vascular Integrity | Veins remained open; minimal intravascular clot noted | Veins remained open; no DVT observed on post-procedure US |
| Arterial Involvement | No damage to adjacent artery, confirmed on US & histology | No damage to adjacent artery, confirmed on US & histology |
| Muscle Response | Acute muscle necrosis localized near treatment zone | More extensive muscle necrosis noted in some areas |
| Skin Involvement | Epithelial and adnexal necrosis (localized) | Diffuse dermal coagulative necrosis with microhemorrhage |
| Histologic Indicators of Efficacy | Axonal swelling, mild venous wall changes | Vein wall edema, necrosis, hemorrhage, axonal disruption |
| Safety Findings | Normal nerve morphology outside treatment zone | Consistent preservation of nerve structure outside target zone |
| Summary of Treatment Effectiveness | Demonstrated basic feasibility | Confirmed robust cryoneurolysis effect at deeper temp zones |

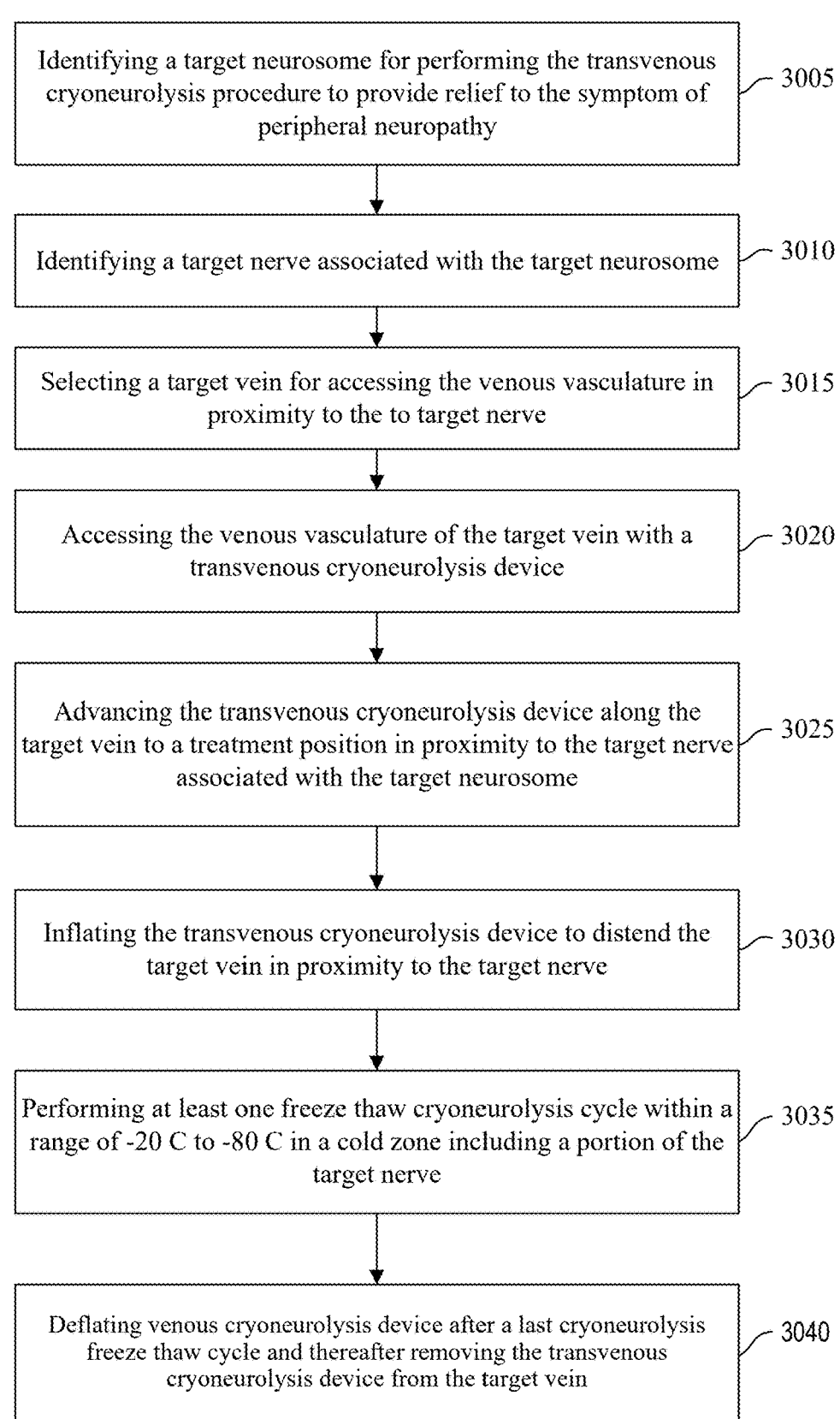

Identifying a target neurosome for performing the transvenous cryoneurolysis procedure to provide relief to the symptom of peripheral neuropathy ⟋ 3005

Identifying a target nerve associated with the target neurosome ⟋ 3010

Selecting a target vein for accessing the venous vasculature in proximity to the to target nerve ⟋ 3015

Accessing the venous vasculature of the target vein with a transvenous cryoneurolysis device ⟋ 3020

Advancing the transvenous cryoneurolysis device along the target vein to a treatment position in proximity to the target nerve associated with the target neurosome ⟋ 3025

Inflating the transvenous cryoneurolysis device to distend the target vein in proximity to the target nerve ⟋ 3030

Performing at least one freeze thaw cryoneurolysis cycle within a range of -20 C to -80 C in a cold zone including a portion of the target nerve ⟋ 3035

Deflating venous cryoneurolysis device after a last cryoneurolysis freeze thaw cycle and thereafter removing the transvenous cryoneurolysis device from the target vein ⟋ 3040

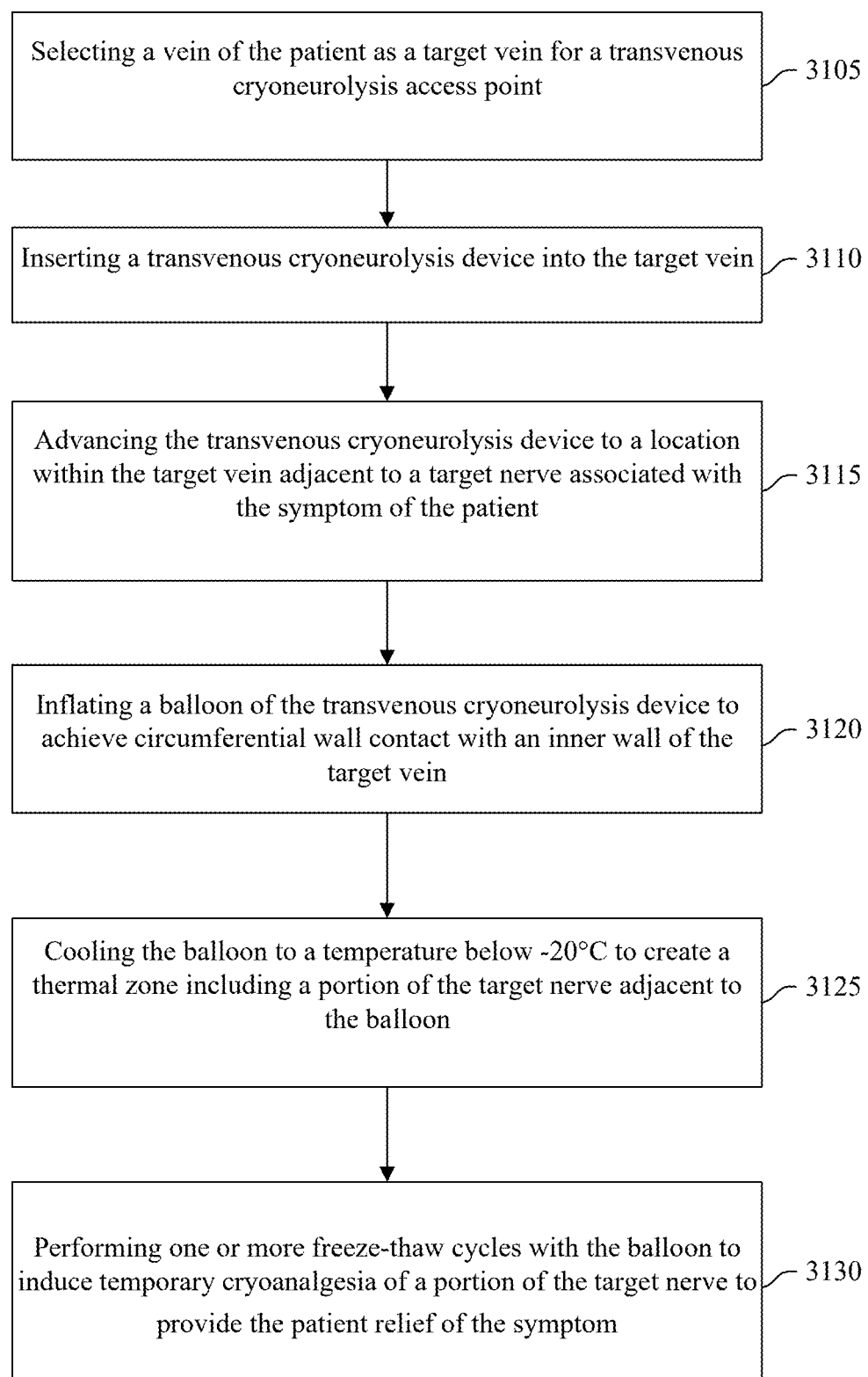

Selecting a vein of the patient as a target vein for a transvenous cryoneurolysis access point   3105

Inserting a transvenous cryoneurolysis device into the target vein   3110

Advancing the transvenous cryoneurolysis device to a location within the target vein adjacent to a target nerve associated with the symptom of the patient   3115

Inflating a balloon of the transvenous cryoneurolysis device to achieve circumferential wall contact with an inner wall of the target vein   3120

Cooling the balloon to a temperature below -20°C to create a thermal zone including a portion of the target nerve adjacent to the balloon   3125

Performing one or more freeze-thaw cycles with the balloon to induce temporary cryoanalgesia of a portion of the target nerve to provide the patient relief of the symptom   3130

FIG. 31

Lower Extremity Nerve/Vein Target Map with Anatomical Access Landmarks

| Target Nerve | Access Vein | Anatomic Location | Access Landmark | Distance to Nerve | Treatment/Therapy |
|---|---|---|---|---|---|
| Saphenous Nerve | Great Saphenous Vein | Medial ankle and leg | ~3 cm anterior to medial malleolus | <5 mm (parallel course) | Ideal for sensory DPN |
| Tibial Nerve | Posterior Tibial Vein | Posterior to medial malleolus | Just behind the medial malleolus, ~2 cm above foot arch | ~3-5 mm | Target for plantar foot symptoms |
| Deep Peroneal Nerve | Anterior Tibial Vein | Anterior ankle/leg | Midway between tibia and fibula at the ankle, lateral to extensor hallucis longus | ~5-7 mm | For webspace/foot dorsum symptoms |
| Common Peroneal Nerve | Small Saphenous tributaries | Lateral lower leg/fibular head | ~4 cm below fibular head, slightly posterior | ~5-10 mm | Dorsal foot coverage |
| Superficial Peroneal | Small Saphenous (tributary) | Lateral mid-shin to ankle | Midpoint between anterior tibia and lateral malleolus | ~5-10 mm | Covers dorsum of foot |
| Medial Plantar Nerve | Medial Plantar Vein | Medial plantar arch | Plantar surface, ~2 cm behind the ball of the foot | ~3 mm | Plantar DPN target |
| Lateral Plantar Nerve | Lateral Plantar Vein | Lateral sole of foot | ~3 cm behind the base of the 5th toe | ~3-5 mm | Also covers heel |
| Sural Nerve | Small Saphenous Vein | Posterior/lateral ankle | Just posterior to lateral malleolus, ~3 cm up | ~2-3 mm | For heel/lateral foot symptoms |

FIG. 32

Pelvic Nerve/Vein Target Map with Anatomical Access Landmarks

| Target Nerve | Access Vein | Anatomic Location | Access Landmark | Distance to Nerve | Treatment/Therapy |
|---|---|---|---|---|---|
| Pudendal Nerve | Internal Pudendal Vein | Courses through Alcock's canal along ischial spine | Transgluteal or perineal access ~2 cm medial to ischial tuberosity | ~3–5 mm | Key target for chronic pelvic pain, pudendal neuralgia |
| Ilioinguinal Nerve | External Iliac Vein tributary | Near inguinal ligament and pubic ramus | 2–3 cm superior to inguinal ligament near pubic symphysis | ~5 mm | Sensory neuropathy post-hernia repair |
| Genitofemoral Nerve | External Iliac Vein | Runs on anterior psoas, near femoral vein | Access via common femoral vein ~1 cm below inguinal ligament | ~5–7 mm | Often implicated in post-op inguinodynia |
| Obturator Nerve | Obturator Vein | Courses through obturator canal | Medial thigh approach ~3–4 cm inferior and medial to pubic tubercle | ~3 mm | Possible target for pelvic myofascial pain syndrome |
| Posterior Femoral Cutaneous Nerve | Inferior Gluteal Vein | Posterior to ischial tuberosity | Lateral to gluteal fold, ~5 cm deep | ~5–10 mm | Sensory nerve affecting posterior thigh and perineum |
| Pelvic Plexus / Inferior Hypogastric Plexus | Internal Iliac Vein branches | Anterior to sacrum, lateral to rectum | Via presacral or transrectal approach (advanced application) | ~7–10 mm | Target for advanced pelvic pain, endometriosis pain |

FIG. 33

Upper Extremity Nerve/Vein Target Map with Anatomical Access Landmarks

| Target Nerve | Access Vein | Anatomic Location | Access Landmark | Distance to Nerve | Treatment/Therapy |
|---|---|---|---|---|---|
| Median Nerve | Cephalic Vein (forearm) | Runs with brachial artery, anterior forearm | ~4 cm distal to antecubital fossa, radial side of forearm | ~3–5 mm | For carpal tunnel, forearm neuropathy |
| Ulnar Nerve | Basilic Vein (proximal forearm) | Posterior to medial epicondyle | Access ~2 cm distal to medial epicondyle on posterior-medial elbow | ~2–4 mm | For cubital tunnel syndrome |
| Radial Nerve | Cephalic Vein (upper arm) | Spirals around humerus, lateral upper arm | ~6–8 cm above lateral epicondyle along humerus | ~5–8 mm | For radial neuropathy, dorsal hand numbness |
| Musculocutaneous Nerve | Median cubital/cephalic veins | Anterior compartment of upper arm | Access mid-bicep, anterior humerus ~6 cm from shoulder | ~5 mm | For lateral forearm sensory complaints |
| Medial Antebrachial Cutaneous Nerve | Basilic Vein | Medial upper forearm | Medial access ~5 cm below elbow crease | ~3 mm | Pure sensory target for medial forearm pain |

FIG. 34

Head and Neck Nerve/Vein Target Map with Anatomical Access Landmarks

| Target Nerve | Access Vein | Anatomic Location | Access Landmark | Distance to Nerve | Treatment/Therapy |
|---|---|---|---|---|---|
| Greater Occipital Nerve | External Jugular Vein branches | Posterior scalp, upper cervical region | ~5 cm below occiput along midline or lateral to external occipital protuberance | ~5 mm | For occipital neuralgia |
| Lesser Occipital Nerve | Posterior Auricular Vein | Behind the ear | ~2–3 cm posterior to the pinna along lateral neck | ~3–5 mm | Common in cervicogenic headache |
| Auriculotemporal Nerve | Superficial Temporal Vein | Temporal scalp | Anterior to tragus ~2 cm; aligned with TMJ | ~2–4 mm | Temporal pain, TMJ-related neuralgia |
| Supraorbital Nerve | Supraorbital Vein | Forehead | ~2 cm above eyebrow along supraorbital ridge | ~2 mm | For frontal headache, supraorbital neuralgia |
| Trigeminal Nerve (V3) | Facial vein tributary | Mandibular ramus area | Via buccal or inferior facial vein ~1–2 cm anterior to mandibular angle | ~5–8 mm | Advanced use for facial neuralgia |
| Greater Auricular Nerve | External Jugular Vein | Lateral neck, over sternocleidomastoid | Midway between ear lobe and clavicle | ~3–6 mm | For post-surgical neck pain |

FIG. 35

| Target Nerve | Clinical Indication or symptom | Anatomical landmarks or target vein access |
|---|---|---|
| Pudendal Nerve | Perineal pain, pelvic pain, sexual dysfunction | Target in pudendal canal adjacent to vein paths |
| Ganglion Impar | Pelvic and perineal cancer pain | Target anterior to sacrococcygeal ligament |
| Celiac Plexus | Upper abdominal cancer pain (e.g., pancreatic) | Target near celiac artery |
| Splanchnic Nerves | Visceral pain (upper abdominal) | Target lateral to vertebral bodies (T11–T12) |
| Aorticorenal Plexus | Flank pain (renal cancer) | Target around renal artery region |
| Intercostal Nerves | Rib fracture pain, post-thoracotomy pain | Subcostal access |
| Ilioinguinal/Iliohypogastric | Inguinal neuralgia (post-hernia repair) | Medial to anterior superior iliac spine |
| Genitofemoral Nerve | Groin pain (post-surgical) | Anteromedial to iliopsoas at anterior inferior iliac spine |
| Obturator Nerve | Medial thigh cancer pain or neuralgia | Medial to acetabulum |
| Sciatic Nerve (proximal) | Tumor neuralgia, stump pain after amputation | Deep to gluteus or popliteal fossa |
| Deep Peroneal (Fibular) Nerve | Distal leg neuropathic pain | Popliteal or distal fibular access |
| Sural Nerve | Lateral foot/ankle pain post-trauma or surgery | Posterior to fibula above ankle |
| Saphenous Nerve | Medial leg/knee pain (post-CABG or ortho surgery) | Adjacent to saphenous vein |
| Lateral Femoral Cutaneous Nerve | Lateral thigh neuropathy (meralgia paresthetica) | Target anterior iliac bone |
| Posterior Femoral Cutaneous Nerve | Posterior thigh neuropathy | Posterior to ischium |
| Geniculate Nerves (Knee) | Knee osteoarthritis pain | Superior medial, superior lateral, inferior medial genicular nerves (± inferior lateral if necessary) |
| Vagus Nerve (posterior trunk) | Obesity management (experimental) | Near esophagus (likely not initial target for Nervana) |
| Ulnar Nerve | Upper extremity neuropathic pain | Near medial elbow |

FIG. 36

TRANSVENOUS CRYONEUROLYSIS SYSTEM, DEVICES AND METHODS

CLAIM OF PRIORITY

This application is related to U.S. Provisional Patent Application Ser. No. 63/639,516 entitled "Venous Cryogenic Neuromodulation Devices and Methods," filed on Apr. 26, 2024.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This application relates to venous cryoneurolysis devices and methods, in particular those performed via access from the venous vasculature. In particular aspects, there are balloon-based cryoneurolysis systems configured for transvenous access adjacent to peripheral nerves, enabling controlled, predictable nerve treatment using prescribed cryogenic lesion lengths without the need for advanced imaging modalities such as computed tomography.

BACKGROUND

There is an ongoing opioid crisis in the United States. Between 1999 and 2021, the number of deaths due to drug overdose increased sixfold. Over 75% of these drug overdoses involve an opioid. The rise in opioid use driving this crisis is due to a number of factors, including: lobbying by pharmaceutical companies, inadequate regulation, over prescription of opioids, and increased use of illegal or synthetic opioids. Due to the highly addictive nature of opioids, any misuse can result in dependencies that are difficult to resolve. The problem is such that at least 60 million people worldwide are struggling with opioid addiction.

Neuropathic pain is one driver of opioid use. Neuropathic pain is caused by damage to nerves, and can have many underlying causes. While not generally recommended as a primary option for treating acute neuropathy, opioids are commonly prescribed for treating chronic neuropathic pain; between 2014 and 2018, opioids were the most prescribed first-line treatment for diabetic peripheral neuropathy despite the fact that other treatments were recommended. Unfortunately, opioid use can contribute to the development of peripheral neuropathy. This creates a vicious cycle of patients turning to opioids to get relief, but as a result experiencing more pain, which then drives greater opioid use. During the opioid boom, many chronic neuropathy patients became addicted to, and dependent on, opioids such as oxycodone. As the medical field has sought to correct course by reducing opioid use, these patients have been left suffering from withdrawal or turning to other sources of drugs. A major factor driving the widespread use of opioids to treat neuropathic pain is that current options for treating neuropathy are not sufficient. According to Dr. Daniela Salvemini, a pharmacology and physiology scientist whose research is supported through the NIH HEAL Initiative, neuropathic pain is "the worst pain to have [because] we don't have many options to treat patients, and our options have limited efficacy and many side effects".

Current non-opioid treatments for peripheral neuropathy fall into a few categories. These include transcutaneous electrical nerve stimulation (TENS), light therapy, pneumatic compression devices, and spinal cord stimulators (SCS). The specifics of these approaches have a variety of shortcomings in both results achieved, requirement for special equipment as well as operator training. The most prominent and critical shortcoming of current treatment options—which is shared by all of them—is that they primarily offer pain management, with limited or no treatment of the underlying cause of neuropathy. As a result, there remains a clear need for improved treatment options and equipment that overcomes these remaining challenges.

Cryoneurolysis is a minimally invasive technique that applies cold temperatures to nerves to achieve temporary interruption of nerve conduction, offering therapeutic benefits for pain management and other clinical applications. However, conventional traditional approaches to cryoneurolysis rely on percutaneous needle placement perpendicular or oblique to the nerve. The conventional techniques often result in undesired variability in lesion size, depth, and nerve recovery timelines. Further, the conventional methods usually require advanced medical imaging such as computed tomography for accurate targeting, increasing procedural complexity and cost.

Furthermore, existing cryoneurolysis techniques often create small, irregular treatment zones that are difficult to standardize, and may result in inconsistent outcomes or unintended injury to adjacent tissues. In view of these shortcomings, there remains a need for improved cryoneurolysis systems and techniques that enable reproducible lesion creation over a defined longitudinal length, allows for predictable nerve healing, minimizes adjacent tissue injury, and reduces reliance on costly capital equipment.

SUMMARY OF THE DISCLOSURE

In one aspect, there is provided a method of performing a transvenous cryoneurolysis procedure to treat a symptom of peripheral neuropathy in a patient. The method may include identifying a target neurosome for performing the transvenous cryoneurolysis procedure to provide relief to the symptom of peripheral neuropathy, then identifying a target nerve associated with the target neurosome. Thereafter, there is a step of selecting a target vein for accessing the venous vasculature in proximity to the target nerve and accessing the venous vasculature of the target vein with a transvenous cryoneurolysis device. Next, there is a step of advancing the transvenous cryoneurolysis device along the target vein to a treatment position in proximity to the target nerve associated with the target neurosome followed by inflating the transvenous cryoneurolysis device to distend the target vein in proximity to the target nerve. At this point, there is a process of performing at least one freeze-thaw cryoneurolysis cycle within a range of –20° C. to –80° C. in a cold zone including a portion of the target nerve. Once the desired number of cycles is completed there is a step of deflating the transvenous cryoneurolysis device after a last cryoneurolysis freeze-thaw cycle then removing the transvenous cryoneurolysis device from the target vein. The method may include variations such as when accessing the venous vasculature of the target vein is selected such that the advancing the transvenous cryoneurolysis device along the target vein to a treatment position includes antegrade motion of the transvenous cryoneurolysis device along the target vein. Additionally, there may be a step where the inflating the transvenous cryoneurolysis device step reduces the distance between the transvenous cryoneurolysis device and a portion of the target nerve in proximity to the target vein. In one implementation, the after the inflating step the target vein has been distended from 2 mm to 12 mm. Still further, there may also be a step of maintaining a distending force on the target vein adjacent to the transvenous cryoneurolysis device during the at least one freeze-thaw cycle. In one implementation, after the performing step an axial cryolesion with a length from 1 cm to 10 cm is formed along the target nerve. In one aspect, the length of the axial cryolesion along the target nerve is related to a length of the inflated portion of the transvenous cryoneurolysis device. The method may be performed where the symptom of peripheral neuropathy is related to a leg, an ankle or a foot of the patient.

In one alternative implementation, the target neurosome includes a portion of the saphenous nerve. In still another implementation, the target vein is the great saphenous vein and the step of accessing the venous vasculature is in proximity to an ankle of the patient. In some implementations, the symptom of peripheral neuropathy is degraded muscle function in the posterior compartment of the leg such as gastrocnemius, soleus, tibialis posterior or the intrinsic foot muscles or sensation to the heel and sole of the foot. In one variation, the target neurosome includes a portion of the tibial nerve. Optionally, the target vein is the posterior tibial vein and the step of accessing the venous vasculature is performed adjacent to an ankle of the patient. In one aspect, the symptom of peripheral neuropathy is deteriorated muscle function or innervation of the muscles of the anterior compartment of the leg responsible for dorsiflexion of the foot and extension of the toes or related to sensation to the web space between the first and second toes or associated with a portion of the dorsal aspect of the foot. In another implementation the target neurosome includes a portion of the Deep Peroneal Nerve. In still another implementation, the target vein is the anterior tibial vein and the step of accessing the venous vasculature is performed adjacent to an ankle. In one aspect, the overall length of the transvenous cryoneurolysis device used to perform the method has an overall length from a handle on a proximal portion of a catheter to the distal most end of the device is less than 30 cm or is 25 cm, or is 20 cm, or is 15 cm. There are some implementations where during the step of performing at least one freeze-thaw cryoneurolysis cycle the length of the catheter shaft of the transvenous cryoneurolysis device proximal to the most proximal portion of the balloon and within the target vein is less than 20 cm.

In yet another aspect of the present invention, there is a method of performing transvenous cryoneurolysis for temporary cryoanalgesia of a symptom of a patient. The method includes a step of selecting a vein of the patient as a target vein for a transvenous cryoneurolysis access point and then inserting a transvenous cryoneurolysis device into the target vein. Then there is a step of advancing the transvenous cryoneurolysis device to a location within the target vein adjacent to a target nerve associated with the symptom of the patient. Once in a desired position, there is a step of inflating a balloon of the transvenous cryoneurolysis device to achieve circumferential wall contact with an inner wall of the target vein and then cooling the balloon to a temperature below −20° C. to create a thermal zone including a portion of the target nerve adjacent to the balloon. Thereafter, depending on desired outcome, there is a process of performing one or more freeze-thaw cycles with the balloon for inducing temporary cryoanalgesia of a portion of the target nerve to provide the patient relief of the symptom.

In one variation, the target vein is one of the great saphenous vein, the posterior tibial vein or the anterior tibial vein. In one implementation, the target nerve is one of a saphenous nerve, a tibial nerve, or a deep peroneal nerve and the symptom of the patient is related to peripheral neuropathy. In one variation, the inserting step is performed at a location in the target vein wherein the distance from the access point in the target vein to the location adjacent to the target nerve is less than 10 cm and the movement of the transvenous cryoneurolysis device from the access point to the location adjacent to the target nerve includes antegrade motion along the target vein. In still another variation, after the advancing step the venous cryoneurolysis device is from 3-7 mm from a portion of the target nerve. Optionally, during the cooling the balloon step a motor fiber and a sensory fiber of the target nerve are within the thermal zone. Still further, during the cooling the balloon step, the thermal zone has a temperature in the range −20° C. to −80° C. at a portion of the target nerve or the thermal zone maintains a temperature to induce Sunderland 2 axonotmesis in sensory fibers of the target nerve. In one specific implementation, the target vein is the great saphenous vein, the target nerve is the saphenous nerve and wherein the inserting step is performed using an access point anatomical landmark that is within 3 cm anterior to the medial malleolus or wherein the target vein is the posterior tibial vein, the target nerve is the tibial nerve and wherein the inserting step is performed using an access point anatomical landmark that is within 2 cm of the arch of the foot just behind the medial malleolus or wherein the target vein is the anterior tibial vein, the target nerve is the common peroneal nerve and wherein the inserting step is performed using an access point anatomical landmark that is midway between the tibia and the fibula at ankle and lateral to the extensor hallucis longus.

In one alternative, the target vein is one of an internal pudendal vein, an external iliac vein tributary or an external iliac vein. Additionally, in a specific implementation, the target nerve is one of a pudendal verve, an ilioinguinal nerve or a genitofemoral nerve and the symptom is related to one or more of a chronic pelvic pain, a pudendal neuralgia, a sensory neuropathy post-hernia repair or a post-operative inguinodynia. In one variation, after the performing step, a cryolesion is formed along the target nerve having a length related to a length of the balloon of the transvenous cryoneurolysis device. There is also an implementation while during the cooling the balloon step a distance from the balloon in the target vein to the target nerve is from 3-7 mm.

Embodiments of the present invention may include a balloon-based transvenous cryoneurolysis device having a handle with a lumen and an exhaust port in communication with the lumen; a catheter shaft having a proximal end and a distal end and a lumen extending from the proximal end to the distal end wherein the proximal end of the catheter terminates within the handle such that the catheter lumen is in communication with the exhaust port; a cryogenic fluid supply line having a proximal end and a distal end and a lumen therebetween; a connector and a seal on the proximal end of the cryogenic fluid supply line; wherein the balloon is adapted and configured for performance of a transvenous cryoneurolysis therapy; an inlet block in fluid communication with the distal terminal end of the cryogenic supply line and within the balloon interior volume, the inlet block having an inlet chamber with a plurality of apertures providing a fluid pathway from the distal end of the cryogenic supply line and the balloon interior volume; and one or more gas outlet apertures providing communication between the balloon interior volume and the exhaust port via the catheter lumen.

In one variation, the balloon-based transvenous cryoneurolysis device has an overall length of less than 30 cm from the connector and seal on the cryogenic liquid supply line to the distal most end of the catheter. In another variation, the balloon-based transvenous cryoneurolysis device during use for performance of a transvenous cryoneurolysis therapy within a target vein less than 30 cm of the catheter shaft proximal to a proximal end of the balloon is within the target vein. In another alternative, the balloon-based transvenous cryoneurolysis device has a balloon with a length of 1 cm, 2 cm, 4 cm, 6 cm, 8 cm, or 10 cm. The length of the balloon is selected such that during use for performance of the transvenous cryoneurolysis therapy within a target vein a desired length of an axial cryolesion is formed on the target nerve. In one variation, the balloon has a length of 10 mm and during use for performance of the venous cryoneurolysis therapy within a target vein the balloon inflates to distend the target vein to a diameter of 5 mm to 12 mm. Still further, during use in the performance of the venous cryoneurolysis therapy within a target vein the balloon inflates to distend the target vein while maintaining a target cryoneurolysis temperature for performance of the venous cryoneurolysis therapy within a target vein. In one variation, in use for performance of the venous cryoneurolysis therapy within a target vein less than 20 cm of the catheter shaft proximal to a proximal end of the balloon is within the target vein and the balloon inflates to distend the target vein to a diameter of 5-9 mm while maintaining a target transvenous cryoneurolysis temperature for performance of the venous cryoneurolysis therapy within a target vein further wherein the target vein is one of a posterior tibial vein, a saphenous vein or a deep peroneal vein and the venous cryoneurolysis therapy is directed to a symptom of peripheral neuropathy in a lower limb or a foot. There is also a variation wherein in use for performance of the venous cryoneurolysis therapy within a target vein the balloon inflates to distend the target vein to a diameter of 5-9 mm while maintaining a target cryoneurolysis temperature to form the axial cryolesion along a length of a saphenous nerve, a tibial nerve or a deep peroneal nerve. In one specific embodiment, the transvenous cryoneurolysis therapy is directed to a symptom of peripheral neuropathy.

In yet another variation, the balloon-based transvenous cryoneurolysis device has an overall length of less than 80 cm from the connector and seal on the cryogenic supply line to the distal most end of the catheter. In one aspect, the balloon-based transvenous cryoneurolysis device in use for performance of the venous cryoneurolysis therapy within a target vein less than 20 cm of the catheter shaft proximal to a proximal end of the balloon is within the target vein or when in use for performance of the venous cryoneurolysis therapy within a target vein less than 15 cm of the catheter shaft proximal to a proximal end of the balloon is within the target vein. In still other alternative implementations, the balloon-based transvenous cryoneurolysis when used for performance of the venous cryoneurolysis therapy within a target vein the balloon inflates to distend the target vein to a diameter of 5-9 mm while maintaining a target cryoneurolysis temperature for performance of the venous cryoneurolysis therapy within a target vein further wherein the target vein is one of a posterior tibial vein, a saphenous vein or a deep peroneal vein and the venous cryoneurolysis therapy is directed to symptoms of diabetic neuropathy in a lower limb or a foot. In another implementation, the balloon-based transvenous cryoneurolysis device when used in use for performance of a transvenous cryoneurolysis therapy within a target vein the balloon inflates to distend the target vein to provide a cold zone at a target nerve within a range of −20° C. to −80° C. In some embodiments, an interior wall of the balloon coupled to an outer wall at the distal end of the catheter such that the interior volume of the balloon is in communication with the lumen of the catheter. Alternatively, an exterior wall of the balloon is coupled to an inner wall at the distal end of the catheter such that the interior volume of the balloon is in communication with the lumen of the catheter. In one implementation, there is also a container of liquid nitrogen pressurized to 30 psi to 100 psi, the container is coupled to a connector and a seal on the proximal end of the cryogenic liquid supply line.

In one aspect, there is provided a method of performing selective transvenous cryoneurolysis. The method includes examining a patient and assessing one or more symptoms of neuropathic pain and then identifying one or more neurosomes to target for venous cryoneurolysis to provide relief to at least one of the one or more symptoms of neuropathic pain. Next, there is a process of identifying a target nerve associated with the identified neurosome and then selecting a target vein for accessing the venous vasculature in proximity to the target nerve. At this point, there is a step of accessing the venous vasculature via the target vein to allow antegrade motion along the target vein with a venous cryoneurolysis device and then advancing the venous cryoneurolysis device in an antegrade direction along the target vein to a treatment position in proximity to the nerve associated with the identified neurosome. Once in the desired position, there is a process for inflating the venous cryoneurolysis device to distend the target vein in proximity to the target nerve and reduce the distance between the venous cryoneurolysis device and a portion of the target nerve in proximity to the venous cryoneurolysis device. This is followed by performing at least one freeze-thaw cryoneurolysis cycle within a range of −20° C. to −80° C. on the target nerve and then deflating venous cryoneurolysis device after the last cryoneurolysis cycle. Next, there is a step of removing the venous cryoneurolysis device from the target vein.

In other embodiments, the method is performed on an additional nerve to target within the identified neurosome. Additionally, there may also be a step of maintaining a distending force on the target vein adjacent to the cryoneurolysis device during one freeze-thaw cycle or during each freeze-thaw cycle. In another aspect, wherein the examining and assessing step leads to a determination that the neuropathic pain is related to one or more of sensation to the medial side of the leg, ankle, and foot. In one aspect, a targeted neurosome includes a portion of the saphenous nerve. Still further, the target vein is the great saphenous vein and an access point is adjacent to an ankle. In still another aspect, wherein the examining and assessing step leads to a determination of muscle function in the posterior compartment of the leg such as gastrocnemius, soleus, tibialis posterior or the intrinsic foot muscles or sensation to the heel and sole of the foot. In one embodiment, a targeted neurosome includes a portion of the tibial nerve. There may also be implementations where the target vein is the posterior tibial vein and an access point is adjacent to an ankle. In yet another specific implementation, the examining and assessing step leads to a determination of muscle function or innervation of the muscles of the anterior compartment of the leg responsible for dorsiflexion of the foot and extension of the toes or related to sensation to the web space between the first and second toes or associated with a portion of the dorsal aspect of the foot. In another aspect, a targeted neurosome includes a portion of the Deep Peroneal (Fibular) Nerve. In other embodiments, the target vein is the anterior tibial vein and an access point is adjacent to an ankle. In still other variations, the overall length of a venous cryoneuroly-sis device used to perform the method has an overall length from a handle on the proximal end to the distal most end that is less than 30 cm or is 25 cm, or is 20 cm, or is 15 cm or is 10 cm.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompa-nying drawings of which:

FIG. 1 is an exemplary method of performing transvenous selective cryoneurolysis for peripheral neuropathic pain.

FIG. 2A is a dorsal view 200A of the foot showing the location of the target nerves detailed above.

FIG. 2B is a plantar view 200B of the foot of FIG. 2A also showing the location of the target nerves.

FIG. 7 is an axial cross-section of the ankle in FIG. 6 showing locations of the target nerves and venous pathways.

FIG. 8 is an axial cross-section of the lower leg showing locations of the target nerves and venous pathways.

FIG. 9 is an axial cross-section of the metatarsal region of the foot showing locations of the target nerves and venous pathways.

FIG. 29 illustrates the results of the cryoneurolysis studies and the Animal Lab Acute Pathology Findings.

FIG. 30 is a flow chart of a method for performing a venous access cryoneurolysis procedure to treat neuropathic pain or diabetic neuropathy in a patient.

FIG. 31 is a flow chart of a method of performing venous cryoneurolysis for reversible cryoanalgesia of peripheral neuropathic pain in a lower extremity of a patient.

FIG. 32 illustrates a table showing a Lower Extremity Nerve/Vein Target Map with Access Landmarks.

FIG. 33 illustrates a table showing a Pelvic Nerve/Vein Target Map with Anatomical Access Landmarks.

FIG. 34 is a table showing an Upper Extremity Nerve/ Vein Target Map with Anatomical Access Landmarks.

FIG. 35 is a table showing a Head and Neck Nerve/Vein Target Map with Anatomical Access Landmarks.

FIG. 36 is a table showing a variety of different target nerves and clinical indications.

DETAILED DESCRIPTION

Figure 3A:
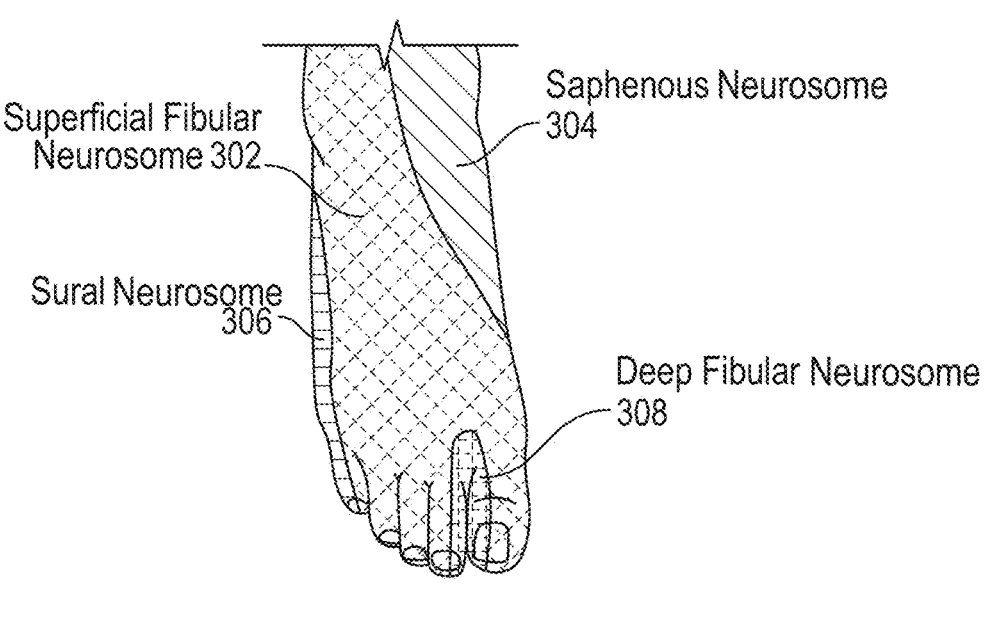
FIG. 3A is a dorsal view 300A of the foot of FIG. 2A also showing the location of the neurosomes of the target nerves.

Embodiments of the transvenous cryoneurolysis catheter and methods of use described herein may be utilized to temporarily and/or permanently relieve pain from peripheral neuropathy by treating the underlying cause of pain. In certain embodiments, the methods and devices may be used to provide relief to individuals suffering from peripheral neuropathy and nerve disorders. In one aspect, the inventive devices and methods are based on the proven science of cryoneurolysis as may be applied as described herein for one or both or combinations to block pain and as well as result in nerve regeneration and restored function.

Despite these benefits, cryoneurolysis is not routinely used for chronic pain management and investigation into its potential for treating peripheral neuropathy is in its infancy. A potential barrier for the widespread use of cryoneurolysis therapy for peripheral neuropathy is that current conven-tional approaches for percutaneous cryoablation are highly dependent on availability of adequate imaging modalities and the skill of the operator. As a result, conventional therapies are limited to a small portion of subspecialty interventional physicians with access to high cost imaging equipment, including CT scans.

In contrast, the devices and methods described herein take a fundamentally different approach to treating neuropathic pain with cryoneurolysis by developing a transvenous device. In one specific implementation, there is a cryoneu-rolysis device adapted and configured for accessing neural targets via the venous vasculature. It is believed that such an approach safely ablates the peripheral nerves causing neuropathy, resulting in pain alleviation and enabling nerve regeneration over time. As a result, it is believed that the devices and methods described herein may take advantage of the regenerative properties of cryoneurolysis to provide permanent relief from nerve pain with no risk of addiction. Additionally, the treatment approach only requires low-cost capital equipment that is readily available in the hospital outpatient or physician office settings, and the procedure can be performed by physicians across a broad range of specialties that frequently encounter these patients. As a result, the devices and methods described herein provide an enabling technology and simple approach compared to conventional systems. Advantageously, these differences have the potential to offer reliable and durable treatment of peripheral neuropathy, and to increase access to care not only for patients suffering from opioid use, but also for others that so desperately need it.

In one embodiment, there is provided a non-implantable, temporally and single session treatment modality that relieves pain while stimulating nerve regeneration. In one aspect, the device is adapted and configured for performing transvenous cryoneurolysis for symptoms of peripheral neuropathy. While not desiring to be bound by theory, it is believed that the methods and devices described herein provide an approach to delivering cryoneurolysis therapy that eliminates the skill-based outcome variation and increases access to care for a wider range of patient classifications. While desiring not to be bound by theory, it is believed that the novel transvenous approach provides therapeutic levels of cooling in the nerves immediately adjacent to the access veins.

The primary shortcoming of current therapies is their failure to effectively treat the underlying cause of peripheral neuropathy. Instead, current systems and methods merely attempt to provide pain management. In contrast, the methods and devices described herein enable transvenous cryoneurolysis in an approach that is holistic, treating neuropathic pain while also promoting nerve regeneration. In one embodiment, cryoneurolysis refers to the use of extreme cold to modulate the sensory fibers of peripheral nerves to relieve the pain associated with peripheral neuropathy while avoiding nerve ablation. One benefit of this approach is that the underlying architecture of the nerve is left intact allowing for neuro-regeneration. This stands in sharp contrast to some conventional therapies which instead lead to complete and permanent destruction of the nerve and do not allow for regeneration. More particularly, in the context of peripheral nerves, it is believed that cryoneurolysis may be employed to relieve chronic pain, particularly when other methods prove ineffective. In one exemplary embodiment when cryoablation is applied to peripheral nerves it is called cryoneurolysis and this is distinct from its use for tumor ablation, for example. In cryoneurolysis, the ablation is often 3 minutes freeze—1 minute thaw—3 minutes freeze of sensory fibers but leaves underlying neuronal structure intact. In contrast, tumor cryoablation has a much longer 8 minute freeze 4 minute thaw 8 minute freeze algorithm which leads to tumor cell death. It is believed that even a short duration 3 minute freeze cycle may be sufficient disruption in nerve function to block pain signals. Additionally, it is believed that following cryoneurolysis, peripheral nerves exhibit a remarkable capacity to regenerate. Unfortunately, due to the complexity of existing systems and methodologies, cryoneurolysis is underutilized for treating peripheral neuropathy. Currently, cryoneurolysis is performed via a percutaneous approach using CT or ultrasound imaging guidance for probe placement. Such a procedure requires a high skill level. As a result, the patient outcomes are very technique, operator, and facility/equipment dependent.

In contrast, the inventive devices and methods of the transvenous cryoneurolysis system can be easily tracked through the vasculature to a site adjacent to the distribution of nerve pain. In some specific implementations, the veins of the lower extremities are used to provide access to the cryoneurolysis site. In specific examples, the veins around the ankle and foot may be used to provide access for the system. More particularly, the exemplary catheterization sites include the great saphenous, anterior tibial veins, or posterior tibial veins at the ankle. Each of these veins is selected because each one is easy to access through routine techniques performed by many physicians. In one aspect, the inventive approach takes advantage of the "natural anatomical highways" of the neurovascular bundle and removes the technique dependency of percutaneous probe placement under advanced imaging guidance for a successful result.

In one implementation, the devices and methods described herein are used for individuals with peripheral neuropathy. Globally, an estimated 2.4% of the population is impacted by peripheral nerve disorders, with this prevalence increasing to 8% among older demographic groups. In the U.S., the prevalence of peripheral neuropathy is notably higher in specific groups. For instance, among adults with diabetes, the prevalence is estimated at 28%. For the general U.S. population aged 40 and above, 13.5% are affected by peripheral neuropathy when assessed by monofilament insensitivity. Within the general U.S. population, the prevalence spans from 1% to 7%, with an increase noted with advancing age. The growth of this market is being driven by the increasing prevalence of diabetes, the aging population, and advances in medical device technology.

In the field of temperature-based therapies, exposure of neural tissue to temperatures of −20° C. to −80° C. cause sensory loss (Sunderland 2 axonotmesis), while colder temperatures of −80° C. to −100° C. cause motor nerve damage. Therefore, in order to increase selectivity of sensory nerves over motor nerves, the methods and devices described herein operate to provide controllable and repeatable cooling to neural target of between −20° C. and −80° C. Based on the diameter of our target veins described herein, embodiments of the cryoneurolysis device may be compatible with 6 F sheaths or smaller.

Advantageously, the methods and devices of the inventive cryoneurolysis system have been adapted and configured based on careful consideration of various target nerves and associated venous access sites. In one aspect, the inflation of a treatment balloon with a cryotherapy or cryoneurolysis fluid is selected to ensure that the access vein is distended so as to ensure the vein wall is urged into apposition with the targeted nerve and that the vein wall thickness is reduced due to the expansion. It is believed that this beneficial combination of an expanded vein aids in thermal transfer and more consistent temperature profiles and clinical results. A range of factors are considered for neural target and venous access, by way of illustration and not limitation: (a) anatomy of the neurovascular bundle in the lower extremities; (b) sensory innervate expected symptom relief; (c) motor innervation of target nerve(s) (if present) and potential side effect/motor weakness (although probe temperature is limited to the higher/sensory range rather than the lower/motor range temperatures; (d) ease of venous access (given target physician operators are familiar/adept at venous access for superficial endovenous ablation using similar technique); (e) length-dependent pattern of peripheral neuropathy, i.e. toes affected first, then feet, then lower legs. Additionally, this factor makes ankle access ideal and requires short ablation probe lengths; (f) blood flow direction and the presence of valves. In one aspect, an antegrade approach (caudal to cranial, in direction of venous blood flow) makes venographic/fluoroscopic visualization easy and obviates the need to navigate venous valves that would present a challenge from a retrograde approach.

In view of the above factors, embodiments of the device and methods will be described with regard to targeting cryoneurolysis therapies using veins as venous pathways to target certain nerves or neurosomes. Advantageously, based on patient exam and symptoms, highly targeted cryoneurolysis treatments of one or more affected nerves can be performed using veins as venous pathways. In one aspect, such an approach is referred to as a "neurosome" concept, similar to the "angiosome" concept used in the treatment of peripheral arterial disease and chronic limb threatening ischemia. In a further aspect, a balloon-based cryoneurolysis system may utilize venous access for cryoneurolysis of targeted analgesia without promoting motor blockage. In a still further aspect, the balloon-based cryoneurolysis system may provide a transvenous cryoneurolysis device and transvenous cryoneurolysis method for performing transvenous cryoneurolysis treatment.

In one aspect, embodiments of the transvenous cryoneurolysis system described herein include an expandable balloon configured for deployment adjacent to a target nerve via a venous structure, such as a target vein. In use, the inflation of the balloon to a nominal diameter is achieved via expansion by a cryogenic fluid which could be a suitable liquid (i.e., liquid nitrogen $LN_2$) or a gas (i.e., Argon). Once in position within the target vein, the inflated balloon forms a cryogenic treatment zone having a prescribed, selectable longitudinal length between, for example, approximately 1 cm and 10 cm. Advantageously, because of the alignment within the neurovascular bundle, the balloon, when expanded, aligns substantially parallel to the target nerve and the operation of the transvenous cryoneurolysis system enables controlled cryogenic injury to the nerve, facilitating predictable axonal regeneration while minimizing injury to adjacent tissues. It is to be appreciated that the use of 'parallel' is to help provide an understanding of the related alignment between the device and target nerve by taking advantage of the naturally occurring alignment and orientation of natural physiological structures. Put another way, parallel as used herein is meant to indicate an approach that is general along the target nerve in contrast to the oblique approach of conventional systems. To be clear, the conventional systems are neither axial nor parallel within the meaning of the inventive system and methods.

In one aspect, the prescribed longitudinal length for lesion formation on the target nerve is selectable from approximately 1 cm, 2 cm, 4 cm, 6 cm, 8 cm, or 10 cm. The desired length of the lesion is proportional to the length of the balloon in the transvenous cryoneurolysis system. It is to be appreciated that the balloon is advanced and navigated through an adjacent target/access vein using ultrasound, fluoroscopy, or a combination thereof. Advantageously, embodiments of the inventive transvenous method may be performed without requiring computed tomography as is necessary in conventional approaches. In another advantageous aspect, inflation of the balloon in the transvenous system simultaneously distends the venous wall toward the target nerve, reducing the distance between the nerve and the balloon surface. In various embodiments, the cryogenic temperatures within a cold zone achieved by the transvenous balloon is maintained between approximately −20° C. and −80° C.

As a result of this improved transvenous balloon system, there are also improved methods for performing cryoneurolysis including advancing a balloon catheter through a venous structure adjacent to a target nerve and then positioning and inflating the balloon to a prescribed longitudinal length. The longitudinal length may be between approximately 1 cm and 10 cm. Optionally, the balloon aligns substantially parallel or longitudinally along to the target nerve. Next, cooling the balloon is achieved by delivery of a cryogenic fluid to create a suitable cold zone to form a cryogenic lesion along the target nerve. One benefit of the use of a more predictable lesion length is that it allows for a predictable nerve regeneration at a known axonal regrowth rate (approximately 1-2 mm per day) while minimizing adjacent tissue injury. As such, the transvenous balloon catheter is advanced through an existing vein—a natural neurovascular structure. Balloon expansion and the behavior of a vein wall allow for compression of soft tissues overlying the target area during balloon inflation to reduce nerve-to-vein distance and protect the skin from cryogenic injury.

For example, FIG. 1 illustrates an exemplary method 100 for performing selective venous cryoneurolysis using a transvenous approach to access one or more targeted nerves of one or one or more selected neurosomes.

First, at 105, there is a step of examining a patient and assessing one or more symptoms of neuropathic pain.

Next, at 110, there is a step of identifying one or more neurosomes to target for venous cryoneurolysis to provide relief to at least one of the one or more symptoms of neuropathic pain.

Next, at 115, there is a step of identifying a target nerve associated with the identified neurosome.

Next, at 120, there is a step of selecting a target vein for accessing the venous vasculature in proximity to the target nerve.

Thereafter, there is at step 125, the performing the various steps for accessing the venous vasculature via the target vein to allow antegrade motion along the target vein with a venous cryoneurolysis device.

As shown above, once the venous vascular is accessed, the next step 130 is performed for advancing the venous cryoneurolysis device in an antegrade direction along the target vein to a treatment position in proximity to the nerve associated with the identified neurosome.

The exemplary method continues by next inflating the venous cryoneurolysis device to distend the target vein in proximity to the target nerve and reduce the distance between the venous cryoneurolysis device and a portion of the target nerve in proximity to the venous cryoneurolysis device (step 135).

With the venous cryoneurolysis device in position, there is a step of performing at least one freeze-thaw cryoneurolysis cycle within a range of −20° C. to −80° C. on the target nerve (step 140).

Optionally, there may be a step of maintaining a distending force on the target vein adjacent to the cryoneurolysis device during one freeze-thaw cycle or during each freeze-thaw cycle (step 145).

Thereafter, after the last cryoneurolysis cycle, there is a step of deflating the venous cryoneurolysis device. It is to be appreciated that deflating in this step broadly encompasses deflating any treatment balloons whether used to distend the target vein or to deliver cryoneurolysis, including removal of any cryotherapy or cryoneurolysis fluid or gas or residual after last cryoneurolysis cycle (step 150).

Next, there is a step of removing the venous cryoneurolysis device from the target vein (step 155).

There may also be a decision point in the therapy of determining whether any additional nerves to target within identified neurosome. It may be the case that the neuropathic pain presents in a region of the body between or across one or more of the regions (such as identified in FIGS. 2A and 2B). (step 160)

If the answer at step 160 is YES, then perform a step to select the next nerve target, and target vein (step 165). Thereafter, repeat steps 110-160 for each symptom, target nerve or target neurosome.

If the answer at step 160 is No, then complete venous cryoneurolysis treatment (step 166).

Various embodiments of the balloon-based venous cryoneurolysis system and the venous cryoneurolysis device may be used to advantage in providing for temporary relief of acute and chronic pain and temporary cryoanalgesia to various targeted nerves and neurosomes. The method of providing cryoanalgesia to the targeted nerves and neurosomes may be appreciated with regard to the following examples in the lower extremity of the body. The following figures represent the lower extremity of the body:

FIG. 2A is a dorsal view 200A of the foot showing the location of the target nerves detailed above. FIG. 2B is a plantar view 200B of the foot of FIG. 2A also showing the location of the target nerves.

Figure 3B:
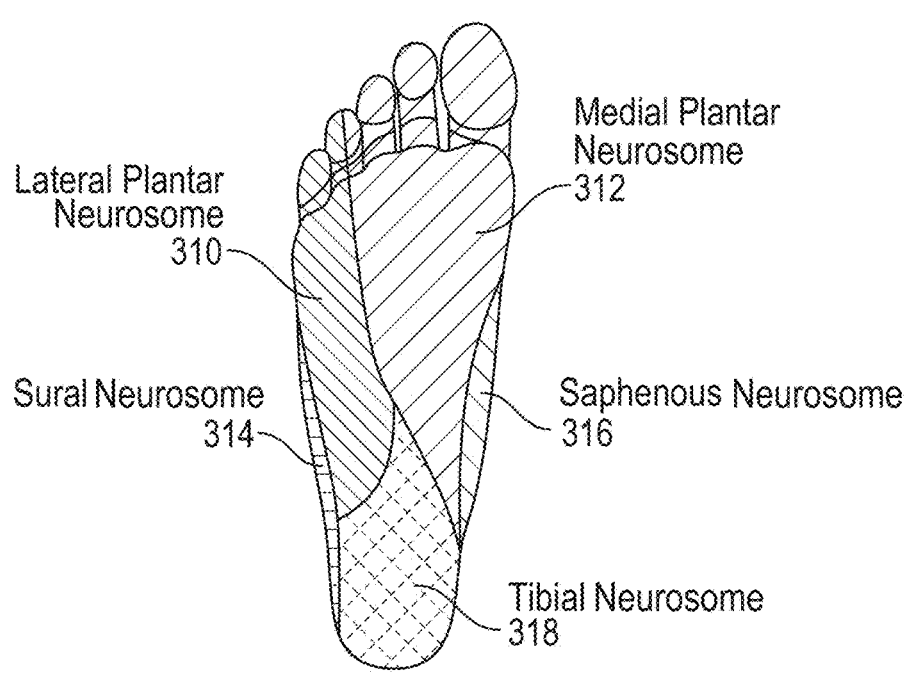
FIG. 3B is a plantar view 300B of the foot of FIG. 2B showing the location of the neurosomes of the target nerves.

FIG. 3A is a dorsal view 300A of the foot of FIG. 2A also showing the location of the neurosomes of the target nerves. FIG. 3B is a plantar view 300B of the foot of FIG. 2B showing the location of the neurosome of the target nerves.

Figure 4A:
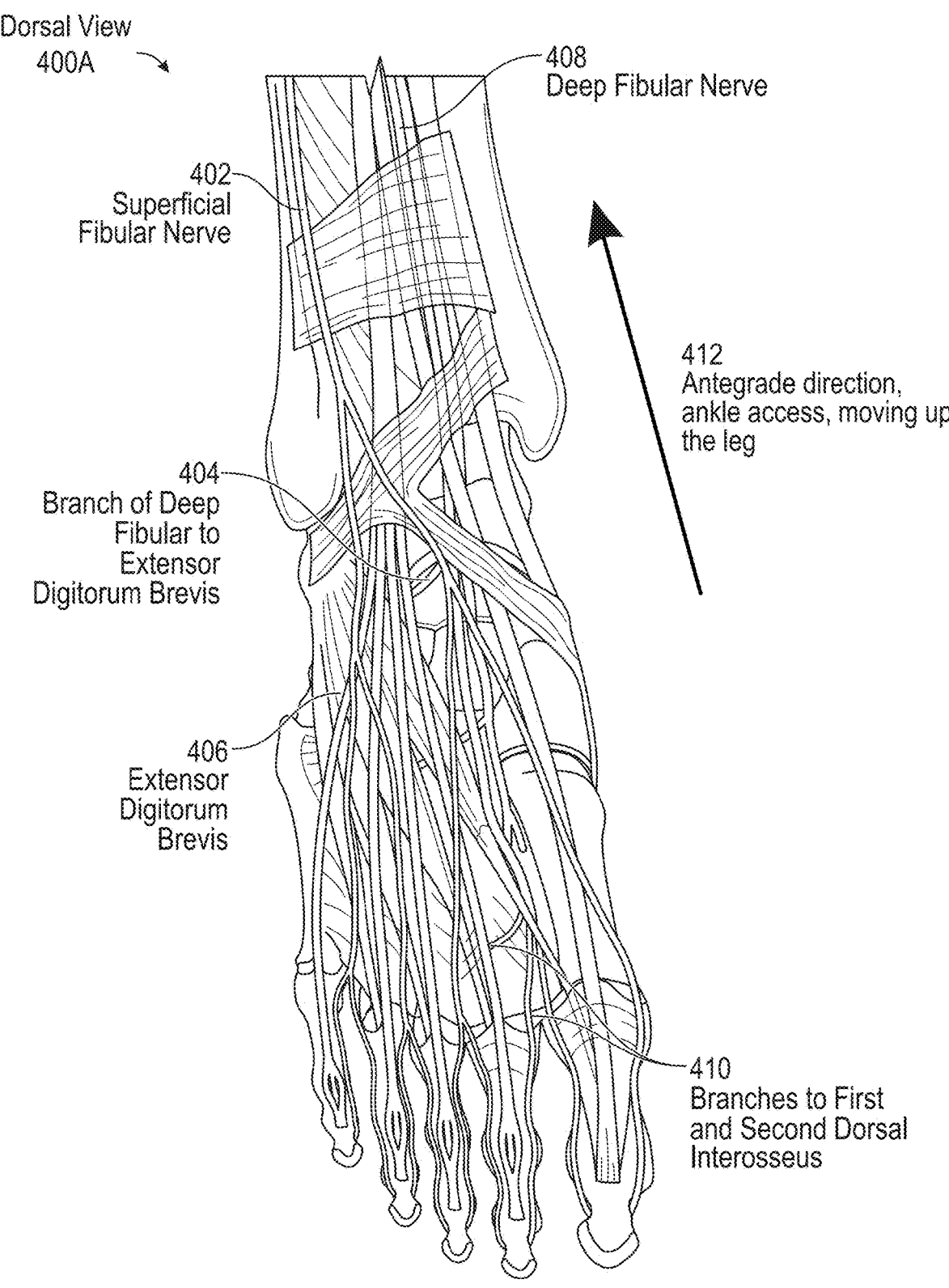
FIG. 4A is an additional dorsal view 400A of the foot showing the location of the target nerves detailed above.
Figure 4B:
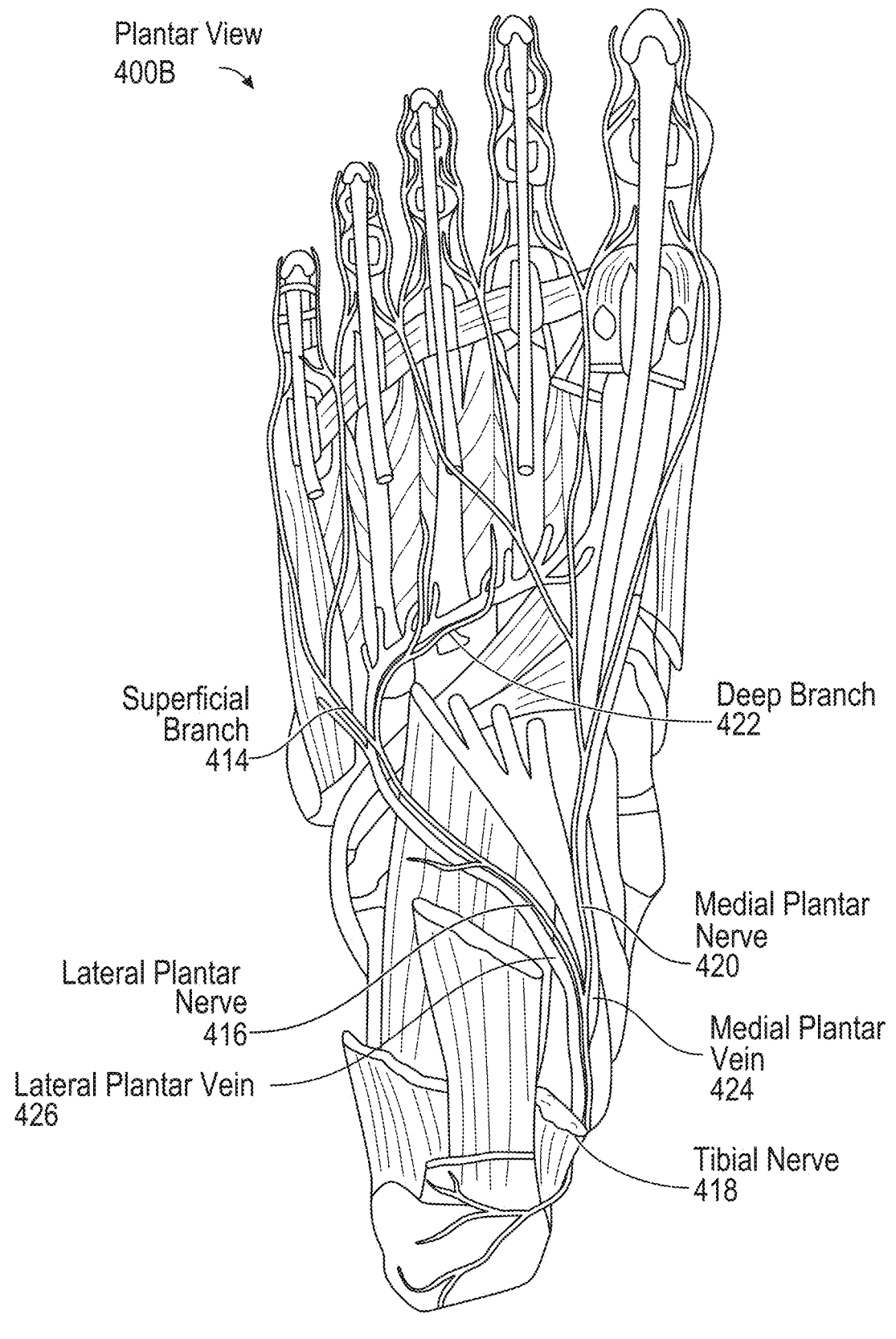
FIG. 4B is a plantar view 400B of the foot of FIG. 4A also showing the location of the target nerves.

FIG. 4A is an additional dorsal view 400A of the foot showing the location of the target nerves detailed above. FIG. 4B is a plantar view 400B of the foot of FIG. 4A also showing the location of the target nerves.

Figure 5:
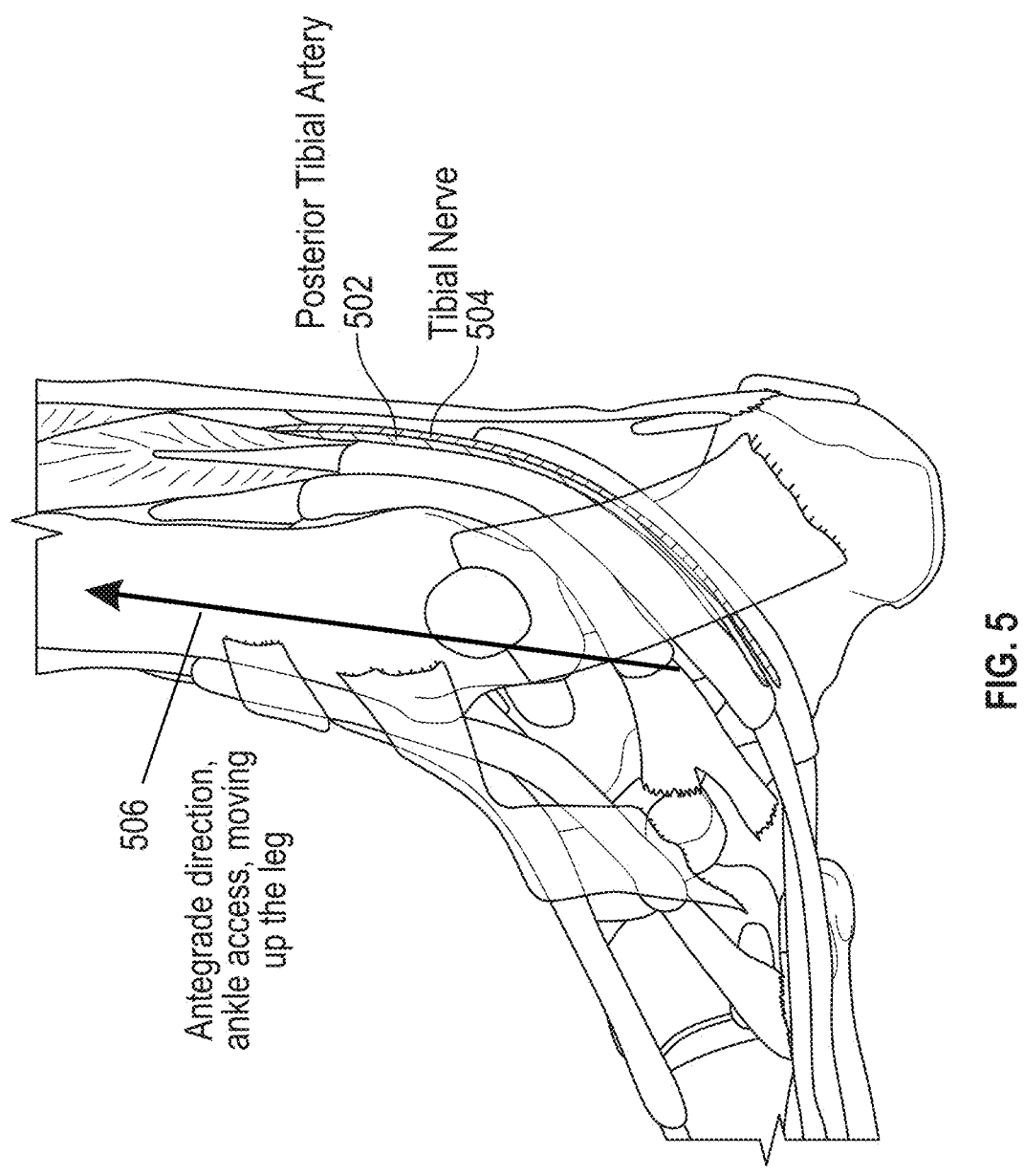
FIG. 5 is a side view of the ankle showing locations of the target nerves.
Figure 6:
FIG. 6 is a posterior view of the ankle of FIG. 5.

FIG. 5 is a side view of the ankle showing locations of the target nerves. FIG. 6 is a posterior view of the ankle of FIG. 5. FIG. 7 is an axial cross-section of the ankle in FIG. 5 showing locations of the target nerves and venous pathways. FIG. 8 is an axial cross-section of the lower leg showing locations of the target nerves and venous pathways.

FIG. 9 is an axial cross-section of the metatarsal region of the foot showing locations of the target nerves and venous pathways.

In order to target the nerves in the lower extremity of the body associated with the anatomy shown in FIGS. 2A, 2B, 3A, 3B, 4A, 4B, 5, 6, 7, 8, and 9 mentioned above, the target nerves may be treated by the balloon-based venous cryoneurolysis system. The balloon-based venous cryoneurolysis system describes a method of providing cryoanalgesia to the targeted nerves and neurosomes which utilizes the appropriate venous access and venous pathways to target the appropriate nerves. Advantageously, the balloon-based venous cryoneurolysis system and its balloon-based venous cryoneurolysis device may be positioned within the target vein adjacent to the target nerve. Further, the balloon-based venous cryoneurolysis device inflates a balloon within the target vein and takes advantage of the elastic properties of the veins to further shorten the distance between the target vein and the target nerve. The following nerves are associated with the anatomy shown in FIGS. 2A, 2B, 3A, 3B, 4A, 4B, 5, 6, 7, 8, and 9:

The Saphenous Nerve:

Target Nerve: Saphenous Nerve—The saphenous nerve runs along the great saphenous vein on the medial aspect of the leg. The saphenous nerve arises from the posterior division of the femoral nerve in the femoral triangle of the upper thigh and travels within the adductor canal (Hunter's canal), alongside the femoral artery and vein, deep to the sartorius muscle. Just before or as it passes through the adductor hiatus, the saphenous nerve exits the canal (without entering the popliteal fossa) and becomes superficial, emerging between the sartorius and gracilis muscles. Finally, the saphenous nerve courses subcutaneously down the medial leg, accompanying the great saphenous vein, passing anterior to the medial malleolus, and terminates in the medial foot and arch. The saphenous nerve is the largest cutaneous branch of the femoral nerve, and the primary sensory nerve of the medial leg and foot. The saphenous neve is purely sensory, with no motor function, and plays a critical role in cutaneous innervation from the anteromedial thigh to the medial malleolus and arch of the foot.

FIG. 2A shows the saphenous nerve 210, FIG. 3A shows the saphenous neurosome 304 of the saphenous nerve 210, FIG. 3B shows the saphenous neurosome 316 of the saphenous nerve 210, FIG. 7 shows the saphenous nerve 720 alongside the great saphenous vein 722, and FIG. 8 shows the saphenous nerve 820 alongside the great saphenous vein 822. Advantageously, the saphenous nerve 210, 720, 820 may be accessed via the great saphenous vein 722, 822.

As can be seen in FIG. 7, there exists a shortened distance between the great saphenous vein 722 and the nearby saphenous nerve 720. As further seen in FIG. 8, there exists a shortened distance between the great saphenous vein 822 and the nearby saphenous nerve 820. The balloon-based venous cryoneurolysis system described takes advantage of the aforementioned short distance and the elastic properties of veins by positioning the balloon-based venous cryoneurolysis device within the great saphenous vein 722, 822 adjacent the saphenous nerve 210, 720, 820. As such, the balloon-based venous cryoneurolysis device may utilize the great saphenous vein 722, 822 as a venous pathway to perform cryoneurolysis according to a freeze-thaw protocol to target the adjacent saphenous nerve 210, 720, 820.

Further, the balloon-based venous cryoneurolysis device may inflate a balloon within the great saphenous vein 722, 822 which distends the great saphenous vein 722, 822 and forms a cold zone. Advantageously, the distending of the great saphenous vein 722, 822 further shortens the distance between the great saphenous vein 722, 822 and the nearby saphenous nerve 720, 820, which ensures that the aforementioned cold zone includes the saphenous nerve 210, 720, 820. This, in turn, allows for the targeting and treatment of the saphenous neurosome 304, 316 associated with the saphenous nerve 210, 720, 820.

The Tibial Nerve:

Target Nerve: The Tibial Nerve—The tibial nerve travels behind the medial malleolus along with the posterior tibial artery and veins. The tibial nerve provides sensation to the medial side of the leg, ankle, and foot. Further, the tibial nerve functions to supply the muscles in the posterior compartment of the leg (e.g., gastrocnemius, soleus, tibialis posterior) and some of the intrinsic foot muscles. Moreover, the tibial nerve also provides sensation to the heel and sole of the foot.

FIG. 2B shows the calcaneal branch of the tibial nerve 214. Moreover, FIGS. 2A and 2B show the lateral plantar nerve 204, the medial plantar nerve 206, and the sural nerve 208, which are branches of the tibial nerve. Further, FIG. 3B shows the posterior tibial neurosome 318 of the tibial nerve, FIG. 4B shows the tibial nerve 418 which bifurcates into the medial plantar nerve 420 and the lateral plantar nerve 416, FIG. 5 shows the tibial nerve 504 alongside the posterior tibial artery 502, FIG. 6 shows the tibial nerve 604 alongside the posterior tibial veins 606, 610 and the posterior tibial artery 608, FIG. 7 shows the posterior tibial nerve 728 alongside each of the posterior tibial veins 724 and the posterior tibial artery 726, and FIG. 8 shows the posterior tibial nerve 828 alongside each of the posterior tibial veins 824 and the posterior tibial artery 826. Advantageously, the tibial nerve 214, 418, 504, 604, 728, 828 may be accessed via the posterior tibial veins 606, 610, 724, 824.

As can be seen in FIG. 6, there exists a shortened distance between the posterior tibial veins 606, 610 and the nearby tibial nerve 604. As also seen in FIG. 7, there exists a shortened distance between the posterior tibial veins 724 and the nearby tibial nerve 728. As further seen in FIG. 8, there exists a shortened distance between the posterior tibial veins 824 and the nearby tibial nerve 828. The balloon-based venous cryoneurolysis system described takes advantage of the aforementioned short distance and the elastic properties of veins by positioning the balloon-based venous cryoneu-rolysis device within the posterior tibial veins 606, 610, 724, 824 adjacent the tibial nerve 214, 418, 504, 604, 728, 828. As such, the balloon-based venous cryoneurolysis device may utilize the posterior tibial veins 606, 610, 724, 824 as a venous pathway to perform cryoneurolysis according to a freeze-thaw protocol to target the adjacent tibial nerve 214, 418, 504, 604, 728, 828.

Further, the balloon-based venous cryoneurolysis device may inflate a balloon within the posterior tibial veins 606, 610, 724, 824 which distends the posterior tibial veins 606, 610, 724, 824 and forms a cold zone. Advantageously, the distending of the posterior tibial veins 606, 610, 724, 824 further shortens the distance between the posterior tibial veins 606, 610, 724, 824 and the nearby tibial nerve 214, 418, 504, 604, 728, 828, which ensures that the aforemen-tioned cold zone includes the tibial nerve 214, 418, 504, 604, 728, 828. This, in turn, allows for the targeting and treatment of the tibial neurosome 318 associated with the tibial nerve 214, 418, 504, 604, 728, 828.

The Deep Peroneal (Fibular) Nerve:

Target Nerve: Deep Peroneal (Fibular) Nerve—The deep peroneal (fibular) nerve accompanies the anterior tibial artery and the anterior tibial vein on the anterior aspect of the leg. The deep peroneal (fibular nerve) innervates the muscles of the anterior compartment of the leg responsible for dorsiflexion of the foot and extension of the toes. Moreover, the deep peroneal (fibular) nerve provides sensation to the web space between the first and second toes and part of the dorsal aspect of the foot.

FIG. 2A shows the deep peroneal (fibular) nerve 202, FIG. 3A shows the deep fibular neurosome 308 of the deep peroneal (fibular) nerve 202, FIG. 4A shows the deep peroneal (fibular) nerve 408, FIG. 7 shows the deep peroneal (fibular) nerve 708 alongside the anterior tibial veins 704 and the dorsal artery of the foot 706, and FIG. 8 shows the deep peroneal (fibular) nerve 804 alongside the anterior tibial veins 808 and the anterior tibial artery 806. Advanta-geously, the deep peroneal (fibular) nerve 202, 708, 804 may be accessed via the anterior tibial veins 704, 808.

As can be seen in FIG. 7, there exists a shortened distance between the anterior tibial veins 704 and the nearby deep peroneal (fibular) nerve 708. As further seen in FIG. 8, there exists a shortened distance between the anterior tibial veins 808 and the nearby deep peroneal (fibular) nerve 804. The balloon-based venous cryoneurolysis system described takes advantage of the aforementioned short distance and the elastic properties of veins by positioning the balloon-based venous cryoneurolysis device within the anterior tibial veins 704, 808 adjacent the deep peroneal (fibular) nerve 202, 708, 804. As such, the balloon-based venous cryoneurolysis device may utilize the anterior tibial veins 704, 808 as a venous pathway to perform cryoneurolysis according to a freeze-thaw protocol to target the adjacent deep peroneal (fibular) nerve 202, 708, 804.

Further, the balloon-based venous cryoneurolysis device may inflate a balloon within the anterior tibial veins 704, 808 which distends the anterior tibial veins 704, 808 and forms a cold zone. Advantageously, the distending of the anterior tibial veins 704, 808 further shortens the distance between the anterior tibial veins 704, 808 and the nearby deep peroneal (fibular) nerve 202, 708, 804, which ensures that the aforementioned cold zone includes the deep peroneal (fibular) nerve 202, 708, 804. This, in turn, allows for the targeting and treatment of the deep fibular neurosome 308 associated with the deep peroneal (fibular) nerve 202, 708, 804.

The Common Peroneal Nerve:

Target Nerve: Common Peroneal Nerve—the common peroneal nerve is a major peripheral nerve of the lower extremity, forming a terminal branch of the sciatic nerve in the posterior thigh. The common peroneal nerve arises in the distal third of the thigh as a division of the sciatic nerve, typically at or near the superior angle of the popliteal fossa. Then, the common peroneal nerve courses laterally along the lateral head of the gastrocnemius muscle and wraps around the fibular neck (also called the fibular head). After winding around the fibular neck, the common peroneal nerve passes deep to the fibularis longus muscle and bifur-cates into the superficial peroneal nerve 212 and the deep peroneal nerve 202, shown in FIG. 2A. Further, the common peroneal nerve provides motor innervation to the short head of the biceps femoris, the peroneus longus and brevis (via superficial peroneal nerve 212), and the tibialis anterior, extensor digitorum longus, extensor hallucis longus, and peroneus tertius (via the deep peroneal nerve 202). Advan-tageously, the common peroneal nerve may be accessed via the small saphenous (tributary) vein or short saphenous vein.

As can be seen in FIG. 7, there exists a small saphenous (tributary) vein 716 or short saphenous vein 716. As further seen in FIG. 8, there exists a small saphenous (tributary) vein 818 or short saphenous vein 818. The small saphenous (tributary) vein 716, 818 and the common peroneal nerve have a close and proximal anatomical relationship, particu-larly in the posterolateral aspect of the knee at the popliteal fossa and proximal calf. The balloon-based venous cryoneu-rolysis system described takes advantage of this anatomical closeness and proximity and the elastic properties of veins by positioning the balloon-based venous cryoneurolysis device within the small saphenous (tributary) vein 716, 818 adjacent the common peroneal nerve. As such, the balloon-based cryoneurolysis device may utilize the small saphenous (tributary) vein 716, 818 as a venous pathway to perform cryoneurolysis according to a freeze-thaw protocol to target the adjacent common peroneal nerve.

Further, the balloon-based venous cryoneurolysis device may inflate a balloon within the small saphenous (tributary) vein 716, 818 which distends the small saphenous (tributary) vein 716, 818 and forms a cold zone. Advantageously, the distending of the small saphenous (tributary) vein 716, 818 further shortens the distance between the small saphenous (tributary) vein 716, 818 and the nearby common peroneal nerve, which ensures that the aforementioned cold zone includes the common peroneal nerve. This, in turn, allows for the targeting and treatment of the neurosome associated with the common peroneal nerve.

The Superficial Peroneal (Fibular) Nerve:

Target Nerve: Superficial Common Peroneal Nerve—the superficial peroneal (fibular) nerve is a terminal branch of the common peroneal nerve. The superficial peroneal (fibular) nerve provides motor innervation to the lateral compartment of the leg, specifically the fibularis longus and the fibularis brevis. Also, the superficial peroneal (fibular) nerve provides sensory innervation to much of the dorsum of the foot, specifically the lower anterolateral leg, most of the dorsum of the foot (excluding the first web space and lateral fifth toe), and the dorsal surfaces of the toes via the dorsal digital nerves.

FIG. 2A shows the superficial peroneal (fibular) nerve 212, FIG. 3A shows the superficial peroneal (fibular) neurosome 302 of the superficial peroneal (fibular) nerve 212, FIG. 4A shows the superficial peroneal (fibular) nerve 402, FIG. 4B shows the superficial peroneal (fibular) nerve 414, and FIG. 8 shows the superficial peroneal (fibular) nerve 802. Advantageously, the superficial peroneal (fibular) nerve 212, 402, 414, 802 may be accessed via the small saphenous (tributary) vein or short saphenous vein.

As can be seen in FIG. 7, there exists a small saphenous (tributary) vein 716 or short saphenous vein 716. As further seen in FIG. 8, there exists a small saphenous (tributary) vein 818 or short saphenous vein 818. The small saphenous (tributary) vein 716, 818 and the superficial peroneal (fibular) nerve 212, 402, 414, 802 do come into proximity in the distal leg. The balloon-based venous cryoneurolysis system described takes advantage of this anatomical closeness and proximity and the elastic properties of veins by positioning the balloon-based venous cryoneurolysis device within the small saphenous (tributary) vein 716, 818 in close proximity to the superficial peroneal (fibular) nerve 212, 402, 414, 802. As such, the balloon-based cryoneurolysis device may utilize the small saphenous (tributary) vein 716, 818 as a venous pathway to perform cryoneurolysis according to a freeze-thaw protocol to target the adjacent superficial peroneal (fibular) nerve 212, 402, 414, 802.

Further, the balloon-based venous cryoneurolysis device may inflate a balloon within the small saphenous (tributary) vein 716, 818 which distends the small saphenous (tributary) vein 716, 818 and forms a cold zone. Advantageously, the distending of the small saphenous (tributary) vein 716, 818 shortens the distance between the small saphenous (tributary) vein 716, 818 and the nearby superficial peroneal (fibular) nerve 212, 402, 414, 802, which ensures that the aforementioned cold zone includes the superficial peroneal (fibular) nerve 212, 402, 414, 802. This, in turn, allows for the targeting and treatment of the superficial peroneal (fibular) neurosome 302 associated with the superficial peroneal (fibular) nerve 212, 402, 414, 802.

The Medial Plantar Nerve:

Target Nerve: Medial Plantar Nerve—the medial plantar nerve is the larger terminal branch of the tibial nerve, arising in the medial ankle following its passage through the tarsal tunnel. The medial plantar nerve provides motor and sensory innervation to the medial plantar aspect of the foot, including the hallux and first three toes. FIG. 2B shows the medial plantar nerve 206, FIG. 3B shows the medial plantar neurosome 312, and FIG. 4B shows the medial plantar nerve 420 bifurcating from the tibial nerve 418. Advantageously, the medial plantar nerve 206, 420 may be accessed via the medial plantar vein 424.

Indeed, the medial plantar nerve 206, 420 and the medial plantar vein 424 are part of the medial plantar neurovascular bundle, which also includes the medial plantar artery. As such, the medial plantar nerve 206, 420 and the medial plantar vein 424 travel in close proximity within the deep plantar foot, as shown in FIG. 4B. The balloon-based venous cryoneurolysis system described takes advantage of this anatomical closeness and proximity and the elastic properties of veins by positioning the balloon-based venous cryoneurolysis device within the medial plantar vein 424 adjacent the medial plantar nerve 206, 420. As such, the balloon-based cryoneurolysis device may utilize the medial plantar vein 424 as a venous pathway to perform cryoneurolysis according to a freeze-thaw protocol to target the adjacent medial plantar nerve 206, 420.

Further, the balloon-based venous cryoneurolysis device may inflate a balloon within the medial plantar vein 424 which distends the medial plantar vein 424 and forms a cold zone. Advantageously, the distending of the medial plantar vein 424 shortens the distance between the medial plantar vein 424 and the nearby medial plantar nerve 206, 420, which ensures that the aforementioned cold zone includes the medial plantar nerve 206, 420. This, in turn, allows for the targeting and treatment of the medial plantar neurosome 312 associated with the medial plantar nerve 206, 420.

The Lateral Plantar Nerve:

Target Nerve: Lateral Plantar Nerve—the lateral plantar nerve is the smaller terminal branch of the tibial nerve, arising within the tarsal tunnel and coursing along the lateral aspect of the plantar foot. The lateral plantar nerve provides motor innervation to the majority of the intrinsic foot muscles and sensory innervation to the lateral sole and lateral toes. FIG. 2B shows the lateral plantar nerve 204, FIG. 3B shows the lateral plantar neurosome 310, and FIG. 4B shows the lateral plantar nerve 416 bifurcating from the tibial nerve 418. Advantageously, the lateral plantar nerve 204, 416 may be accessed via the lateral plantar vein 426.

Indeed, the lateral plantar nerve 204, 416 and the lateral plantar vein 426 are part of the lateral plantar neurovascular bundle, which also includes the lateral plantar artery. As such, the lateral plantar nerve 204, 416 and the lateral plantar vein 426 travel in close proximity within the deep plantar foot, as shown in FIG. 4B. The balloon-based venous cryoneurolysis system described takes advantage of this anatomical closeness and proximity and the elastic properties of veins by positioning the balloon-based venous cryoneurolysis device within the lateral plantar vein 426 adjacent the lateral plantar nerve 204, 416. As such, the balloon-based cryoneurolysis device may utilize the lateral plantar vein 426 as a venous pathway to perform cryoneurolysis according to a freeze-thaw protocol to target the adjacent lateral plantar nerve 204, 416.

Further, the balloon-based venous cryoneurolysis device may inflate a balloon within the lateral plantar vein 426 which distends the lateral plantar vein 426 and forms a cold zone. Advantageously, the distending of the lateral plantar vein 426 shortens the distance between the lateral plantar vein 426 and the nearby lateral plantar nerve 204, 416, which ensures that the aforementioned cold zone includes the lateral plantar nerve 204, 416. This, in turn, allows for the targeting and treatment of the lateral plantar neurosome 310 associated with the lateral plantar nerve 204, 416.

The Sural Nerve:

Target Nerve: The Sural Nerve—The sural nerve is located in the lower leg and foot and provides sensation to the lateral aspects of the foot, ankle, and lower leg. FIG. 2A shows the sural nerve 208, FIG. 3A shows the sural neurosome 306, FIG. 3B shows the sural neurosome 314, FIG. 7 shows the sural nerve 718 alongside the small saphenous vein 716 or the short saphenous vein 716, and FIG. 8 shows the sural nerve 816 alongside the small saphenous vein 818 or the short saphenous vein 818. Advantageously, the sural nerve 208, 718, 816 may be accessed via the small saphenous vein 716, 818.

As shown in FIG. 7, there exists a shortened distance between the small saphenous vein 716 and the nearby sural nerve 718. As further seen in FIG. 8, there exists a shortened distance between the small saphenous vein 818 and the nearby sural nerve 816. The balloon-based venous cryoneurolysis system described takes advantage of the aforementioned short distance and the elastic properties of veins by positioning the balloon-based venous cryoneurolysis device within the small saphenous vein 716, 718 adjacent the sural nerve 208, 718, 816. As such, the balloon-based venous cryoneurolysis device may utilize the small saphenous vein 716, 818 as a venous pathway to perform cryoneurolysis according to a freeze-thaw protocol to target the adjacent sural nerve 208, 718, 816.

Further, the balloon-based venous cryoneurolysis device may inflate a balloon within the small saphenous vein 716, 818 which distends the small saphenous vein 716, 818 and forms a cold zone. Advantageously, the distending of the small saphenous vein 716, 818 further shortens the distance between the small saphenous vein 716, 818 and the nearby sural nerve 718, 816, which ensures that the aforementioned cold zone includes the sural nerve 208, 718, 816. This, in turn, allows for the targeting and treatment of the sural neurosome 306, 314 associated with the sural nerve 208, 718, 816.

The Medial Dorsal Cutaneous Nerve:

Target Nerve: The Medial Dorsal Cutaneous Nerve—The medial dorsal cutaneous nerve is a distal sensory branch of the superficial peroneal (fibular) nerve, arising at approximately the distal third of the anterolateral leg, where the superficial peroneal nerve perforates the deep crural fascia. The medial dorsal cutaneous nerve traverses the anteromedial aspect of the ankle joint, typically passing anterior to the lateral malleolus, and courses dorsally over the medial dorsum of the foot. The medial dorsal cutaneous nerve provides cutaneous innervation to the medial side of the dorsum of the foot, excluding the first interdigital web space. Further, the medial dorsal cutaneous nerve also provides cutaneous innervation to the dorsal surface of the great toe, and the adjacent sides of the second and third toes. FIG. 9 shows the medial dorsal cutaneous nerve 904 alongside the dorsal venous network of the foot 902. Advantageously, the medial dorsal cutaneous nerve 904 may be accessed via the dorsal venous network of the foot 902.

As shown in FIG. 9, there exists a shortened distance between the dorsal venous network of the foot 902 and the nearby medial dorsal cutaneous nerve 904. As such, the balloon-based venous cryoneurolysis device may utilize the venous network of the foot 902 as a venous pathway to perform cryoneurolysis according to a freeze-thaw protocol to target the adjacent medial dorsal cutaneous nerve 904.

Further, the balloon-based venous cryoneurolysis device may inflate a balloon within the venous network of the foot 902 which distends the venous network of the foot 902 and forms a cold zone. Advantageously, the distending of the venous network of the foot 902 further shortens the distance between the venous network of the foot 902 and the nearby medial dorsal cutaneous nerve 904, which ensures that the aforementioned cold zone includes the medial dorsal cutaneous nerve 904. This, in turn, allows for the targeting and treatment of the neurosome associated with the medial dorsal cutaneous nerve 904.

The Intermediate Dorsal Cutaneous Nerve:

Target Nerve: The Intermediate Dorsal Cutaneous Nerve—The intermediate dorsal cutaneous nerve is a lateral terminal branch of the superficial peroneal (fibular) nerve, typically bifurcating from the parent nerve at the anterolateral aspect of the distal third of the leg, just proximal to the ankle joint. The intermediate dorsal cutaneous nerve provides cutaneous sensory innervation to the dorsal surfaces of the lateral foot, including the fourth and fifth toes, and the adjacent sides of the third and fourth toes, depending on anatomical variation. FIG. 9 shows the intermediate dorsal cutaneous nerve 906 alongside the dorsal venous arch of the foot 908. Advantageously, the intermediate dorsal cutaneous nerve 906 may be accessed via the dorsal venous arch of the foot 908.

As shown in FIG. 9, there exists a shortened distance between the dorsal venous arch of the foot 908 and the nearby intermediate dorsal cutaneous nerve 906. As such, the balloon-based venous cryoneurolysis device may utilize the dorsal venous arch of the foot 908 as a venous pathway to perform cryoneurolysis according to a freeze-thaw protocol to target the adjacent intermediate dorsal cutaneous nerve 906.

Further, the balloon-based venous cryoneurolysis device may inflate a balloon within the dorsal venous arch of the foot 908 which distends the dorsal venous arch of the foot 908 and forms a cold zone. Advantageously, the distending of the dorsal venous arch of the foot 908 further shortens the distance between the dorsal venous arch of the foot 908 and the nearby intermediate dorsal cutaneous nerve 906, which ensures that the aforementioned cold zone includes the intermediate dorsal cutaneous nerve 906. This, in turn, allows for the targeting and treatment of the neurosome associated with the intermediate dorsal cutaneous nerve 906.

The Common Plantar Digital Nerves:

Target Nerve: The Common Plantar Digital Nerves—the common plantar digital nerves are terminal sensory branches of the medial and lateral plantar nerves, themselves derived from the tibial nerve as it courses through the tarsal tunnel and into the plantar aspect of the foot. The common plantar digital nerves provide cutaneous sensory innervation to the plantar skin of the distal metatarsal region and adjacent toes; further, the common plantar digital nerves supply motor branches to small intrinsic foot muscles (e.g., lumbricals) and articular branches to the metatarsophalangeal joints. FIG. 9 shows the common plantar digital nerves 924 alongside the plantar venous network 926. Advantageously, the common plantar digital nerves 924 may be accessed via the plantar venous network 926.

As shown in FIG. 9, there exists a shortened distance between the plantar venous network 926 and the nearby common plantar digital nerves 924. As such, the balloon-based venous cryoneurolysis device may utilize the plantar venous network 926 as a venous pathway to perform cryoneurolysis according to a freeze-thaw protocol to target the adjacent common plantar digital nerves 924.

Further, the balloon-based venous cryoneurolysis device may inflate a balloon within the plantar venous network 926 which distends the plantar venous network 926 and forms a cold zone. Advantageously, the distending of the plantar venous network 926 further shortens the distance between the plantar venous network 926 and the nearby common plantar digital nerves 924, which ensures that the aforementioned cold zone includes the common plantar digital nerves 924. This, in turn, allows for the targeting and treatment of the neurosome associated with the common plantar digital nerves 924.

The Dorsal Digital Nerves of the Foot:

Target Nerve: The Dorsal Digital Nerves of the Foot—the dorsal digital nerves of the foot are terminal cutaneous branches of the medial and intermediate dorsal cutaneous nerves (from the superficial peroneal nerve), the sural nerve, and the deep peroneal nerve, collectively forming a network of sensory innervation to the dorsal surfaces of the toes. The dorsal digital nerves provide cutaneous sensory innervation to the dorsal skin of the toes, including the adjacent sides of the toes via paired dorsal digital branches, the lateral fifth toe (sural nerve), and the first web space (deep peroneal nerve). FIG. 9 shows the dorsal digital nerves of the foot 914 alongside the lateral marginal vein 916. Further, FIG. 9 shows the dorsal digital nerves of the foot 914 alongside the dorsal metatarsal veins 934 and the dorsal metatarsal arteries 932.

As shown in FIG. 9, there exists a shortened distance between the lateral marginal vein 916 and the nearby dorsal digital nerves of the foot 914. As such, the balloon-based venous cryoneurolysis device may utilize the lateral marginal vein 916 as a venous pathway to perform cryoneurolysis according to a freeze-thaw protocol to target the adjacent dorsal digital nerves of the foot 914.

Further, the balloon-based venous cryoneurolysis device may inflate a balloon within the lateral marginal vein 916 which distends the lateral marginal vein 916 and forms a cold zone. Advantageously, the distending of the lateral marginal vein 916 further shortens the distance between the lateral marginal vein 916 and the nearby dorsal digital nerves of the foot 914, which ensures that the aforementioned cold zone includes the dorsal digital nerves of the foot 914. This, in turn, allows for the targeting and treatment of the neurosome associated with the dorsal digital nerves of the foot 914.

As further shown in FIG. 9, there exists a shortened distance between the dorsal metatarsal veins 934 and the nearby dorsal digital nerves of the foot 914. As such, the balloon-based venous cryoneurolysis device may utilize the dorsal metatarsal veins 934 as a venous pathway to perform cryoneurolysis according to a freeze-thaw protocol to target the adjacent dorsal digital nerves of the foot 914.

Further, the balloon-based venous cryoneurolysis device may inflate a balloon within the dorsal metatarsal veins 934 which distends the dorsal metatarsal veins 934 and forms a cold zone. Advantageously, the distending of the dorsal metatarsal veins 934 further shortens the distance between the dorsal metatarsal veins 934 and the nearby dorsal digital nerves of the foot 914, which ensures that the aforementioned cold zone includes the dorsal digital nerves of the foot 914. This, in turn, allows for the targeting and treatment of the neurosome associated with the dorsal digital nerves of the foot 914.

Figures 10, 11:
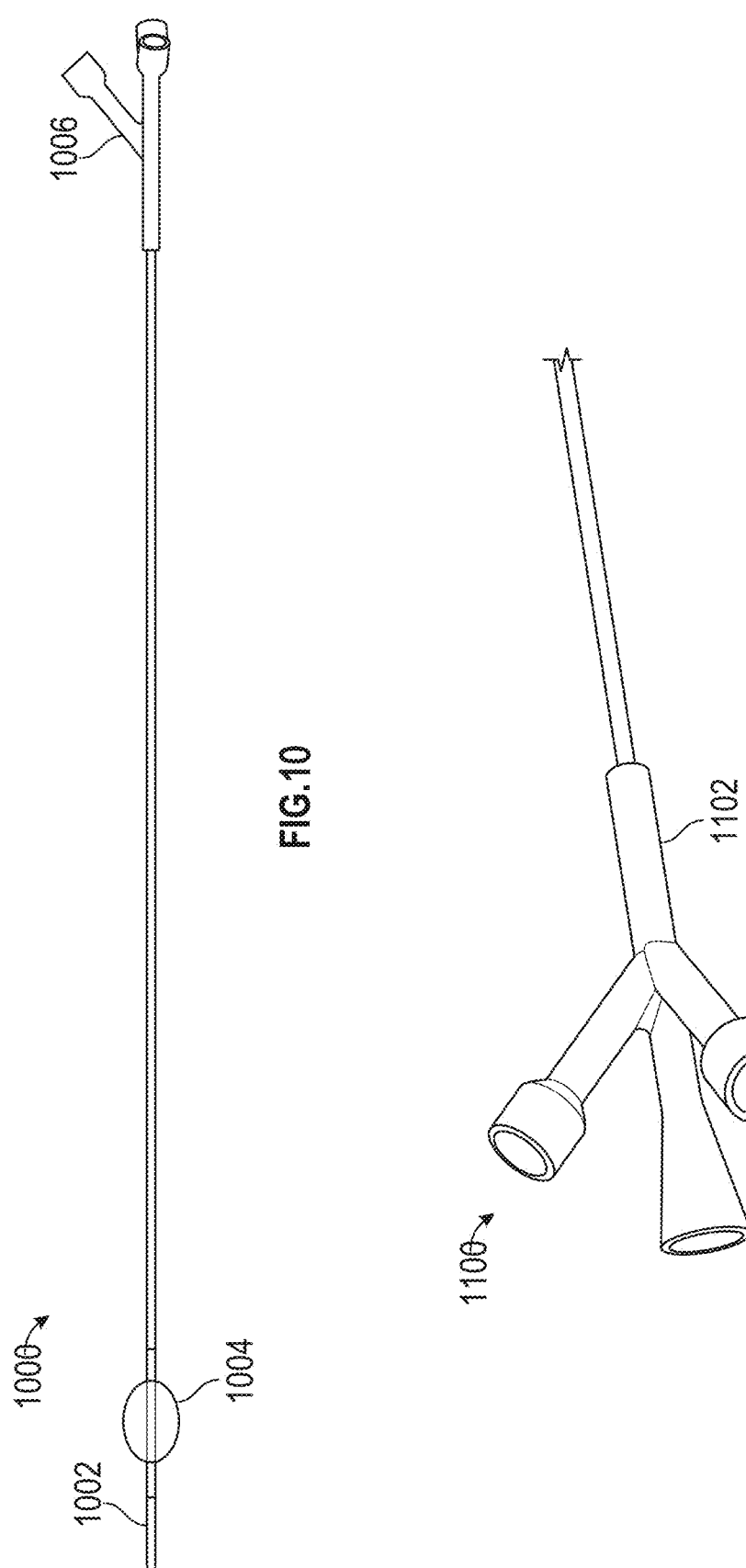
FIG. 10 is a side view of an exemplary embodiment of a balloon-based venous cryoneurolysis catheter system.
FIG. 11 is a perspective view of a proximal end of the catheter system of FIG. 10.

Various embodiments of the balloon-based venous cryoneurolysis system and the venous cryoneurolysis device may be used to advantage in providing for temporary relief of acute and chronic pain and temporary cryoanalgesia to various targeted nerves and neurosomes. Indeed, various systems and devices of providing cryoanalgesia to the targeted nerves and neurosomes may be appreciated with regard to the following venous cryoneurolysis systems and devices:

FIG. 10 is a side view of an exemplary embodiment 1000 of a balloon-based cryoneurolysis system. There are connections 1006 on a proximal end or a handle may be supplied. The distal end includes a treatment balloon 1002 and a temperature sensor 1004 suited for cryoneurolysis. An additional balloon may be added for protection in case of rupture of the cryoneurolysis balloon. In some embodiments, the outer balloon may be used for manipulation of the target vein to distend the vein wall and improve access for the cryoneurolysis device. A thermocouple or temperature sensor is also provided.

FIG. 11 is a perspective view of a proximal end 1100 of the catheter system 1000 in FIG. 10. The attachments 1102 shown can be used for inflation and deflation of the transvenous cryoneurolysis device, a guidewire and the temperature sensor. Further, the attachments 1102 or connector 1102 may also be used to supply liquid nitrogen or any other cryoneurolysis fluid. Additional connections and functionality may be included in other embodiments.

Figures 12, 13:
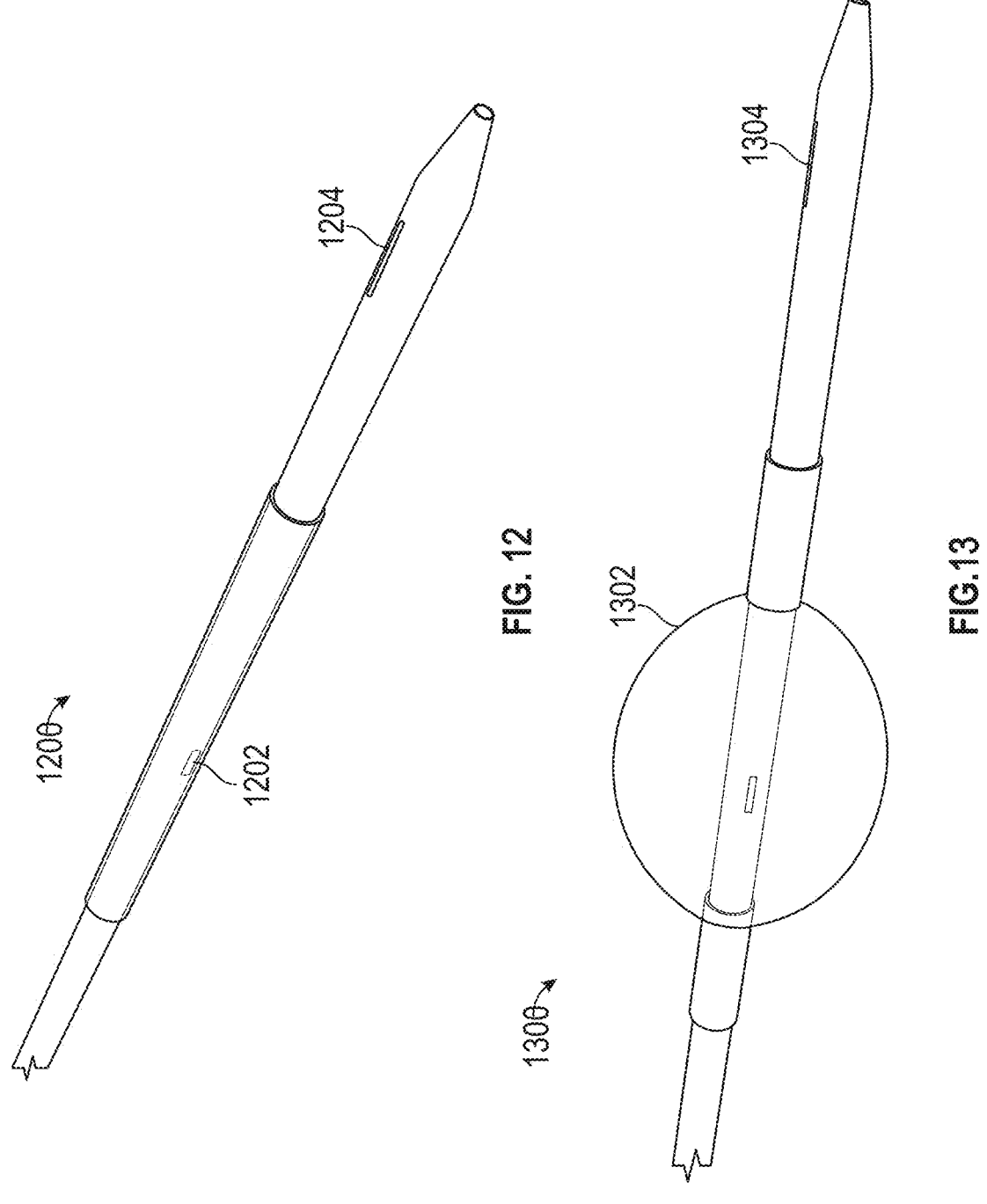
FIG. 12 is a perspective view of the distal end of the catheter system of FIG. 10.
FIG. 13 is a view of the distal end of the catheter system of FIG. 12, with the balloon inflated to a treatment volume with a cryoneurolysis fluid.

FIG. 12 is a perspective view of the distal end 1200 of the catheter system 1000 in FIG. 10. The balloon inflation slot 1202 and the temperature sensor 1204 distal to the balloon are shown in this view.

FIG. 13 is a view of the distal end 1300 of the catheter in FIG. 12 with the balloon 1302 inflated to a treatment volume with a cryotherapy or cryoneurolysis fluid. The temperature sensor 1304 distal to the balloon is also shown.

Figure 14:
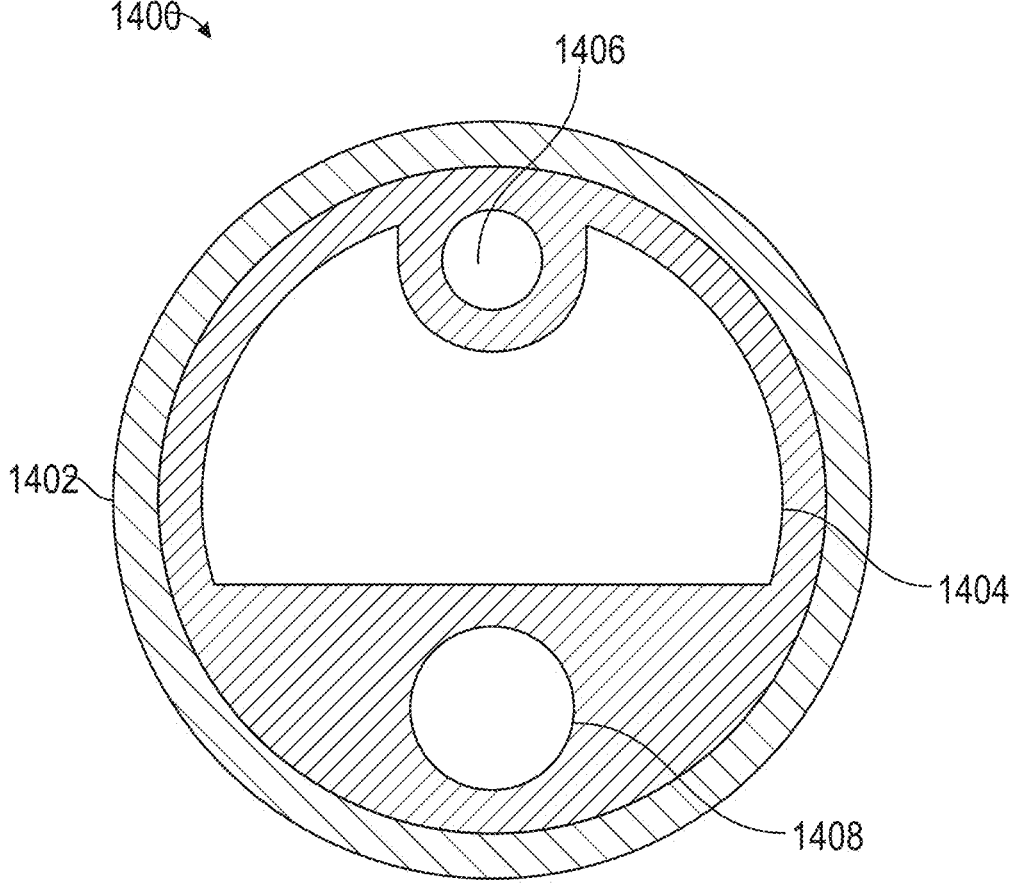
FIG. 14 is a cross-section view of the catheter in FIG. 10.

FIG. 14 is a cross-section view 1400 of the catheter 1000 in FIG. 10. In this view 1400, the aspects of the catheter multi-lumen design are best appreciated. There is one lumen for over-the-wire guidance (OTW), and a second lumen for balloon inflation. Not shown in this view is a second balloon or liner used for additional containment of the cryotherapy or cryoneurolysis fluid. In one aspect, the liner may be fabricated from PTFE or HDPE or other suitable material for cryoneurolysis applications. Additionally, an outer jacket may be composed of a Pebax extrusion. In other variations, there may be the use of TPU if needed to withstand higher pressures. There is also a compliant Pebax balloon or other suitable material located at the distal end of the device. Coolant will be delivered to this balloon. A secondary outer balloon will surround the inner balloon to protect from any rupture during use. Additional aspects of cryoneurolysis device and systems may be appreciated by reference to U.S. Pat. Nos. 3,901,241 and 6,283,959, each of which is incorporated herein by reference in its entirety.

In still other variations, it is to be appreciated that various alternative techniques may be used to achieve cooling of the distal tip. In one aspect, there is provided liquid nitrogen, while in other configurations there may be used nitrous oxide or another similar gas suited to cryoneurolysis treatments. Regardless of approach, there is a temperature sensor provided to measure the temperature at the device tip using a temperature probe. In some embodiments, it is believed that the distal tip will need to reach approximately −70° C. to achieve the desired level of cooling in vivo.

In one embodiment, the method of cryoneurolysis is performed using a balloon therapy device positioned inside of a vein adjacent to a target nerve where the balloon is expanded to distend the wall of the target vein to deliver the cold therapy using a cryoneurolysis procedure with 4×1-4 minute freeze-thaw-freeze cycles. In other embodiments, the length of freeze or thaw cycles may be increased or decreased. The duration of a freeze or thaw cycle may be the same or different, or increased or decreased in subsequent cycles depending on desired therapeutic result in a targeted neurosome.

In an additional aspect, there is a process following a transvenous cryoneurolysis procedure to obtain arteriograms and venograms of all target vessels to assess the patency of the veins used for access, as well as the adjacent arteries within the neurovascular bundle.

In still another alternative embodiment, there is a balloon-based cryoneurolysis device adapted and configured for negotiating the venous system, inflation sufficient to distend the target vein at the target site and to deliver focal cryoneurolysis within the target range of –20° C. to –80° C. In one embodiment, the balloon-based cryoneurolysis device is 30 cm or less in length and has an OD of 1.9 mm so as to be compatible with a 6 F sheath. In some embodiments, while delivering therapy, the device tip will reach –70° C. In still other various embodiments depending upon the specific anatomical situation for a patient or neurosome treatment protocol and other factors such as venous access point and within vein distance to target vein—target nerve location. As a result, in various embodiments, the overall length of a venous cryoneurolysis device used to perform a cryoneu-rolysis method described herein has an overall length from a handle on the proximal end to the distal most end that is less than 30 cm or is 25 cm, or is 20 cm, or is 15 cm or is 10 cm. In some embodiments, the handle may be the connector points at the proximal end of the catheter (see FIG. 11). Additionally or optionally, there may also be a specific handle allowing control of the operation of the transvenous cryoneurolysis device as well as advancement and manipulation within the venous vasculature to deliver therapy in the targeted neurosome.

Figure 15:
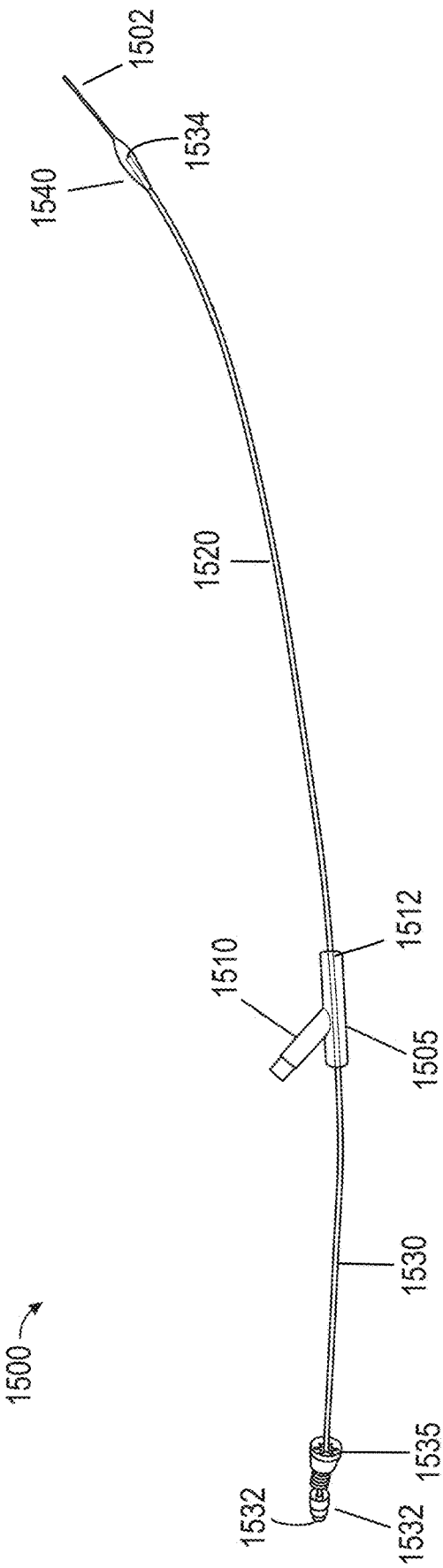
FIG. 15 is a perspective view of a balloon-based cryoneu-rolysis device.
Figure 16:
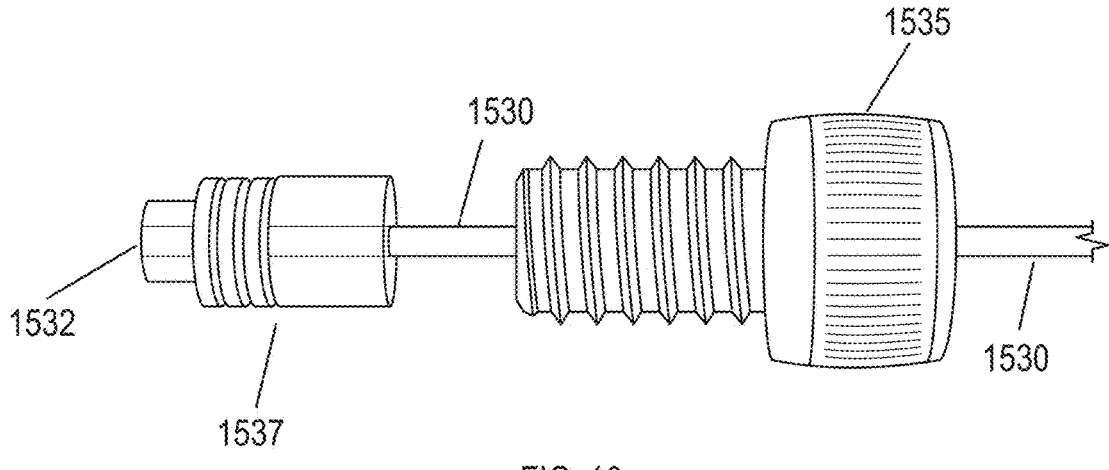
FIG. 16 is an enlarged view of a proximal end of the device of FIG. 15 showing the details of a threaded con-nector and a seal on a terminal end of a cryogenic fluid supply line.

FIG. 15 is a perspective view of a balloon-based cryoneu-rolysis device 1500. Various details of the device will be appreciated with reference to FIGS. 16-21. The balloon-based cryoneurolysis device 1500 has a handle 1505 with a lumen 1512 and an exhaust port 1510 in communication with the lumen 1512. There is a catheter shaft 1520 with a proximal end 1524 and a distal end 1522 and a lumen 1526 extending from the proximal end to the distal end. The proximal end of the catheter terminates within the handle 1505 such that the catheter lumen 1526 is in communication with the exhaust port 1510. Proximal to the handle there is a cryogenic fluid supply line 1530 having a proximal end 1532 and a distal end 1534 and a lumen 1536 therebetween. As best seen in FIG. 16, there is a threaded connector 1535 and a seal 1537 on the proximal end 1532 of the cryogenic fluid supply line 1530.

FIG. 16 is an enlarged view of proximal end of the device of FIG. 15 showing the details of a threaded connector 1535 and a seal 1537 on a terminal end 1532 of a cryogenic fluid supply line 1530.

Figure 17:
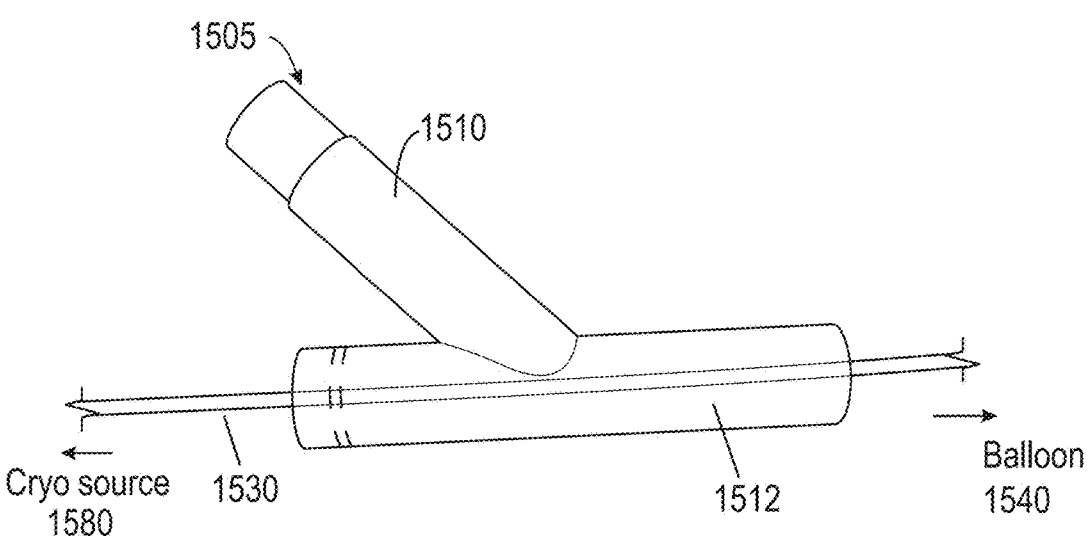
FIG. 17 is an enlarged view of a handle of the device of FIG. 15.

FIG. 17 is an enlarged view of a transparent handle of the device of FIG. 15. The cryogenic fluid supply line 1530 passes through the handle lumen 1512 and is secured in a sealed relation to the lumen using seal 1515. Seal 1515 ensures that gases from the balloon and catheter lumen exit through the exhaust port 1510.

Figure 18:
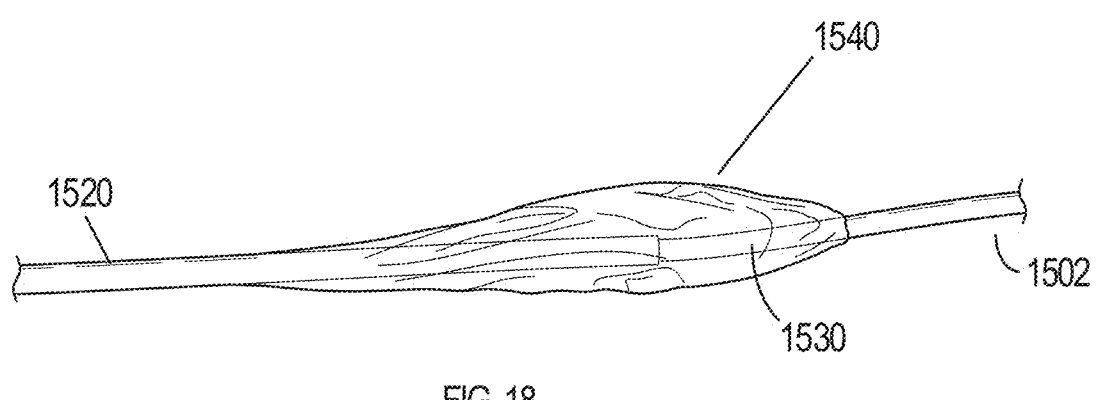
FIG. 18 is an enlarged view of an exemplary balloon as used with the device of FIG. 15.

FIG. 18 is an enlarged view of an exemplary balloon 1540 as used with the device of FIG. 15. In this embodiment, the proximal end of the balloon is over the catheter shaft and the distal end of the cryogenic fluid line can been seen in the balloon interior. This balloon embodiment has a straight atraumatic tip 1502 as an alternative to the curved tip 1503 (see FIG. 20).

Figure 19:
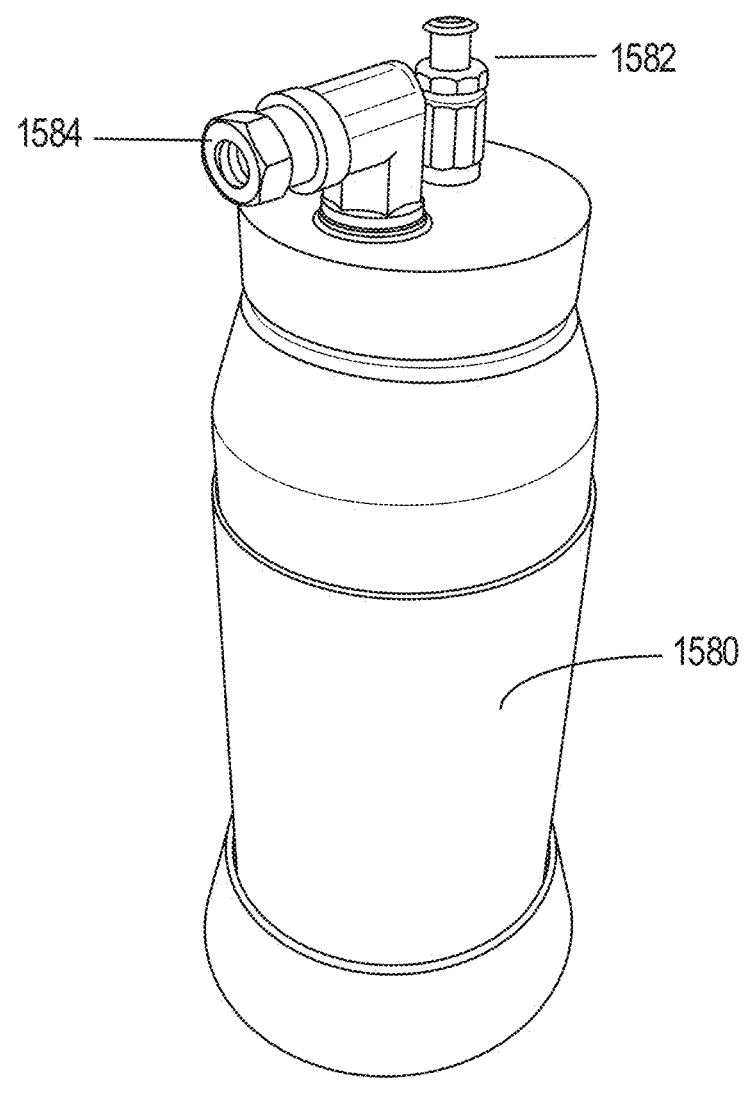
FIG. 19 is an isometric view of a cryogenic fluid container with an outlet to connect to the threaded connector best seen in FIGS. 15 and 16.

FIG. 19 is an isometric view of a cryogenic fluid container 1580 with an outlet 1584 to connect to the threaded con-nector 1535 and seal 1532 (FIG. 16). The liquid cryogenic fluid container includes conventional components such as a supply line and seals as needed based on operating pressure and cryogenic fluid. The fill port or pressure port 1582 may be used to create and maintain a desired operating pressure within the container 1580. In one aspect the cryogenic fluid may be liquid nitrogen, the container 1580 when then carry liquid nitrogen pressurized, for example, within a range from 30 psi to 100 psi. In use, the container outlet 1584 is coupled to the threaded connector 1535 and a seal 1537 on the proximal end of the cryogenic fluid supply line 1530.

Figure 20:
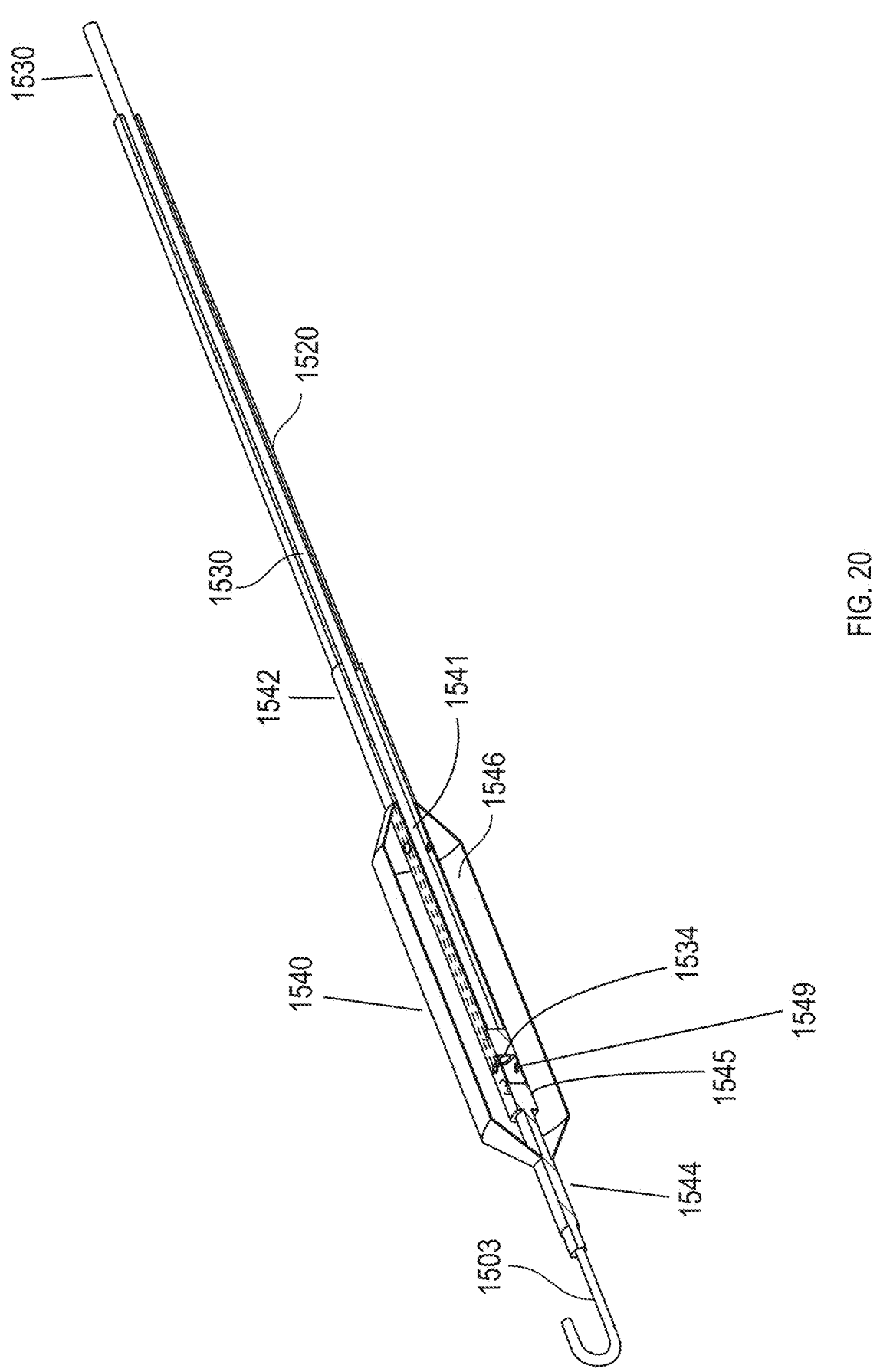
FIG. 20 is a cross-section view of a balloon embodiment that may be used with the device of FIG. 15.
Figure 21:
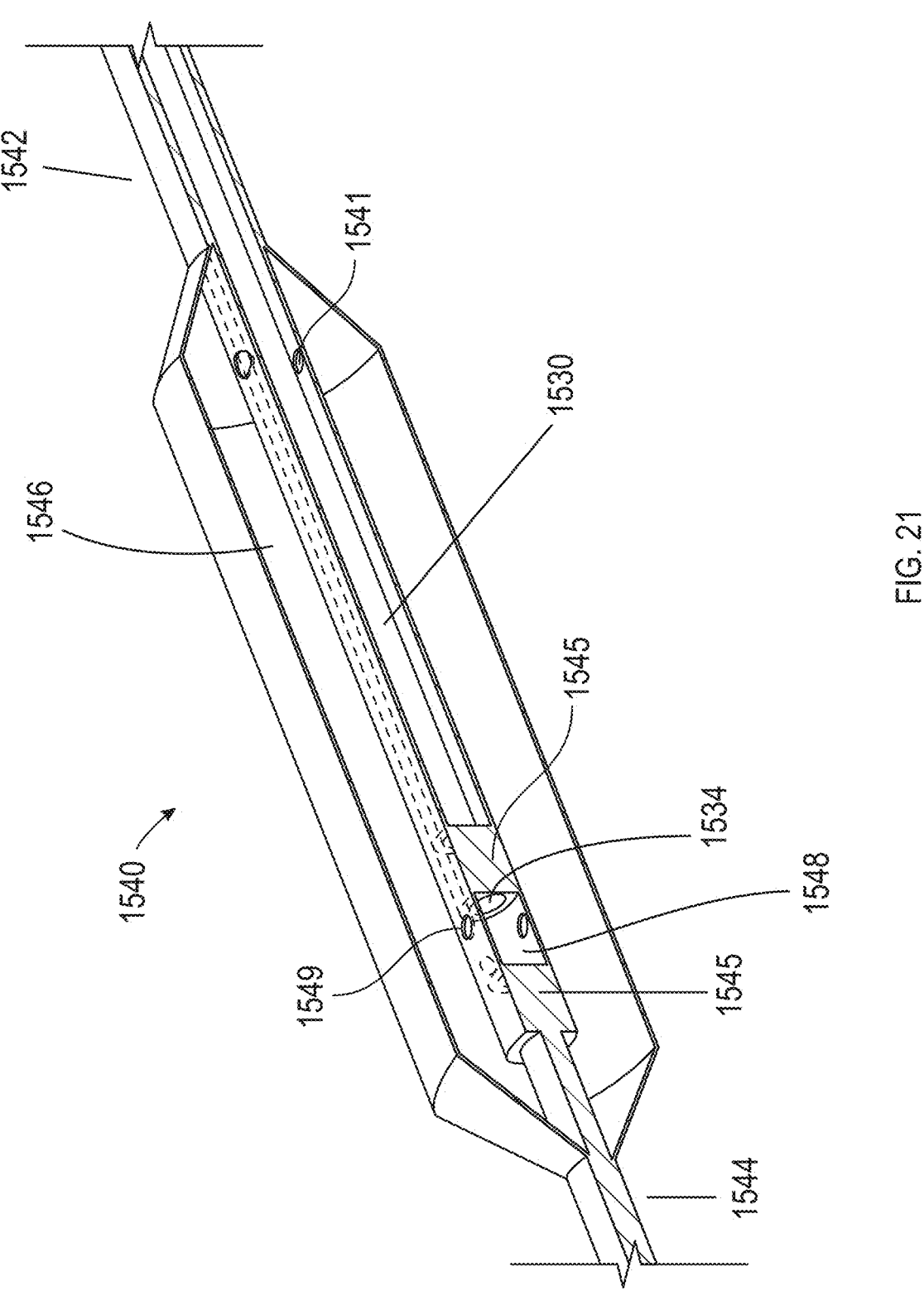
FIG. 21 is an enlarged view of the interior of the balloon shown in FIG. 20.

FIG. 20 is a cross-section view of a balloon embodiment that may be used with the device of FIG. 15. FIG. 21 is an enlarged view of the interior of the balloon shown in FIG. 20. There is a balloon 1540 on the distal end of the device 1500. The balloon 1540 is adapted and configured for performance of a venous cryoneurolysis therapy as described herein. The balloon has a proximal end 1542 and a distal end 1544 and an interior volume 1546. Within the balloon interior volume 1546, there is a liquid inlet block 1545 in fluid communication with the distal terminal end of the cryogenic fluid supply line 1530. The liquid inlet block 1545 has an inlet chamber 1548 with a plurality of apertures 1549 providing a fluid pathway from the distal end 1534 of the cryogenic fluid supply line and the balloon interior volume 1546. There are also one or more gas outlet apertures 1541 providing communication between the balloon interior volume 1546 and the exhaust port 1510 via the catheter lumen 1526. In operation to deliver balloon-based cryoneu-rolysis, a pressurized cryogenic fluid from cryogenic fluid container 1580 flows along the cryogenic fluid supply line through the distal end 1534 and into the inlet chamber 1548 of liquid inlet block 1545. As the liquid transitions into a gas, the gas flows into the balloon interior volume 1546 via the apertures 1549. After the balloon expands under continued liquid-gas conversion, gas flows out through the one or more gas apertures 1541 into the catheter lumen 1522 and out of the exhaust port 1510 in the handle 1505.

It is to be appreciated that the balloon—catheter attach-ment may be completed in any of a number of different arrangements. For example, an interior wall of the balloon coupled to an outer wall at the distal end of the catheter such that the interior volume of the balloon is in communication with the lumen of the catheter. In another alternative con-figuration, an exterior wall of the balloon is coupled to an inner wall at the distal end of the catheter such that the interior volume of the balloon is in communication with the lumen of the catheter.

Advantageously, there is an embodiment of the balloon-based cryoneurolysis device that has an overall length of less than 50 cm from the threaded connector 1535 and seal 1537 on the cryogenic fluid supply line 1530 to the distal most end of the catheter 1522. In one variation, there is an embodi-ment of the balloon-based cryoneurolysis device having an overall length of less than 30 cm from the threaded connec-tor 1535 and seal 1537 on the cryogenic fluid supply line to the distal most end of the catheter 1522. In yet other variations of the balloon-based cryoneurolysis device, in use for performance of venous cryoneurolysis therapy within a target vein, less than 30 cm of the catheter shaft proximal to a proximal end of the balloon is within the target vein. Optionally, in another variant of the balloon-based cryoneu-rolysis device, in use for performance of the venous cry-oneurolysis therapy within a target vein, less than 20 cm of the catheter shaft proximal to a proximal end of the balloon is within the target vein. In still another variation, the balloon-based cryoneurolysis device in use for performance of the venous cryoneurolysis therapy within a target vein, less than 15 cm of the catheter shaft proximal to a proximal end of the balloon is within the target vein.

In still other advantageous configurations of the balloon-based cryoneurolysis device, the balloon has a length of 20 mm and during use for performance of the venous cryoneu-rolysis therapy within a target vein the balloon inflates to distend the target vein to a diameter of 5-7 mm. In another variation the balloon-based cryoneurolysis device has a balloon with a length of 10 mm. During use for performance of the venous cryoneurolysis therapy within a target vein the balloon inflates to distend the target vein to a diameter of 5 mm, 6 mm, 7 mm or 8 mm. In another embodiment, the balloon of the balloon-based cryoneurolysis device has a length of 10 mm and during use for performance of the venous cryoneurolysis therapy within a target vein the balloon inflates to distend the target vein to a diameter of 5 mm, 6 mm, 7 mm or 8 mm. In each of the different various configurations, the balloon-based cryoneurolysis device during use in the performance of the venous cryoneurolysis therapy within a target vein the balloon inflates to distend the target vein while maintaining a target cryoneurolysis temperature for performance of the venous cryoneurolysis therapy within a target vein.

In still another advantageous configuration of the balloon-based cryoneurolysis device—in use for performance of the venous cryoneurolysis therapy within a target vein—there is less than 20 cm of the catheter shaft proximal to a proximal end of the balloon is within the target vein. Still further, the balloon has a length of 10-20 mm and during use for performance of the venous cryoneurolysis therapy within a target vein the balloon inflates to distend the target vein to a diameter of 5-9 mm. The balloon-based cryoneurolysis device operates for maintaining a target cryoneurolysis temperature for performance of the venous cryoneurolysis therapy within a target vein. In specific implementations, the target vein is one of a posterior tibial vein, a saphenous vein or a deep peroneal vein and the venous cryoneurolysis therapy is directed to symptoms of diabetic neuropathy in a lower limb or a foot. In one variation, the balloon-based cryoneurolysis device—in use for performance of the venous cryoneurolysis therapy within a target vein—the balloon inflates to distend the target vein to a diameter of 5-9 mm while maintaining a target cryoneurolysis temperature for performance of the venous cryoneurolysis therapy within a target vein. In one implementation, the target vein is one of a posterior tibial vein, a saphenous vein or a deep peroneal vein and the venous cryoneurolysis therapy is directed to symptoms of diabetic neuropathy in a lower limb or a foot. In still another alternative, in use for performance of the venous cryoneurolysis therapy within a target vein, the balloon inflates to distend the target vein to a diameter of 5-9 mm while maintaining a target cryoneurolysis temperature for performance of the venous cryoneurolysis therapy in a target vein that is one of a posterior tibial vein, a saphenous vein or a deep peroneal vein. The venous cryoneurolysis therapy is directed to symptoms of diabetic neuropathy in a lower limb or a foot. In one implementation of the balloon-based cryoneurolysis device, in use for performance of the venous cryoneurolysis therapy within a target vein the balloon inflates to distend the target vein to provide a cold zone at a target nerve within a range of $-20°$ C.$-80°$ C.

Evaluating the Efficacy of the Balloon-Based Transvenous Cryoneurolysis Catheter System The balloon-based venous cryoneurolysis catheter system of FIG. 15 was tested to evaluate the efficacy of its respective transvenous cryoneurolysis balloon system where the cryogenic fluid was liquid nitrogen ($LN_2$) to achieve targeted cooling. This study provided additional information towards the development of the balloon-based venous cryoneurolysis catheter 1500 that will undergo animal testing to confirm these results in vivo.

As seen in FIG. 15, the balloon-based venous cryoneurolysis catheter 1500 may utilize an 8 F compatible cryoballoon catheter 1500 comprising a cryoballoon 1540 that may be connected to the 350 cc $LN_2$ spray bottle 1580 shown in FIG. 19. The 350 cc $LN_2$ spray bottle 1580 shown in FIG. 19 is pressurized between 10 to 75 psi to control the flow rate. Also, FIG. 17 shows a side view of the exhaust port and the $LN_2$ delivery line of the catheter 1500 of FIG. 15, whereas FIG. 18 shows the cryoballoon 1540 of the catheter 1500 of FIG. 15. As also seen in FIG. 20, the balloon-based venous cryoneurolysis catheter system may utilize a $LN_2$ delivery line 1530 and a cryoballoon 1540.

The balloon-based venous cryoneurolysis catheter 1500 of FIG. 15 was evaluated to see its efficacy in achieving targeted cooling in a saline solution followed by an agar solution. As such, the experimental testing was conducted in a saline solution followed by an agar solution. The primary objective of the experimental testing was to effectively cool the solution to a temperature below $-20°$ C. at a distance of 10 mm from the balloon surface. Further, thermocouples were strategically placed to monitor temperature at a pre-specified distance from the cryoballoon surface. Although the intended distance was 10 mm, some deformation in the thermocouple frame during testing resulted in measurements being taken at a distance of approximately 20-25 mm from the balloon surface.

Figure 22:
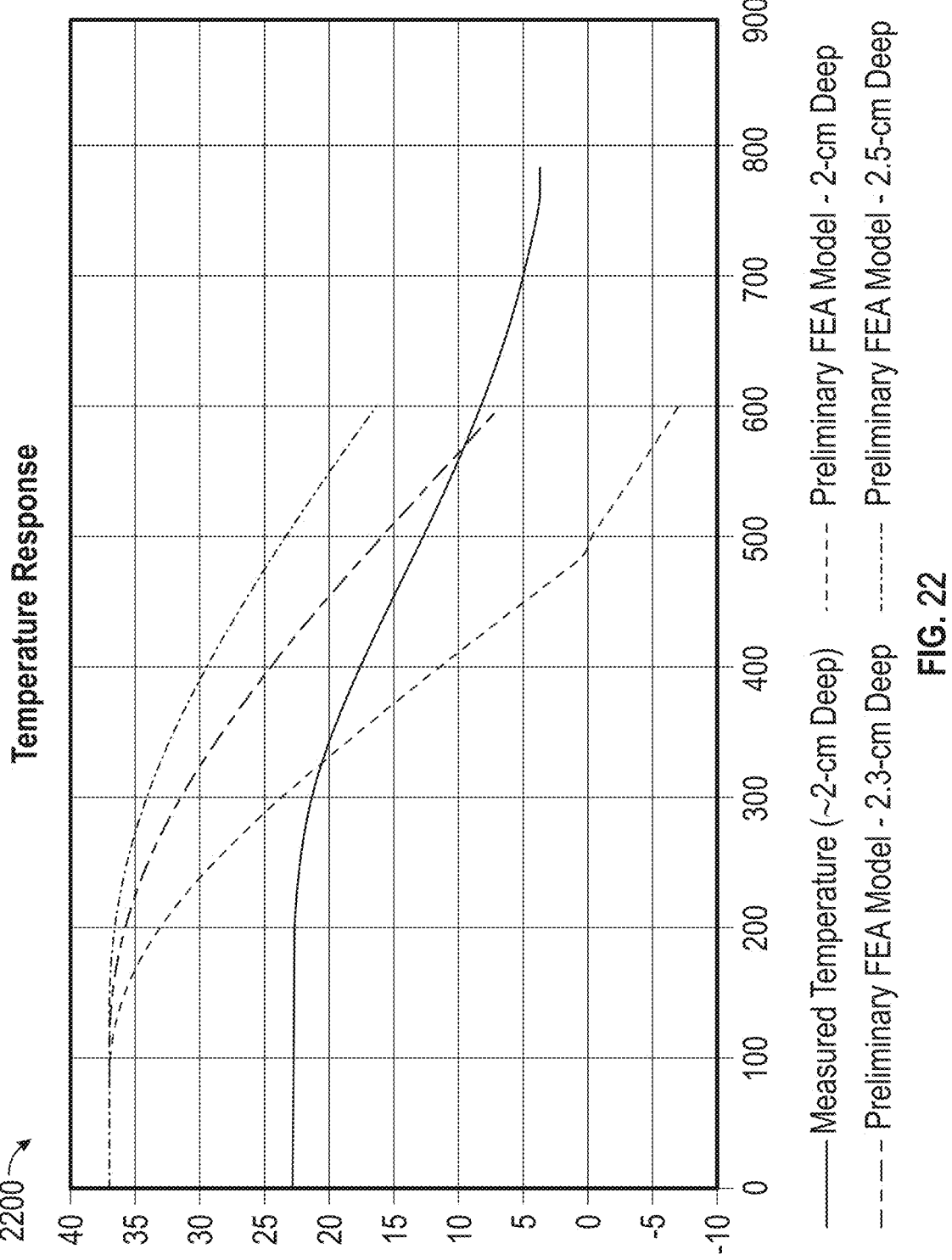
FIG. 22 illustrates a Temperature Response at distances of 20-25 mm from the cryoneurolysis balloon surface, for both the measured data and the Finite Element Analysis (FEA) model.

As seen in FIG. 22, the Temperature Response at distances of about 20 mm from the cryoneurolysis balloon surface was measured. The measured data cools from a temperature of circa $23°$ C. to below $5°$ C. at around 750 seconds, which is in general alignment with the Finite Element Analysis (FEA) model data, thereby validating the cooling performance of the balloon-based venous cryoneurolysis catheter 1500 of FIG. 15.

Figures 23, 24, 25:
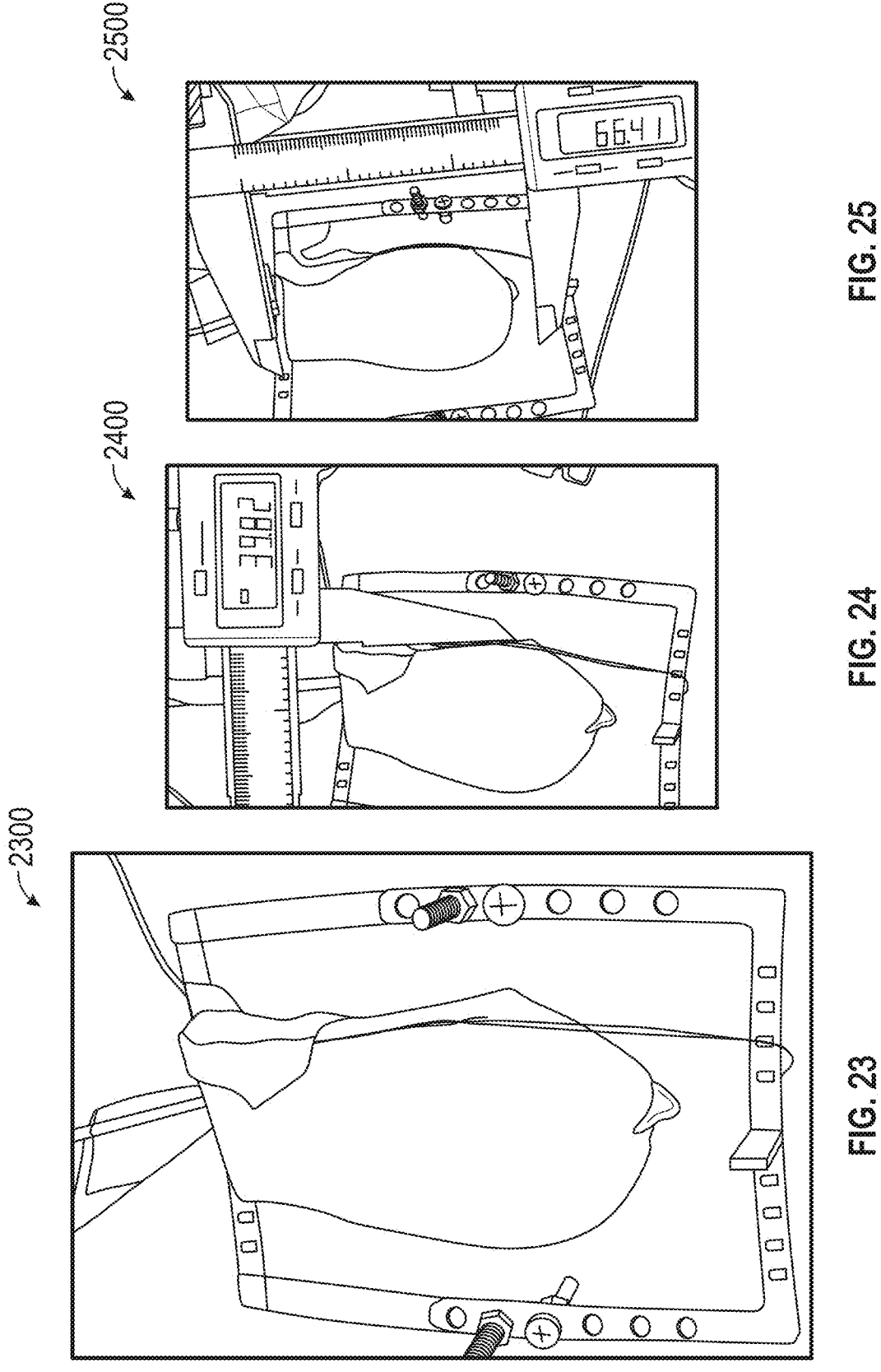
FIGS. 23-25 illustrate the frozen agar solution.

The testing demonstrated successful cooling in a saline solution, resulting in the formation of a 20.3 mm iceball. Further testing demonstrated successful cooling within a hot agar solution, resulting in an iceball measuring 39.8 mm diameter, as seen especially in FIG. 24. This testing further validated the cooling capabilities of the balloon-based venous cryoneurolysis catheter 1500 of FIG. 15.

Figure 26:
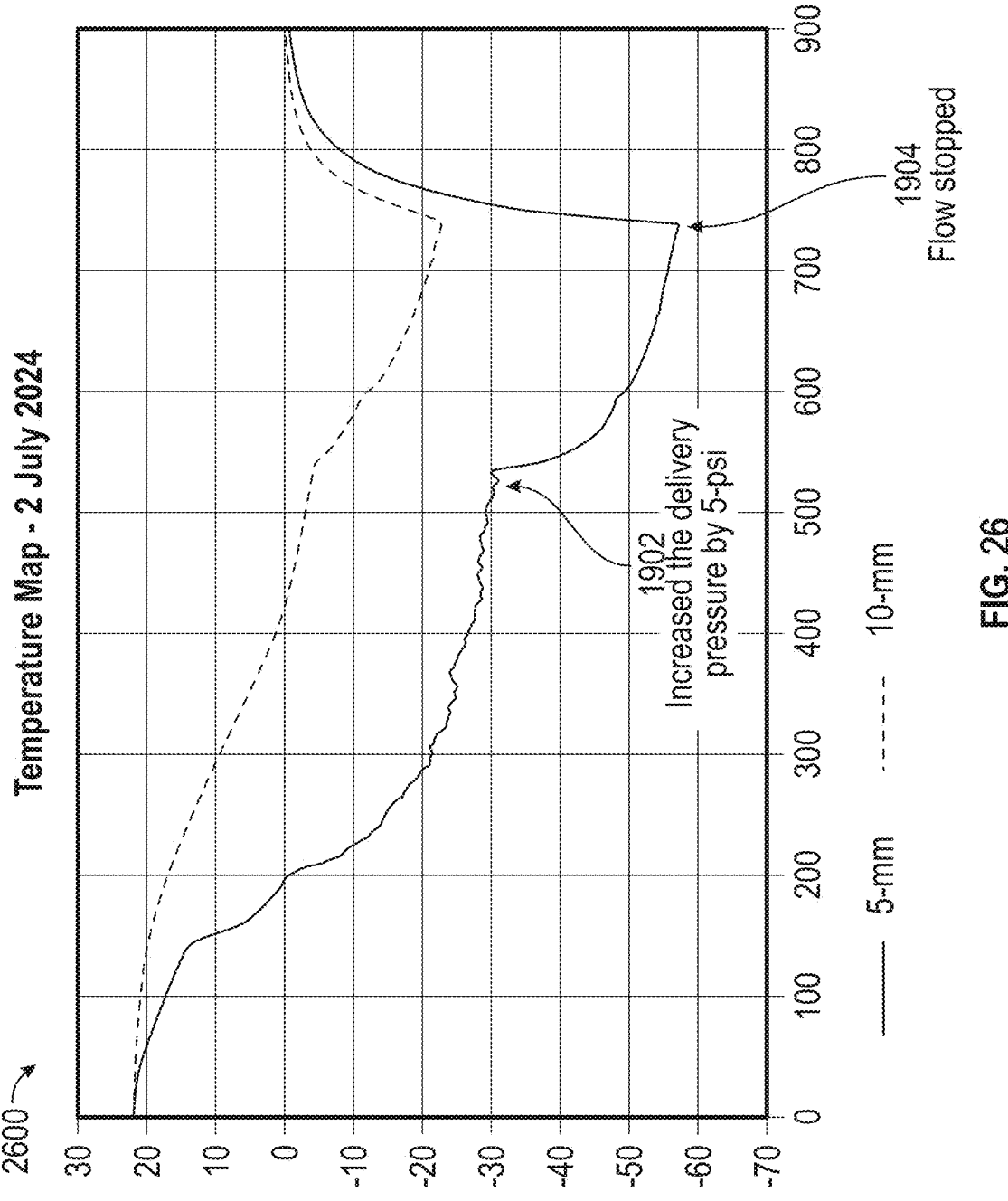
FIG. 26 illustrates a Temperature Response after an increase of the delivery pressure of the Liquid Nitrogen by 5 psi.

In still further testing, the delivery pressure of the liquid nitrogen ($LN_2$) system was increased by 5 psi. As seen in FIG. 26, the increase by 5 psi occurred around 1902, before the flow stopped at 1904. As further seen in FIG. 26, the increase by 5 psi of the Liquid Nitrogen $LN_2$ further cooled the balloon-based venous cryoneurolysis catheter system of FIG. 15 from a temperature of circa $-30°$ C. to circa $-57°$ C. As such, the experimental testing confirmed that the balloon-based venous cryoneurolysis catheter system of FIG. 15 not only cools a targeted area effectively, but also responds well to increased pressure, thereby allowing for precise control over Liquid Nitrogen $LN_2$ delivery. Specifically, since the results confirmed that the 5 psi pressure increase further cooled the balloon-based venous cryoneurolysis catheter system of FIG. 15, this indicates each system's responsiveness to pressure adjustments and fine-tuning of the cooling process via the adjusting of pressure delivery of the Liquid Nitrogen, which may enable further optimization of the balloon-based venous cryoneurolysis catheter system of FIG. 15 for various therapeutic purposes.

Use of the Balloon-Based Venous Cryoneurolysis Catheter System in Animal Studies and Animal Testing The balloon-based venous cryoneurolysis catheter system of FIG. 15 was tested to evaluate the safety and efficacy of utilizing the venous cryoneurolysis catheter system of FIG. 15 for cryoneurolysis of peripheral nerves in the lower extremities of a sheep model.

Specifically, the sheep model was placed in front of the angiography table. Under real time ultrasound guidance, the vein was accessed at the lateral saphenous vein at the level of the ankle. The balloon-based venous cryoneurolysis catheter 1500 was positioned in the above knee lateral saphenous vein (vein diameter of ~5.5 mm), and three balloon sizes were tested (4, 5, and 6 mm×20 mm). Once the catheter 1500 was in place, cryoneurolysis commenced to achieve a tip temperature between −20° C. and −80° C. This was performed in 8-2-8 minute freeze-thaw-freeze cycles. Further, ultrasound was used to visualize the formation of the iceball. At the end of the study, arteriograms and venograms were obtained as well as histology results.

Figures 27A, 27B, 27C, 27D:
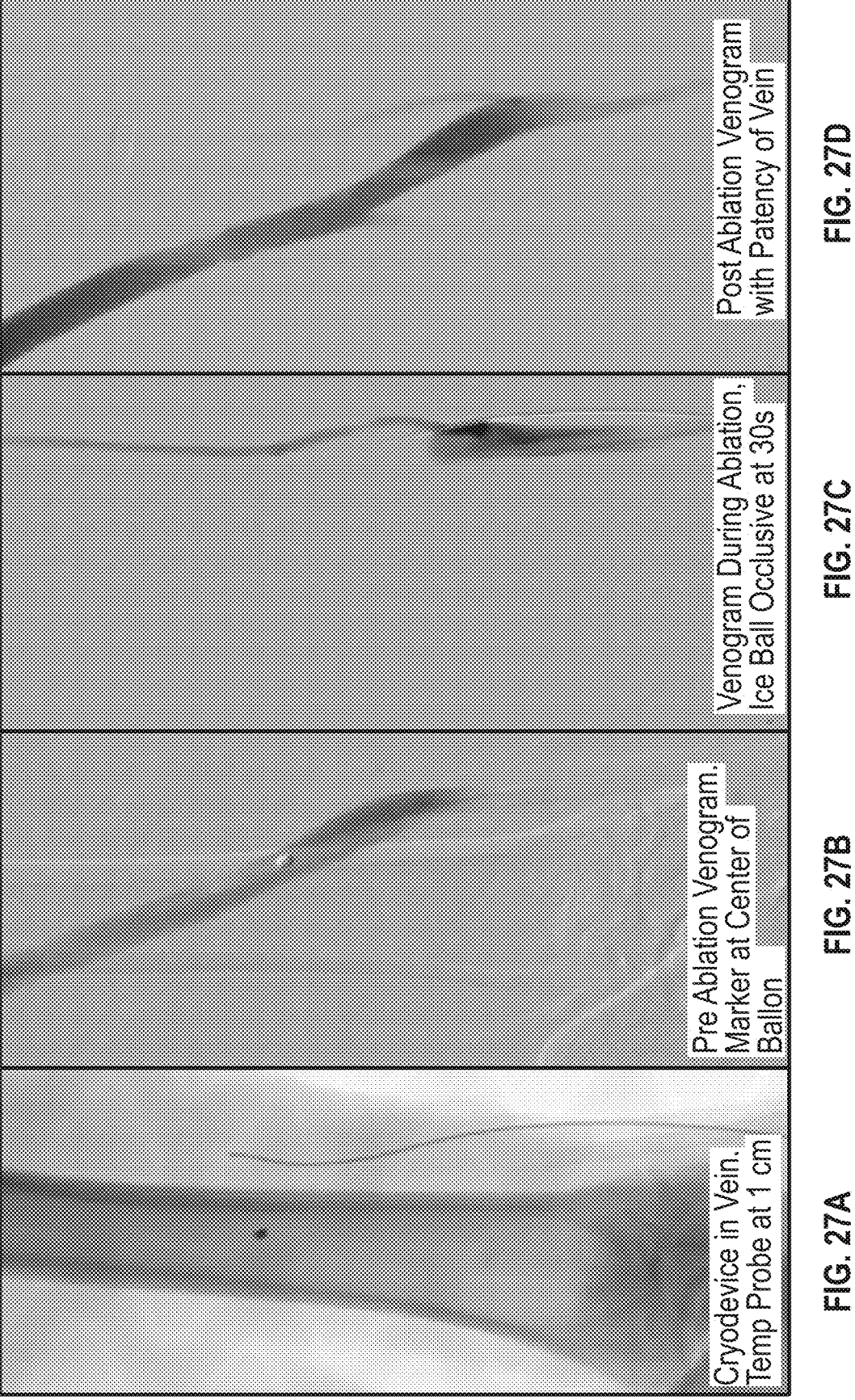
FIGS. 27A-27D illustrate a series of venograms as the balloon-based venous cryoneurolysis catheter device enters the vein.

As seen in FIGS. 27A-27D, a series of venograms were collected as the balloon-based venous cryoneurolysis catheter 1500 enters the vein. FIG. 27A shows the single radioopaque marker positioned at the center of the cryoballoon. Specifically, the wire next to the balloon is a temperature probe placed 1 cm or 10 mm from the vein/balloon to measure treatment temperatures during the freeze-thaw cycles. FIG. 27B shows the pre-cryoneurolysis treatment venogram and demonstrates the patency of the vein with the cryoneurolysis catheter in place. FIG. 27C illustrates a venogram during cryoneurolysis and demonstrates complete occlusion by the ice ball within 30 seconds, demonstrating the efficacy of the venous catheter system. FIG. 27D shows the venogram after a passive thaw cycle of 8 min freeze-15 min (passive thaw)-8 min freeze cycle. Further, removal of the cryoneurolysis catheter shows patency of the vein post procedurally.

Figure 28A:
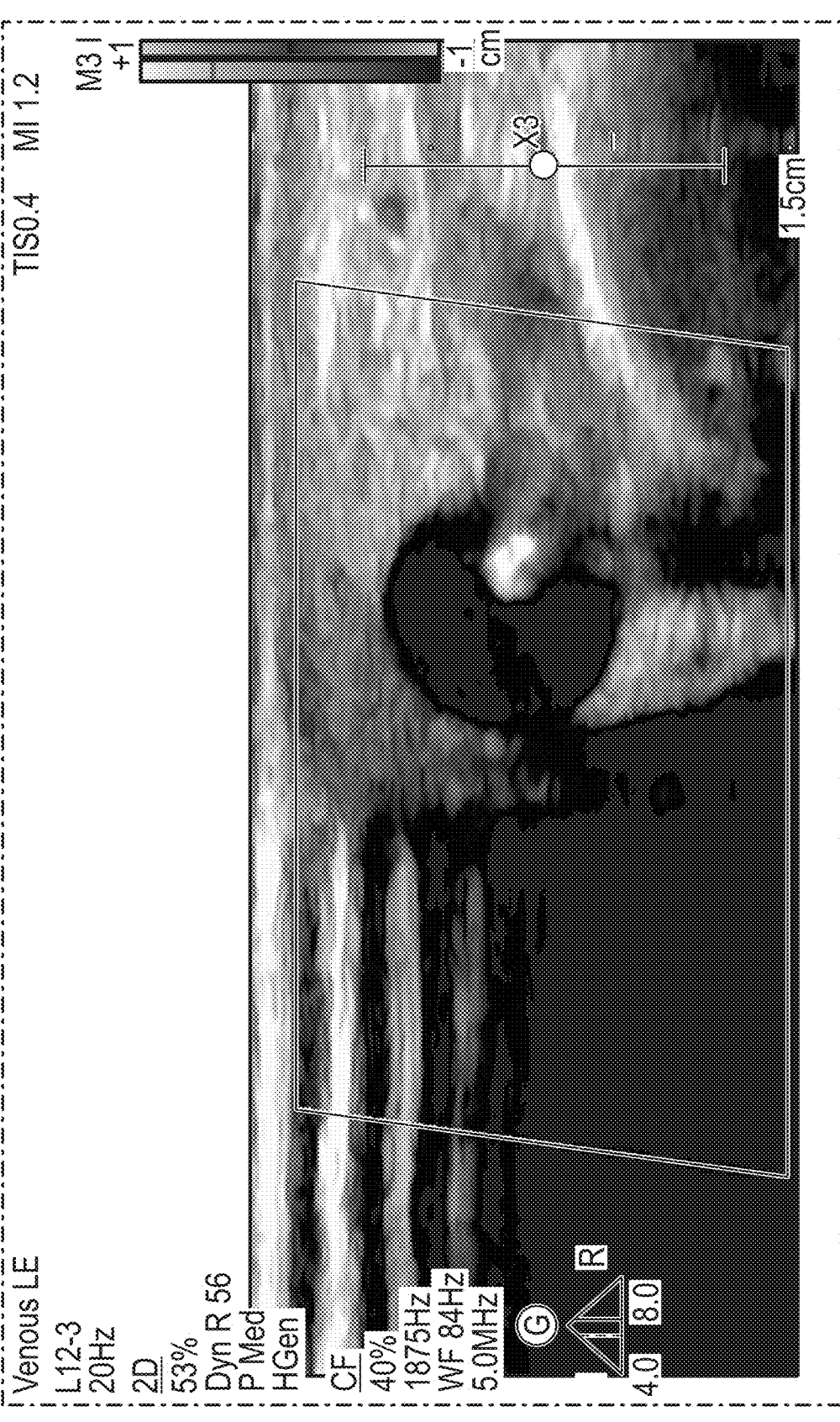
FIGS. 28A-28C illustrate the iceball from the center of the vein when the balloon-based venous cryoneurolysis catheter device is inside the vein.
Figure 28B:
Figure 28C:
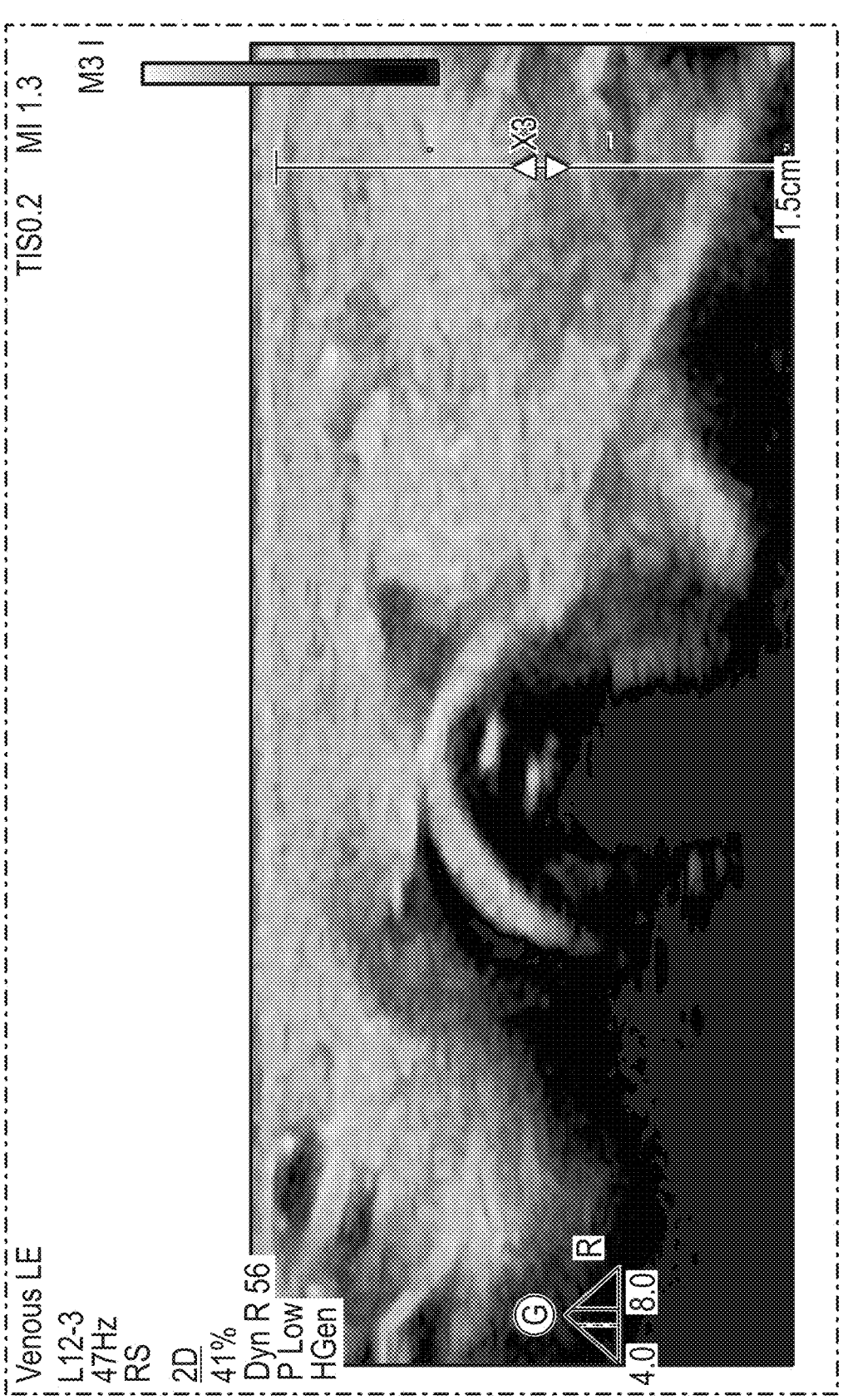

FIGS. 28A-28C show the growing iceball on serial images from the center of the vein. Initially, the vein is much larger than the balloon and the balloon is not occlusive in the image of FIG. 28A. Thereafter, however, the iceball grows, resulting in occlusion.

Further, FIG. 29 illustrates the results of the cryoneurolysis studies and the Animal Lab Acute Pathology Findings of the above experimental testing on the sheep model.

Specifically, as seen in FIG. 29, the results for the Nov. 19, 2024, study indicate that a temperature of −17° C. was recorded at 10 mm from the vein/balloon, via the aforementioned temperature probe shown in FIG. 27A. Further, the effect on the nerve was observed in the form of acute axonal swelling, which indicates efficacy. Meanwhile, the vascular integrity was maintained as the veins remained open and minimal intravascular clot was noted. Also, no damage occurred to the adjacent artery, as confirmed by histology results. Further, the muscle response involved acute muscle necrosis localized near the treatment zone, while the skin involvement showed localized epithelial and adnexal necrosis. In effect, the Nov. 19, 2024, study demonstrated basic feasibility of cryoneurolysis.

The results for the Mar. 4, 2025, study indicate a temperature of −108° C. that was recorded at 5 mm from the balloon/vein and a temperature of −46° C. at 10 mm from the balloon/vein. Further, the effect on the nerve was observed in the form of more pronounced acuate axonal swelling and irregular sheath. Meanwhile, the vascular integrity was maintained as the veins remained open and no Deep Vein Thrombosis (DVT) was observed post-procedurally. Also, no damage occurred to the adjacent artery, as confirmed by histology results. Further, the muscle response involved extensive muscle necrosis noted in some areas, while the skin involvement showed diffuse dermal coagulative necrosis with microhemorrhage. In effect, the histological indicators of efficacy included vein wall edema, necrosis, hemorrhage, axonal disruption.

The Mar. 4, 2025, study confirmed robust cryoneurolysis effect at deeper temperature zones. Further, the lack of thrombotic complications (e.g., DVT) or arterial compromise validates vascular safety at colder temperatures. Moreover, Histopathology confirms nerve disruption while preserving vascular structures within the treatment zone, resulting in an effective and confirmed cryoneurolysis effect. As such, the Mar. 4, 2025, study demonstrates clear advancement in treatment efficacy of the balloon-based venous cryoneurolysis catheter system of FIG. 15, due at least in part to deeper cooling, no damage to the adjacent artery, and minimal tissue damage.

Various embodiments of the balloon-based transvenous cryoneurolysis system and the transvenous cryoneurolysis device may be used to advantage in providing for temporary relief of acute and chronic pain and temporary cryoanalgesia to various targeted nerves and neurosomes. Indeed, various methods of providing cryoanalgesia to the targeted nerves and neurosomes may be appreciated with regard to the following:

FIG. 30 is a flow chart of an exemplary method 3000 for performing a transvenous access cryoneurolysis procedure to treat a symptom of a patient. The symptom may be one associated with post-surgery pain, chronic pain, peripheral neuropathy, neuropathic pain or diabetic neuropathy. Still further, in a specific implementation, there is a method of performing a transvenous cryoneurolysis procedure to treat a symptom of peripheral neuropathy in a patient. First, at 3005, there is a step of identifying a target neurosome for performing the transvenous cryoneurolysis to provide relief to the symptom of peripheral neuropathy. Next, at 3010, there is a step of identifying a target nerve associated with the target neurosome. Next, at 3015, there is a step of selecting a target vein for accessing the venous vasculature in proximity to the target nerve. Then, at 3020, there is a step of accessing the venous vasculature of the target vein with a transvenous cryoneurolysis device. Next, at 3025, there is a step of advancing the transvenous cryoneurolysis device along the target vein to a treatment position in proximity to the target nerve associated with the target neurosome. Then, at 3030, there is a step of inflating the transvenous cryoneurolysis device to distend the target vein in proximity to the target nerve. Then, at 3035, depending on the desired outcome, there is a step of performing at least one freeze-thaw cryoneurolysis cycle within a range of −20° C. to −80° C. in a cold zone including a portion of the target nerve. Once the desired number of freeze-thaw cycles are completed, deflate the transvenous cryoneurolysis device and remove the venous cryoneurolysis device from the target vein (step 3040).

The exemplary method 3000 for performing a transvenous access cryoneurolysis procedure to treat peripheral neuropathy symptoms in a patient may be modified in a number of differ ways. In one variation, the accessing the venous vasculature of the target vein is selected such that the advancing the venous cryoneurolysis device along the target vein to a treatment position includes antegrade motion of the transvenous cryoneurolysis device along the target vein. The process of inflating the transvenous cryoneurolysis device step may also reduce the distance between the transvenous cryoneurolysis device and a portion of the target nerve in proximity to the target vein. In some cases, after the inflating step, the target vein has been distended from 2 mm to 12 mm. In some performances of the method there is a distending force maintained on the target vein adjacent to the transvenous cryoneurolysis device during one freeze-thaw cycle or during each freeze-thaw cycle. In one implementation of the method, after the performing step, an axial cryolesion with a length from 1 cm to 10 cm is formed along the target nerve. In one implementation, the length of the axial cryolesion along the target nerve is related to a length of the inflated portion of the transvenous cryoneurolysis device. In some alternative implementation there may also be a step of maintaining a compression force on the target vein adjacent to the cryoneurolysis device during one freeze-thaw cycle or during each freeze-thaw cycle. Alternatively, in another implementation, there is a process for maintaining compression and applying heat to the target vein adjacent to the cryoneurolysis device during one freeze-thaw cycle or during each freeze-thaw cycle.

In one specific implementation, the symptom of peripheral neuropathy, or neuropathic pain or diabetic neuropathy is related to a leg, an ankle or a foot of the patient. The method may also have the target neurosome include a portion of the saphenous nerve. The method may also have the target vein as the great saphenous vein and the step of accessing the venous vasculature is in proximity to an ankle of the patient. There may also be an implementation of the method where the at least one symptom of neuropathic pain or diabetic neuropathy is degraded muscle function in the posterior compartment of the leg such as gastrocnemius, soleus, tibialis posterior or the intrinsic foot muscles or sensation to the heel and sole of the foot. Still another variation, the targeted neurosome includes a portion of the tibial nerve. Moreover, when the target vein is the posterior tibial vein there may be an access point that is adjacent to an ankle of the patient. In another implementation of the method, there may be at least one symptom of neuropathic pain or diabetic neuropathy that is deteriorated muscle function or innervation of the muscles of the anterior compartment of the leg responsible for dorsiflexion of the foot and extension of the toes or related to sensation to the web space between the first and second toes or associated with a portion of the dorsal aspect of the foot. This method may be applied where the targeted neurosome includes a portion of the deep peroneal nerve. In another implementation, the target vein is the anterior tibial vein and an access point is adjacent to an ankle. The methods described herein advantageously utilize a short overall length venous cryoneurolysis device to perform the method. Such a device has an overall length from a handle on a proximal portion of a catheter to the distal most end of the device that is less than 30 cm or is 25 cm, or is 20 cm, or is 15 cm. Other lengths may be used based on user preference, however one key benefit of proper target vein and access point selection is to substantially reduce the operating length of the catheter and balloon in the target vein. Along these same lines, in some embodiments, during the one or more freeze-thaw cycles the length of the catheter shaft of venous cryoneurolysis device proximal to the most proximal portion of the balloon that is within the target vein is less than 20 cm. Additionally, a length of the balloon of the transvenous cryoneurolysis device is selected so as to more predictably control a length of an axial cryolesion formed along the target nerve.

FIG. 31 is a flow chart of an exemplary method 3100 of performing transvenous cryoneurolysis for temporary cryoanalgesia of a symptom of a patient. First, there is a step of selecting a vein of the patient as a target vein for a transvenous cryoneurolysis access point (step 3105). Next, there is a step of inserting a transvenous cryoneurolysis device into the target vein (step 3110). Then, there is a process of advancing the transvenous cryoneurolysis device to a location within the target vein adjacent to a target nerve associated with the symptom of the patient. (step 3115).

After advancing, there is a process of inflating a balloon of the transvenous cryoneurolysis device to achieve circumferential wall contact with an inner wall of the target vein. (step 3120). Inflating the balloon with a cryogenic fluid produces cooling the balloon to a temperature below −20° C. to create a thermal zone including a portion of the target nerve adjacent to the balloon. (step 3125). Next, there is a process of performing one or more freeze-thaw cycles with the balloon to induce temporary cryoanalgesia of a portion of the target nerve to provide the patient relief of the symptom. (step 3130). Thereafter the transvenous cryoneurolysis device may be deflated and removed from the target vein of the patient.

The method 3100 of performing transvenous cryoneurolysis for temporary cryoanalgesia of a symptom of the patient is subject to a number of variations and alternatives. The method may be applied advantageously to a target vein that is one of the great saphenous vein, the posterior tibial vein or the anterior tibial vein. In one implementation, the symptom of the patient is related to peripheral neuropathy. Additionally, the inserting step may be performed at a location in the target vein wherein the distance from the access point in the target vein to the location adjacent to the target nerve is less than 10 cm. Still further, the inserting step is performed at a location in the target vein wherein the movement of the transvenous cryoneurolysis device from the access point to the location adjacent to the target nerve includes antegrade motion along the target vein. This type of motion reduces the risk of interference between the device and the valves in the target vein. It is to be appreciated in some implementations in veins that do not have internal valve structures, the motion of the transvenous cryoneurolysis device may be selected independent of antegrade motion but may instead be selected to reduce the distance of travel or simplify navigation along the target nerve from an access point. Another benefit of using a balloon is that the inflating step—because of distention of the target vein wall—reduces the distance from the outer wall of the target vein to a portion of the target nerve. This reduction can reduce the size of the cool zone needed to get the desired effect. In some implementations, after the advancing step the venous cryoneurolysis device is from 3-7 mm from a portion of the target nerve. During the cooling the balloon step the thermal zone has a temperature in the range −20° C. to −80° C. at a portion of the target nerve. Additionally, during the cooling the balloon step the thermal zone has a temperature above −80° C. at target nerve location to aid in preventing damage to motor nerves or maintaining selectivity to the targeted sensory nerves. Put another way, the cooling the balloon step the thermal zone maintains a temperature to induce Sunderland 2 axonotmesis in sensory fibers of the target nerve. Another benefit is that during the cooling the balloon step the thermal zone is from 3 mm to 10 mm from the location of the balloon of the venous cryoneurolysis device within the target vein.

In one specific implementation of method 3100, the target vein is the great saphenous vein, the target nerve is the saphenous nerve and an access point anatomical landmark is with 3 cm anterior to the medial malleolus. In another specific implementation of method 3100, the target vein is the posterior tibial vein, the target nerve is the tibial nerve and an access point anatomical landmark is within 2 cm of the arch of the foot just behind the medial malleolus. In yet another specific implementation of method 3100, the target vein is the anterior tibial vein, the target nerve is the common peroneal nerve and an access point anatomical landmark is midway between the tibia and the fibula at ankle and lateral to the extensor hallucis longus.

In still another implementation of method 3100, the target vein is one of an internal pudendal vein, an external iliac vein tributary or an external iliac vein. Additionally, the target nerve may be one of a pudendal verve, an ilioinguinal nerve or a genitofemoral nerve and the symptom is related to one or more of a chronic pelvic pain, a pudendal neuralgia, a sensory neuropathy post-hernia repair or a postoperative inguinodynia. Optionally, depending on implementation and the results of the freeze-thaw cycles, after the performing step a cryolesion is formed along the target nerve having a length related to a length of the balloon of the transvenous cryoneurolysis device. In still another aspect, during the cooling the balloon step a distance from the balloon in the target vein to the target nerve is from 3-7 mm.

It should be appreciated that all combinations of the foregoing concepts and additional concepts discussed in greater detail herein (provided such concepts are not mutually inconsistent) are contemplated as being part of the inventive subject matter disclosed herein and may be used to achieve the benefits described herein.

The benefits of the use of the venous tree are wide ranging where the location of the target vein is aligned longitudinally with a target nerve. In contrast to existing conventional approaches, the advantageous pairing of target vein/target nerve allows for a more selective, controllable longitudinal lesion on the target nerve. In one aspect, the relationship of balloon length to cold zone and proximity to the target nerve provides a readily controllable/selective cryolesion location, length and size on the target nerve. Accordingly, various embodiments of the inventive device and transvenous cryoneurolysis methods provide by way of example and not limitation these possible target vein and venous access sites arranged by body portion:

Lower extremity: great saphenous vein, small saphenous vein, posterior tibial vein, anterior tibial vein, common femoral vein, femoral vein, popliteal vein, and associated variants.

Upper extremity: radial, ulnar, brachial, antecubital, forearm perforators, basilic, cephalic, brachial, axillary.

Head/neck: internal jugular, external jugular, superior ophthalmic, facial, retromandibular, occipital, posterior auricular.

Thoracic: subclavian, brachiocephalic, SVC, lateral thoracic vein, internal mammary vein, anterior and posterior intercostal veins.

Abdomen: external iliac, inferior epigastric, IVC, lumbar, azygos, hemiazygos.

As a result of the wide-ranging access provided by the venous tree, there are even more possible target nerve sites or additional nerves to target within identified neurosome, such as by way of example:

Lower Extremity: Femoral nerve, obturator nerve, saphenous nerve, peroneal, tibial nerves, geniculate nerve, sural nerve.

Upper Extremity: Median nerve, Ulnar nerve, Radial nerve.

Head and Neck: Trigeminal nerve, Vagus nerve, Accessory nerve, cervical plexus, stellate ganglion.

Thorax: Phrenic nerve, Intercostal nerves, brachial plexus.

Abdomen/Pelvis: Pudendal nerve, Ilioinguinal nerve, splanchnic plexus, hypogastric plexus, superior mesenteric plexus, celiac plexus, aorticorenal plexus, ganglion impar, sciatic nerve, lateral femoral cutaneous nerve, posterior femoral cutaneous nerve.

The combination of access via the venous tree with specific or selective targeting of nerves or neurosome leads to a similarly large number of possible conditions that may be treated using a suitable cryoneurolysis device and method as described herein, such as by way of example and not limitation:

Lower Extremity: diabetic neuropathy, phantom limb pain, and complex regional pain syndrome, sciatica, knee arthritis, inflammatory arthropathy.

Upper Extremity: carpal tunnel syndrome, cubital tunnel syndrome, and radial nerve palsy.

Head and Neck: trigeminal neuralgia, migraine headaches, and tension headaches. Vagus nerve modulation could also impact depression and anxiety.

Thorax: chronic respiratory disorders like chronic obstructive pulmonary disease (COPD) by modulating diaphragm function, and intercostal neuralgia.

Abdomen/Pelvis: pelvic pain, interstitial cystitis, chronic prostatitis, urinary and fecal incontinence, irritable bowel syndrome, gastroparesis, biliary colic.

Put another way, transvenous cryoneurolysis devices may be delivered and navigated using any of a wide array of different venous access sites and pathways to navigate to target nerve site via standard interventional techniques, perform cryoneurolysis according to established freeze-thaw protocol to treat a pre-selected symptom or associated medical condition. In one aspect, the clinical goal is to deliver a Sunderland 2 nerve injury at the target nerve site with target temperatures of −20 to −80 degrees C. Still further, it is to be appreciated that the inflatable device combined with the elastic response of a vein provided a double benefit whereby balloon expansion results in reducing heat sink as well as reducing distance from vein to nerve. There is an added reduction to heat sink effect as compared to arterial approaches in that the blood flow in veins is less that on the arterial tree and there is less concern for incidental damage to the vein used for delivery.

The simplicity and short procedure time possible using approaches from the venous tree are appreciated in these examples to address symptoms of peripheral neuropathy via the following lower extremity venous access sites and target nerves:

1. Great Saphenous Vein at the Ankle: Nearby Nerve: Saphenous Nerve

Relation: Runs along the great saphenous vein on the medial aspect of the leg.

Function: Sensory

Sensory Innervation: Provides sensation to the medial side of the leg, ankle, and foot.

2. Posterior Tibial Vein at the Ankle: Nearby Nerve: Tibial Nerve

Relation: Travels behind the medial malleolus along with the posterior tibial artery and veins.

Function: Both Motor and Sensory

Motor Innervation: Supplies the muscles in the posterior compartment of the leg (e.g., gastrocnemius, soleus, tibialis posterior) and some of the intrinsic foot muscles.

Sensory Innervation: Provides sensation to the heel and sole of the foot.

3. Anterior Tibial Vein at the Ankle: Nearby Nerve: Deep Peroneal (Fibular) Nerve Relation: Accompanies the anterior tibial artery and vein on the anterior aspect of the leg.

Function: Both Motor and Sensory

Motor Innervation: Innervates the muscles of the anterior compartment of the leg responsible for dorsiflexion of the foot and extension of the toes.

Sensory Innervation: Provides sensation to the web space between the first and second toes and part of the dorsal aspect of the foot.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed in the following exemplary Tables.

Tables

As mentioned above, the venous cryoneurolysis system may utilize venous access for cryoneurolysis of targeted nerves and neurosomes. Further, the venous cryoneurolysis system may be appreciated with regard to the aforementioned examples in the lower extremity of the body. To aid in targeting nerves and neurosomes in the lower extremity of the body, the disclosure provides the table of FIG. 32, which illustrates a table of the Lower Extremity Nerve/Vein Target Map with Access Landmarks. Advantageously, FIG. 32 is a table detailing additional target nerves for using the inventive venous cryoneurolysis methods and devices in the lower extremity of the body. Further, the table of FIG. 32 provides a reference map, an anatomical guidance system, or a venous cryoneurolysis-specific reference matrix for the practitioner.

For example, in order to target the tibial nerve, the practitioner may reference the table in FIG. 32 to select the posterior tibial vein as an access point. Thereafter, the practitioner may insert a cryoneurolysis catheter into the posterior tibial vein at a location posterior to the medial malleolus. Next, the practitioner may advance the catheter to a location adjacent to the tibial nerve, inflate a cryoneurolysis balloon to achieve circumferential venous wall contact, and cool the balloon to below −20° C. to create a thermal zone including the tibial nerve. After which, practitioner may perform one or more freeze-thaw cycles to induce nerve modulation. Advantageously, one possible therapy of targeting the tibial nerve is the treatment of peripheral neuropathic pain in a foot of a patient.

In still other aspects, the device and methods of venous cryoneurolysis may be applied to a wide variety of other areas, other than those in the lower extremity of the body. In such situations, a pertinent Vein/Nerve Target Map may be needed. For example, FIG. 33 is a table showing a Pelvic Nerve/Vein Target Map with Anatomical Access Landmarks. Advantageously, FIG. 33 is a table detailing additional target nerves for using the inventive venous cryoneurolysis methods and devices in the pelvic region of the body. Further, the table of FIG. 33 provides a reference map, an anatomical guidance system, or a venous cryoneurolysis-specific reference matrix for the practitioner.

For example, in order to target the pudendal nerve, the practitioner may reference the table in FIG. 33 to access the internal pudendal vein via a perineal or transgluteal approach. Thereafter, the practitioner may advance a cryoneurolysis catheter to a position adjacent to the pudendal nerve within Alcock's canal, inflate a cryoneurolysis balloon to conform to the venous wall, and cool the balloon to below −20° C. to induce a thermal lesion in the pudendal nerve. After which, the practitioner may perform one or more freeze-thaw cycles to modulate nerve activity. Advantageously, one possible therapy of targeting the pudendal nerve is the treatment of chronic pelvic neuropathic pain in a patient.

In further aspects, FIG. 34 is a table showing an Upper Extremity Nerve/Vein Target Map with Anatomical Access Landmarks. Advantageously, FIG. 34 is a Table detailing additional target nerves for using the inventive venous cryoneurolysis methods and devices in the upper extremity of the body. Further, the table of FIG. 34 provides a reference map, an anatomical guidance system, or a venous cryoneurolysis-specific reference matrix for the practitioner.

For example, in order to target the ulnar nerve, the practitioner may reference the table in FIG. 34 to access the basilic vein at a location 2 cm distal to the medial epicondyle. Thereafter, the practitioner may advance a balloon cryoneurolysis catheter to a position adjacent to the ulnar nerve at the cubital tunnel, inflate the balloon to conform to the venous wall, and cool the balloon to below −20° C. After which, the practitioner may perform one or more freeze-thaw cycles to achieve cryoneurolysis. Advantageously, one possible therapy of targeting the ulnar nerve is the treatment of ulnar neuropathy in a patient's elbow region.

In still further aspects, FIG. 35 is a table showing a Head and Neck Nerve/Vein Target Map with Anatomical Access Landmarks. Advantageously, FIG. 35 is a table detailing additional target nerves for using the inventive venous cryoneurolysis methods and devices in the head and neck region of the body. Further, the table of FIG. 35 provides a reference map, an anatomical guidance system, or a venous cryoneurolysis-specific reference matrix for the practitioner.

For example, in order to target the greater occipital nerve, the practitioner may reference the table in FIG. 35 to access a posterior branch of the external jugular vein at a location ~5 cm below the occiput. Thereafter, the practitioner may advance a balloon cryoneurolysis catheter along the vein until it is adjacent to the greater occipital nerve, inflate the balloon, and cool the balloon to below −20° C. to achieve cryoneurolysis. After which, the practitioner may perform one or more freeze-thaw cycles to modulate nerve activity and relieve pain. Advantageously, one possible therapy of targeting the greater occipital nerve is the treatment of occipital neuralgia in a patient.

As is clear from the various alternative uses and methods provided in FIGS. 32, 33, 34 and 35, there are still other implementations of the embodiments of the device and methods described herein. Advantageously, embodiments of the inventive device and method may be used to provide cryoneurolysis as needed for a number of the different indications detailed in "The Applications of Cryoneurolysis for Acute and Chronic Pain" a review article by Emily Biel et al. (see Pain Practice. 2023; 23:204-215; accessed online April 2025 DOI:10.1111/papr.13182), incorporated herein by reference for all purposes. In still other optional configurations, embodiments of the balloon-based cryoneurolysis device may be modified to include controls, features or other auxiliary components as described in U.S. Patent Application Publication US 2005/0038421 entitled "Controllable Pressure Cryogenic Balloon Treatment System and Method" filed on Jun. 4, 2003; U.S. Patent Application Publication US 2008/0312644 entitled "Cryogenic Balloon Ablation Instruments and Systems" filed on Jun. 14, 2007; or U.S. Pat. No. 6,786,901 entitled "Cryosurgical Fluid Supply" filed on Mar. 15, 1999. These patent applications and patents are incorporated herein by reference for all purposes.

In still other alternative implementations, various different implementations of the inventive device and methods may be advantageously applied to perform an embodiment of a transvenous cryoneurolysis procedure as detailed in FIG. 36. Still further, it is to be appreciated that the methods 3000 and 3100 may be modified in order to implement relief of a patient's symptom or symptoms, form an appropriately sized axial cryolesion, enter a target vein or position a transvenous cryoneurolysis device adjacent to a target nerve so as to provide a transvenous cryoneurolysis procedure as described in the Tables provided in FIGS. 32-36.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of performing a transvenous cryoneurolysis procedure to treat a symptom of peripheral neuropathy in a lower limb of a patient, comprising:
   Identifying a target neurosome in the lower limb of the patient for performing the transvenous cryoneurolysis procedure to provide relief to the symptom of peripheral neuropathy in the lower limb of the patient;
   Identifying a target nerve associated with the target neurosome of the lower limb of the patient, the target nerve selected from the group consisting of: the saphenous nerve, the deep peroneal nerve, the tibial nerve and the sural nerve;
   Selecting a target vein for accessing the venous vasculature in proximity to the target nerve;
   Inserting the transvenous cryoneurolysis device into the target vein in proximity to an ankle of the patient;
   Advancing the transvenous cryoneurolysis device along the target vein to a treatment position in proximity to the target nerve;
   Inflating the transvenous cryoneurolysis device to distend the target vein to a diameter from 5 mm to 9 mm;
   Performing at least one freeze-thaw cryoneurolysis cycle to maintain a temperature at the target nerve within a range of −20 C to −80 C sufficient to induce Sunderland II axonotmesis of sensory fibers of the target nerve;
   Deflating the transvenous cryoneurolysis device after a last cryoneurolysis freeze-thaw cycle; and
   Removing the transvenous cryoneurolysis device from the target vein.

2. The method of claim 1 wherein inserting the transvenous cryoneurolysis device into the target vein is selected such that the advancing the transvenous cryoneurolysis device along the target vein to the treatment position includes antegrade motion of the transvenous cryoneurolysis device along the target vein.

3. The method of claim 1 wherein the inflating the transvenous cryoneurolysis device step reduces the distance between the transvenous cryoneurolysis device and a portion of the target nerve in proximity to the target vein.

4. The method of claim 1 further comprising maintaining a distending force on the target vein with the transvenous cryoneurolysis device during the at least one freeze thaw cycle.

5. The method of claim 1 wherein after the performing step an axial cryolesion with a length from 1 cm to 10 cm is formed along the target nerve.

6. The method of claim 5 wherein the length of the axial cryolesion along the target nerve is related to a length of the inflated portion of the transvenous cryoneurolysis device.

7. The method of claim 1 wherein the symptom of peripheral neuropathy in the lower limb of the patient is related to a leg, an ankle or a foot of the patient.

8. The method of claim 1 wherein the target nerve is the saphenous nerve and the target vein is the great saphenous vein.

9. The method of claim 8, wherein the step of inserting the transvenous cryoneurolysis device is performed using an access point anatomical landmark that is anterior to the medial malleolus of the ankle of the patient.

10. The method of claim 1 wherein the symptom of peripheral neuropathy of the lower limb of the patient is degraded sensation to the heel and sole of the foot.

11. The method of claim 1 wherein the target nerve is the tibial nerve.

12. The method of claim 11 wherein the target vein is the posterior tibial vein and the step of inserting the transvenous cryoneurolysis device is performed using an access point anatomical landmark that is posterior to the medial malleolus of the ankle of the patient.

13. The method of claim 1 wherein the symptom of peripheral neuropathy of the lower limb of the patient is deteriorated sensation to the web space between the first and second toes or associated with a portion of the dorsal aspect of the foot.

14. The method of claim 1 wherein the target nerve is the Deep Peroneal Nerve.

15. The method of claim 14 wherein the target vein is the anterior tibial vein and the step of inserting the transvenous cryoneurolysis device is performed using an access point anatomical landmark that is midway between the tibia and the fibula at the ankle and lateral to the extensor hallucis longus.

16. The method of claim 1 wherein the transvenous cryoneurolysis device used to perform the method has an overall length from a handle on a proximal portion of a catheter to a distal most end of the device that is less than 30 cm or is 25 cm, or is 20 cm, or is 15 cm.

17. The method of claim 1 wherein, during the step of performing at least one freeze-thaw cryoneurolysis cycle, a length of a catheter shaft of the transvenous cryoneurolysis device proximal to a most proximal portion of the balloon and within the target vein is less than 20 cm.

18. The method of claim 1, wherein the symptom of peripheral neuropathy in the lower limb of the patient is deteriorated sensation to the outside of the lower leg, ankle or foot.

19. The method of claim 1, wherein the target nerve is the sural nerve and the target vein is the short saphenous vein.

20. The method of claim 19, wherein the step of inserting the transvenous cryoneurolysis device is performed using an access point anatomical landmark that is along a lateral aspect of the ankle.

21. A method of performing transvenous cryoneurolysis for temporary cryoanalgesia of a symptom of a patient, comprising:

Selecting a vein of the patient as a target vein for a transvenous cryoneurolysis access point;

Inserting a transvenous cryoneurolysis device into the target vein;

Advancing the transvenous cryoneurolysis device to a location within the target vein that is 3 mm to 7 mm from a target nerve associated with the symptom of the patient;

Inflating a balloon of the transvenous cryoneurolysis device to expand the target vein to a diameter of 5 mm to 12 mm to reduce a distance between the balloon and the target nerve;

Cooling the balloon to a temperature below −20° C. to create a thermal zone including the motor fibers and the sensory fibers of the target nerve, wherein the thermal zone remains in a temperature in the range of −20° C. to −80° C. to induce Sunderland II axonotmesis in the sensory fibers of the target nerve;

Performing one or more freeze-thaw cycles with the balloon for inducing temporary cryoanalgesia of a portion of the sensory fibers of the target nerve to provide the patient relief of the symptom;

wherein after the step of selecting a vein of the patient as a target vein there is a step of using the target vein to select a target vein/nerve pair and an ankle access landmark combination selected from the group consisting of:

(a) great saphenous vein/saphenous nerve, with an access point anterior and superior to the medial malleolus;

(b) posterior tibial vein/tibial nerve, with an access point posterior to the medial malleolus;

(c) anterior tibial vein/deep peroneal nerve, with an access point midway between the tibia and fibula and lateral to the extensor hallucis longus tendon; and (d) small saphenous vein/sural nerve, with an access point at or posterior to the lateral malleolus.

22. The method of claim 21 wherein the target vein is one of the great saphenous vein, the posterior tibial vein, the small saphenous vein or the anterior tibial vein.

23. The method of claim 22 wherein the target nerve is one of a saphenous nerve, a tibial nerve, a sural nerve or a deep peroneal nerve and the symptom of the patient is related to peripheral neuropathy.

24. The method of claim 23 wherein the inserting step is performed at a location in the target vein wherein the distance from the access point in the target vein to the location adjacent to the target nerve is less than 20 cm and the movement of the transvenous cryoneurolysis device from the access point to the location adjacent to the target nerve includes antegrade motion along the target vein.

25. The method of claim 21 wherein after the performing step a cryolesion is formed along the target nerve having a length related to a length of the balloon of the transvenous cryoneurolysis device.

* * * * *